United States Patent
Watkins et al.

(10) Patent No.: US 6,989,261 B2
(45) Date of Patent: Jan. 24, 2006

(54) BUTYRYLCHOLINESTERASE VARIANT POLYPEPTIDES WITH INCREASED CATALYTIC EFFICIENCY AND METHODS OF USE

(75) Inventors: Jeffry D. Watkins, Encinitas, CA (US); James D. Pancook, San Diego, CA (US)

(73) Assignee: Eli Lilly and Company, Indianapolis, IN (US)

(*)

OTHER PUBLICATIONS

Kunkel, "Rapid and Efficient Site–Specific Mutagenesis Without Phenotypic Selection." Proc. Natl. Acad. Sci. USA; 1985, vol. 82, 488–492.

Lockridge, et al., "A Single Amino Acid Substitution, Gly117His, Confers Phosphotriesterase (Organophosphorus Acid Anhydride Hydrolase) Activity on Human Butyrylcholinesterase." Biochemistry; 1997, vol. 36: 786–795.

McTiernan, et al., "Brain cDNA Clone for Human Cholinesterase." Proc. Natl. Acad. Sci. USA; 1987, vol. 84: 6682–6686.

Masson, et al., "Role of Aspartate 70 and Tryptophan 82 in Binding of Succinyldithiocholine to Human Butyrylcholinesterase." Biochemistry; 1997, vol. 36: 2266–2277.

Mets, et al., "A Catalytic Antibody Against Cocaine Prevents Cocaine's Reinforcing and Toxic Effects in Rats." Proc. Natl. Acad. Sci. USA; 1998, vol. 95:10176–10181.

Sauer, et al., "Site–Specific DNA Recombination in Mammalian Cells by the Cre Recombinase of Bacteriophage P1." Proc. Natl. Acad. Sci. USA; 1998, vol. 85 5166–5170.

Schwarz, et al., "Engineering of Human Cholinesterases Explains and Predicts Diverse Consequences of Administration of Various Drugs and Poisons." Pharmac. Ther.; 1995, vol. 67:283–322.

Soreq, et al., "Excavations into the Active–Site Gorge of Cholinesterases." Trends Biochem. Science; 1992, vol. 17: 353–358.

Stemmer, "DNA Shuffling by Random Fragmentation and Reassembly: *In vitro* Recombination for Molecular Evolution." Proc. Natl. Acad. Sci. USA; 1994, vol. 91: 10747–10751.

Sun, et al., "Re–engineering Butyrylcholinesterase as a Cocaine Hydrolase." Molecular Pharmacology; 2002, vol. 62, No. 2: 220–224.

Sussman, et al., "Atomic Structure of Acetylcholinesterase From *Torpedo californica*: A Prototypic Acetylcholine–Binding Protein." Science; 1991, vol. 253: 872–879.

Tatusova, et al., "Blast 2 Sequences, a New Tool For Comparing Protein and Nucleotide Sequences." FEMS Microbiol. Lett.; 1999, vol. 174: 247–250.

Watkins, et al., "Determination of the Relative Affinities of Antibody Fragments Expressed in *Escherichia Coli* by Enzyme–Linked Immunosorbent Assay." Analy. Biochem.; 1997, vol. 253: 37–45.

Wu, et al., "Humanization of a Murine Monoclonal Antibody by Simultaneous Optimization of Framework and CDR Residues." J. Mol. Biol.; 1999, vol. 294:151–162.

Wu, et al., "Stepwise *in vitro* Affinity Maturation of Vitaxin, an $a_v\beta_3$ —Specific Humanized mAb." Proc. Natl. Acad. Sci. USA; 1998, vol. 95: 6037–6042.

Xie, et al., "An Improved Cocaine Hydrolase: The A328Y Mutant of Human Butyrylcholinesterase Is 4–Fold More Efficient." Molecular Pharmacology; 1999, vol. 55: 83–91 (XP002236142).

Library 6

```
                      328           331 332
WT      GAT GAA GGG ACA CCT TTT TTA GTC TAT GGT GCT CCT
         T   A   F   L   V   Y
Y332S   GAT GAA GGG ACA CCT TTT TTA GTC TCG GGT GCT CCT
         T   A   F   L   V   S
Y332M   GAT GAA GGG ACA CCT TTT TTA GTC ATG GGT GCT CCT
         T   A   F   L   V   M
Y332P   GAT GAA GGG ACA CCT TTT TTA GTC CCA GGT GCT CCT
         T   A   F   L   V   P
V331L   GAT GAA GGG ACA GCT TTT TTA TTG TAT GGT GCT CCT
         T   A   F   L   L   Y
A328W   GAT GAA GGG ACA TGG TTT TTA GTC TAT GGT GCT CCT
         T   W   F   L   V   Y
```

Library 5

```
                                              285     287
WT      CTG AAT GAA GCA TTT GTT GTC CCC TAT GGG ACT CCT TTG TCA GTA AAC TTT GGT CCG
         A   F   V   V   P   Y   G   T   P   L   S   V   N
S287G   CTG AAT GAA GCA TTT GTT GTC CCC TAT GGG ACT CCT TTG GGT GTA AAC TTT GGT CCG
         A   F   V   V   P   Y   G   T   P   L   G   V   N
P285Q   CTG AAT GAA GCA TTT GTT GTC CCC TAT GGG ACT CAG TTG TCA GTA AAC TTT GGT CCG
         A   F   V   V   P   Y   G   T   Q   L   S   V   N
P285S   CTG AAT GAA CCA TTT GTT GTC CCC TAT GGG ACT AGC TTG TCA GTA AAC TTT GGT CCG
         A   F   V   V   P   Y   G   T   S   L   S   V   N
```

Library 4

```
                        227
WT      ATT CTG CAA AGT GGT TCC TTT AAT GCT CCT TGG GCG GTA ACA TCT CTT TAT
         S   G   S   F   N   A   P   W   A   V   T
F227A   ATT CTG CAA AGT GGT TCC GCG AAT GCT CCT TGG GCG GTA ACA TCT CTT TAT
         S   G   S   A   N   A   P   W   A   V   T
F227G   ATT CTG CAA AGT GGT TCC GGG AAT GCT CCT TGG GCG GTA ACA TCT CTT TAT
         S   G   S   G   N   A   P   W   A   V   T
F227S   ATT CTG CAA AGT GGT TCC AGT AAT GCT CCT TGG GCG GTA ACA TCT CTT TAT
         S   G   S   S   N   A   P   W   A   V   T
F227P   ATT CTG CAA AGT GGT TCC CCG AAT GCT CCT TGG GCG GTA ACA TCT CTT TAT
         S   G   S   P   N   A   P   W   A   V   T
F227T   ATT CTG CAA AGT GGT TCC ACT AAT GCT CCT TGG GCG GTA ACA TCT CTT TAT
         S   G   S   T   N   A   P   W   A   V   T
F227C   ATT CTG CAA AGT GGT TCC TGT AAT GCT CCT TGG GCG GTA ACA TCT CTT TAT
         S   G   S   C   N   A   P   W   A   V   T
F227M   ATT CTG CAA AGT GGT TCC ATG AAT GCT CCT TGG GCG GTA ACA TCT CTT TAT
         S   G   S   M   N   A   P   W   A   V   T
```

Library 3

```
                            199
WT      AGT GTA ACT CTC TTT GGA GAA AGT GCA GGA GCA GCT TCA GTT
         L   F   G   E   S   A   G   A
A199S   AGT GTA ACT CTC TTT GGA GAA AGT TCA GGA GCA GCT TCA GTT
         L   F   G   E   S   S   G   A
```

FIGURE 1

```
         10             20            30            40            50
EDDIIIATKNGKVRGMNLTVFGGTVTAFLGIPYAQPPLGRLRFKKPQSLTK
         60             70            80            90           100
WSDIWNATKYANSCCQNIDQSFPGFHGSEMWNPNTDLSEDCLYLNVWIPAP
        110            120           130           140           150
KPKNATVLIWIYGGGFQTGTSSLHVYDGKFLARVERVIVVSMNYRVGALGF
        160            170           180           190           200
LALPGNPEAPGNMGLFDQQLALQWVQKNIAAFGGNPKSVTLFGESAGAASV
        210            220           230           240           250
SLHLLSPGSHSLFTRAILQSGSFNAPWAVTSLYEARNRTLNLAKLTGCSRE
        260            270           280           290           300
NETEIIKCLRNKDPQEILLNEAFVVPYGTPLSVNFGPTVDGDFLTDMPDIL
        310            320           330           340           350
LELGQFKKTQILVGVNKDEGTAFLVYGAPGFSKDNNSIITRKEFQEGLKIF
        360            370           380           390           400
FPGVSEFGKESILFHYTDWVDDQRPENYREALGDVVGDYNFICPALEFTKK
        410            420           430           440           450
FSEWGNNAFFYYFEHRSSKLPWPEWMGVMHGYEIEFVFGLPLERRDNYTKA
        460            470           480           490           500          510
EEILSRSIVKRWANFAKYGNPNETQNNSTSWPVFKSTEQKYLTLNTESTRI
        520            530           540           550           560
MTKLRAQQCRFWTSFFPKVLEMTGNIDEAEWEWKAGFHRWNNYMMDWKNQF
        570
NDYTSKKESCVGL
```

Figure 2

```
   1 tactgaatgt cagtgcagtc caatttacag gctggagcag cagctgcatc ctgcatttcc
  61 ccgaagtatt acatgatttt cactccttgc aaactttacc atctttgttg cagagaatcg
 121 gaaatcaata tgcatagcaa agtcacaatc atatgcatca gatttctctt ttggtttctt
 181 ttgctctgca tgcttattgg gaagtcacat actgaagatg acatcataat tgcaacaaag
 241 aatggaaaag tcagagggat gaacttgaca gtttttggtg gcacggtaac agcctttctt
 301 ggaattccct atgcacagcc acctcttggt agacttcgat tcaaaaagcc acagtctctg
 361 accaagtggt ctgatatttg gaatgccaca aaatatgcaa attcttgctg tcagaacata
 421 gatcaaagtt tccaggcttc catggatca gagatgtgga acccaaacac tgacctcagt
 481 gaagactgtt tatatctaaa tgtatggatt ccagcaccta accaaaaaa tgccactgta
 541 ttgatatgga tttatggtgg tggttttcaa actggaacat catctttaca tgtttatgat
 601 ggcaagtttc tggctcgggt tgaaagagtt attgtagtgt caatgaacta tagggtgggt
 661 gccctaggat tcttagcttt gccaggaaat cctgaggctc cagggaacat gggtttattt
 721 gatcaacagt tggctcttca gtgggttcaa aaaatatag cagcctttgg tggaaatcct
 781 aaaagtgtaa ctctcttggg agaaagtgca ggagcagctt cagttagcct gcatttgctt
 841 tctcctggaa gccattcatt gttcaccaga gccattctgc aaagtggatc ctttaatgct
 901 ccttgggcgg taacatctct ttatgaagct aggaacagaa cgttgaactt agctaaattg
 961 actggttgct ctagagagaa tgagactgaa ataatcaagt gtcttagaaa taagatccc
1021 caagaaattc ttctgaatga agcatttgtt gtccctatg ggactccttt gtcagtaaac
1081 tttggtccga ccgtggatgg tgattttctc actgacatgc agacatatt acttgaactt
1141 ggacaattta aaaaaaccca gatttggtg ggtgttaata agatgaagg gacagctttt
1201 ttagtctatg gtgctcctgg cttcagcaaa gataacaata gtatcataac tagaaaagaa
1261 tttcaggaag gtttaaaaat atttttcca ggagtgagtg agtttggaaa ggaatccatc
1321 ctttttcatt acacagactg ggtagatgat cagagacctg aaaactaccg tgaggccttg
1381 ggtgatgttg ttggggatta taatttcata tgccctgcct tggagttcac caagaagttc
1441 tcagaatggg gaaataatgc ctttttctac tatttgaac accgatccta caacttccg
1501 tgcccagaat ggatgggagt gatgcatggc tatgaaattg aatttgtctt tggtttacct
1561 ctggaaagaa gagataatta cacaaaagcc gaggaaattt tgagtagatc catagtgaaa
1621 cggtgggcaa attttgcaaa atatgggaat ccaatgaga ctcagaacaa tagcacaagc
1681 tggcctgtct tcaaaagcac tgaacaaaaa tatctaacct tgaatacaga gtcaacaaga
1741 ataatgacga aactacgtgc tcaacaatgt cgattctgga catcattttt tccaaaagtc
1801 ttggaaatga caggaaatat tgatgaagca gaatgggagt ggaaagcagg attccatcgc
1861 tggaacaatt acatgatgga ctggaaaaat caatttaacg attacactag caagaagaa
1921 agttgtgtgg gtctctaatt aatagattta ccctttatag aacatatttt cctttagatc
1981 aaggcaaaaa tatcaggaagc ttttttacac acctactaaa aaagttatta tgtagctgaa
```

Figure 3A

```
2041 acaaaaatgc cagaaggata atattgattc ctcacatctt taacttagta ttttacctag
2101 catttcaaaa cccaaatggc tagaacatgt ttaattaaat ttcacaatat aaagttctac
2161 agttaattat gtgcatatta aaacaatggc ctggttcaat ttctttcttt ccttaataaa
2221 tttaagtattt ttcccccaa aattatcagt gctctgcttt tagtcacgtg tatttcatt
2281 accactcgta aaaggtatc tttttaaat gaattaaata ttgaaacact gtacaccata
2341 gtttacaata ttatgtttcc taattaaaat aagaattgaa tgtcaatatg agatattaaa
2401 ataagcacag aaaatc
```

Figure 3B

```
                                                    1         10        20        30
HUMAN WILD-TYPE BChE                          EDDIIIATKN GKVRGMNLTV PGGTVTAFLG
HUMAN A VARIANT BChE                          ---------- ---------- ----------
HUMAN J VARIANT BChE                          ---------- ---------- ----------
HUMAN K VARIANT BChE                          ---------- ---------- ----------
RAT BChE                                      EEDVIITKT  GEVRGLSMPI LGGTVTAFLG
CAT BChE                                      EEDIIIITTKN GKVRGMNLPV LDGTVTAFLG
HORSE BChE                                    EEDIIIPTKN GKVRGMNLPV LGGTVTAFLG 40         50        60        70        80        90       100
HUMAN WT     IPYAQPPLGR LRFKKPQSLT KWSDIWNATK YANSCCQNID QSFPGFHGSE MWNPNTDLSE DCLYLNVWIP
HUMAN A      ---------- ---------- ---------- ---------- ---------G ---------- ----------
HUMAN J      ---------- ---------- ---------- ---------- ---------- ---------- ----------
HUMAN K      ---------- ---------- ---------- ---------- ---------- ---------- ----------
RAT          IPYAQPPLGS LRFKKPQPLN KWPDVYNATK YANSCYQNID QAFPGFQGSE MWNPNTNLSE DCLYLNVWIP
CAT          IPYAQPPLGR LRFKKPQPLT KWSDIWNATK YANSCYQNAD QSFPGFPGSE MWNPNTDLSE DCLYLNVWIP
HORSE        IPYAQPPLGR LRFKKPQSLT KWSNIWNATK YANSCYQNTD QSFPGFLGSE MWNPNTELSE DCLYLNVWIP 110        120       130       140       150       160       170
HUMAN WT     APKPKNATVL IWIYGGGFQT GTSSLHVYDG KFLARVERVI VVSMNYRVGA LGFLALPGNP EAPGNMGLFD
HUMAN A      ---------- ---------- ---------- ---------- ---------- ---------- ----------
HUMAN J      ---------- ---------- ---------- ---------- ---------- ---------- ----------
HUMAN K      ---------- ---------- ---------- ---------- ---------- ---------- ----------
RAT          VPKPKNATVM VWIYGGGFQT GTSSLPVYDG KFLTRVERVI VVSMNYRVGA LGFLAPPGNS EAPGNMCLFD
CAT          TPKPKNATVM IWIYGGGFQT GTSSLPVYDG KFLARVERVI VVSMNYRVGA LGFLALPGNP EVPGNMGLFD
HORSE        APKPKNATVM IWIYGGGFQT GTSSLPVYDG KFLARVERVI VVSMNYRVGA LGFLALSENP EAPGNMGLFD 180        190       200       210       220       230       240
HUMAN WT     QQLALQWVQK NIAAFGGNPK SVTLFGESAG AASVSLHLLS PGSHSLFTRA ILQSGSFNAP WAVTSLYEAR
HUMAN A      ---------- ---------- ---------- ---------- ---------- ---------- ----------
HUMAN J      ---------- ---------- ---------- ---------- ---------- ---------- ----------
HUMAN K      ---------- ---------- ---------- ---------- ---------- ---------- ----------
RAT          QQLALQWIQR NIAAFGGNPK SVTLFGESAG AASVSLHLLC PQSYPLFTRA ILESGSSNAP WAVKEPEEAR
CAT          QQLALQWVQK NIAAFGGNPK SVTLFGESAG ACSVSLHLLS PRSQPLFTRA ILQSGSSNAP WAVMSLDEAR
HORSE        QQLALQWVQK NIAAFGGNPP SVTLFGESAG AASVSLHLLS PRSQPLFTRA ILQSGSSNAP WAVTSLYEAR 250        260       270       280       290       300       310
HUMAN WT     NRTLNLAKLT GCSRENETEI IKCLRNKDPQ EILLNEAFVV PYGTPLSVNF GPTVDGDFLT DMPDILLELG
HUMAN A      ---------- ---------- ---------- ---------- ---------- ---------- ----------
HUMAN J      ---------- ---------- ---------- ---------- ---------- ---------- ----------
HUMAN K      ---------- ---------- ---------- ---------- ---------- ---------- ----------
RAT          NRTLLLAKFI GCSKENEKEI IKCLRSKDPQ EILLNEKLVL PSDSIPSINF GPTVDGDFLT DMPHTLLQLG
CAT          NRTLPLAKFI GCSKENDTEI IKCLRNKDPQ EILLNELLVV PSDTLLSVNF GVVDGDFLT  QMPDTLLQLG
HORSE        NRTLPLAKRM GCSPDNETEM IKCLRDKDPQ EILLNEVFVV PYDTLLSVNF GPTVDGDFLT QMPDTLLQLG
```

Figure 4A

```
                    320        330        340        350        360        370        380
HUMAN WT    QFKKTQILVG VNKDEGTAFL VYGAPGFSKD NNSIITRKEF QEGLKIFFPG VSEFCKESIL FHYTDWVDDQ
HUMAN A     ---------- ---------- ---------- ---------- ---------- ---------- ----------
HUMAN J     ---------- ---------- ---------- ---------- ---------- ---------- ----------
HUMAN K     ---------- ---------- ---------- ---------- ---------- ---------- ----------
RAT         KVKTAQILVG VNKDEGTAFL VYGAPGFSKD NDSLITRKEF QEGLNMIFPG VSSLCKEAIL FYVVDWLCDQ
CAT         QFKKTQILVG VNKDEGTAFL VYGAPGFSKD NDSIITRKEF QEGLKIYFPG VSEFGREAIL FYYVDLLDDQ
HORSE       QFKKTQILVG VNKDEGTAFL VYGAPGFSKD NNSIITRKEF QEGLKIFFPR VSEFGRESIL FHTMDWLDDQ 390        400        410        420        430        440        450
HUMAN WT    RPENYREALG DVVGDYNFIC PALEFTKKFS EWGNNAFYYI FEHRSSKLPW PEWMGVMHGY EIEFVFGLPL
HUMAN A     ---------- ---------- ---------- ---------- ---------- ---------- ----------
HUMAN J     ---------- ---------- ---------- ---------- ---------- ---------- ----------
HUMAN K     ---------- ---------- ---------- ---------- ---------- ---------- ----------
RAT         TPEVYREALD DIIGDYNIIC PALEFTKKFA ELEINAFYYI FEHRSSKLPW PEWMGVMHGY EIEFVFGLPL
CAT         RAEKYREALD DVLGDYNIIC PALEFTTKFS ELGNRAFYYI FEHRSSQLPW PEWMGVMHGY EIEFVFGLPL
HORSE       RAENYREALD DVVGDYNIIC PALEFTRKFS ELGNDAFYYI FEHRSTKLPW PEWMGVMHGY EIEFVFGLPL 460        470        480        490        500        510        520
HUMAN WT    ERRDNYTKAE EILSRSIVKE WANFAKYGNP NETQNNSTSW PVFKSTEQKY LTLNTESTRI MTKLRAQQCR
HUMAN A     ---------- ---------- ---------- ---------- ---------- ---------- ----------
HUMAN J     ---------- ---------- ---------- ---------- ---------- ---------- ----------
HUMAN K     ---------- ---------- ---------- ---------- ---------- ---------- ----------
RAT         ERRVNYTRAE EIFSPSIMKT WANFAKYGHP NGTQGNSTVW PVFTSTEQKY LTLNTEKSKI NSKLRAPQCQ
CAT         EREVNYTRAE EILSRSIMNY WANFAKYGNP NGTQNNSTRW PAFRSTDQKY LTLNAESPKV YTKLRAQQCR
HORSE       ERRVNYTRAE EILSRSIMKE WANFAKYGNP NGTQNNSTRW PVFKSTEQKY LTLNTESPKV YTKLRAQQCR 530        540        550        560        570    574
HUMAN WT    FWTSFFPKVL EMTGNIDEAE WEWKAGFHRW NNYMMDWKNQ FNDYTSKKES CVGL
HUMAN A     ---------- ---------- ---------- ---------- ---------- ----
HUMAN J     ---------- ---------- ---------- ---------- ---------- ----
HUMAN K     ---------- ---------- ---------- ---------- ---------- ----
RAT         FWRLFTPKVL EITGDIDERE QEWKAGFHRW SNYMMDWKNQ FNDYTSKKES CTDL
CAT         FWTLFFPKVL EMTGNIDEAE REWKAGFYRW NNYMMDWKNQ FNDYTSKKES CACL
HORSE       FWTLFFPKVL ELTGNIDEAE REWKAGFYRW NNYMMDWKNQ FNDYTSKKES CSDF
```

Figure 4B

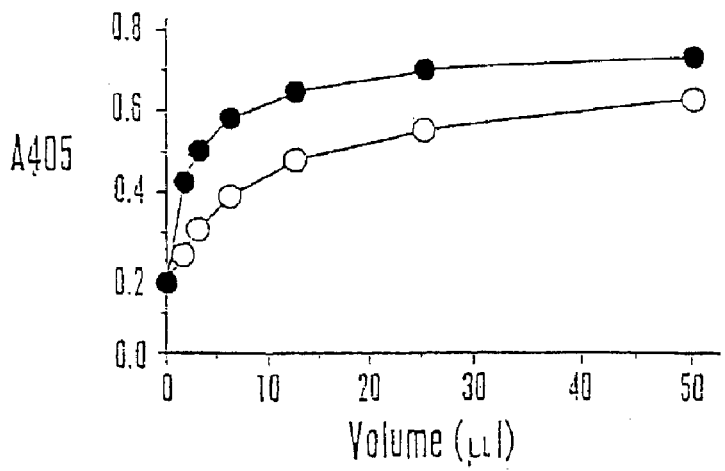
Figure 6
Figure 7
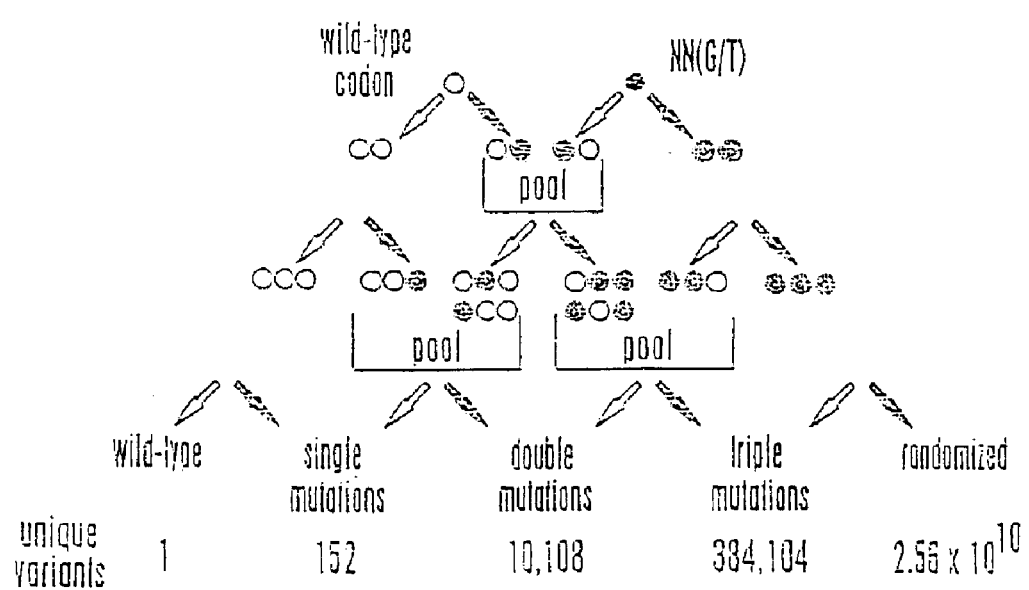

BUTYRYLCHOLINESTERASE VARIANT POLYPEPTIDES WITH INCREASED CATALYTIC EFFICIENCY AND METHODS OF USE

This application is a continuation-in-part of U.S. Ser. No. 10/324,466, filed Dec. 20, 2002, which claims benefit of provisional application Ser. No. 60/560,741, filed Dec. 20, 2001, which was converted to a provisional application by Petition Under 37 C.F.R. §1.53(c)(2)(i), and is incorporated herein by reference in its entirety.

This invention was made with government support under grant number 1R01 DA011707 awarded by the National Institutes of Health. The United States Government has certain rights in this invention.

BACKGROUND OF THE INVENTION

The present invention relates generally to the fields of computational chemistry and molecular modeling and, more specifically, to butyrylcholinesterase polypeptide variants with increased catalytic efficiency.

Cocaine abuse is a significant social and medical problem in the United States as evidenced by the estimated 3.6 million chronic users. Cocaine abuse often leads to long-term dependency as well as life-threatening overdoses. However, no effective antagonist is currently available that combats the reinforcing and toxic effects of cocaine.

One difficulty in identifying an antagonist to treat cocaine abuse arises largely from the narcotic's mechanism of action. Specifically, cocaine inhibits the, re-uptake of neurotransmitters resulting in over-stimulation of the reward pathway. It is this over-stimulation that is proposed to be the basis of cocaine's reinforcing effect. In addition, at higher concentrations, cocaine interacts with multiple receptors in both the central nervous and cardiovascular systems, leading to toxicities associated with overdose. Because of this multifarious mechanism of action of cocaine, it is difficult to identify selective antagonists to treat both the reinforcing and toxic effects of cocaine. Additionally, antagonists that block cocaine's binding to its receptors tend to display many of the same deleterious effects as cocaine.

Recently, alternative treatment strategies based on intercepting and neutralizing cocaine in the bloodstream have been proposed. For example, dopamine D1, D2, and D3 antagonists affect the reinforcing potency of cocaine in the rat model, these antagonists display a narrow range of effective doses and the extent of decrease in cocaine potency is quite small. In addition, these dopamine antagonists produce profound decreases in other behaviors when the doses are increased only slightly above the levels that display an effect on cocaine self-administration behavior.

A separate treatment strategy involves partial protection against the effects of cocaine using antibody-based approaches. Limitations of immunization approaches include the stoichiometric depletion of the antibody following the binding of cocaine. The use of a catalytic antibody, which metabolizes cocaine in the bloodstream, partially mitigates this problem by degrading and releasing cocaine, permitting binding of additional cocaine. However, the best catalytic antibody identified to date metabolizes cocaine significantly slower than endogenous human serum esterases.

In vivo, cocaine is metabolized by three principal routes: 1) N-demethylation in the liver to form norcocaine, 2) hydrolysis by serum and liver esterases to form ecgonine methyl ester, and 3) nonenzymatic hydrolysis to form benzoylecgonine. In humans, norcocaine is a minor metabolite, while benzoylecgonine and ecgonine methyl ester account for about 90% of a given dose. The metabolites of cocaine are rapidly cleared and appear not to display the toxic or reinforcing effects of cocaine. Low serum levels of butyrylcholinesterase have been correlated with adverse physiological events following cocaine overdose, providing further evidence that butyrylcholinesterase accounts for the cocaine hydrolysis activity observed in plasma. Human plasma obtained from individuals with a defective version of the butyrylcholinesterase gene has been shown to have little or no ability to hydrolyze cocaine in vitro, and the hydrolysis of cocaine in plasma of individuals carrying one defective and one wild type copy of the butyrylcholinesterase gene has been shown to proceed at one-half the normal rate. Therefore, it has been suggested that individuals with defective versions of the butyrylcholinesterase gene are at higher risk for life-threatening reactions to cocaine. Recently, administration of butyrylcholinesterase has been demonstrated to confer limited protection against cocaine overdose in mice and rats.

Although administration of butyrylcholinesterase provides some effect against cocaine toxicity in vivo, it is not an efficient catalyst of cocaine hydrolysis. The low cocaine hydrolysis activity of wild-type butyrylcholinesterase requires the use of prohibitively large quantities of purified enzyme for therapy.

A number of naturally occurring human butyrylcholinesterases as well as species variations are known, none of which exhibits increased cocaine hydrolysis activity. Similarly, although a variety of recombinantly prepared butyrylcholinesterase mutations have been tested for increased cocaine hydrolysis activity, only one such mutant, termed A328Y, has been identified that exhibits increased cocaine hydrolysis activity. Further butyrylcholinesterase mutations that lead to increased cocaine hydrolysis activity need to be identified to permit clinical evaluation of butyrylcholinesterase.

Thus, there exists a need for recombinant butyrylcholinesterase polypeptides capable of hydrolyzing cocaine significantly more efficiently than wild-type butyrylcholinesterase. The present invention satisfies this need and provides related advantages as well.

SUMMARY OF THE INVENTION

The invention provides a butyrylcholinesterase variant polypeptide having increased cocaine hydrolysis activity as well as the corresponding encoding nucleic acid. The invention further provides methods of hydrolyzing a cocaine-based butyrylcholinesterase substrate as well as methods of treating a cocaine-induced condition with the invention variant.

BRIEF DESCRIPTION OF THE DRAWINGS

FIG. 1 shows alignment of amino acid and nucleic acid sequences for all butyrylcholinesterase variant alterations in their respective regions of human butyrylcholinesterase.

FIG. 2 shows the amino acid sequence of human butyrylcholinesterase (SEQ ID NO: 44).

FIG. 3 shows the nucleic acid sequence of human butyrylcholinesterase (SEQ ID NO: 43).

FIG. 4 shows an amino acid sequence alignment of human wild-type (SEQ ID NO: 44), human A variant (SEQ ID NO: 45), human J variant (SEQ ID NO: 46), human K variant (SEQ ID NO: 47), horse (SEQ ID NO: 48), cat (SEQ ID NO: 49) and rat butyrylcholinesterase variants (SEQ ID NO: 50).

FIG. 6 shows solid phase immobilization of wild-type (filled circles) and truncated (open circles) butyrylcholinesterase for measuring cocaine hydrolysis activity.

FIG. 7 shows the use of multiple synthesis columns and codon-based mutagenesis for the synthesis of focused libraries.

DETAILED DESCRIPTION OF THE INVENTION

Figure 5A:
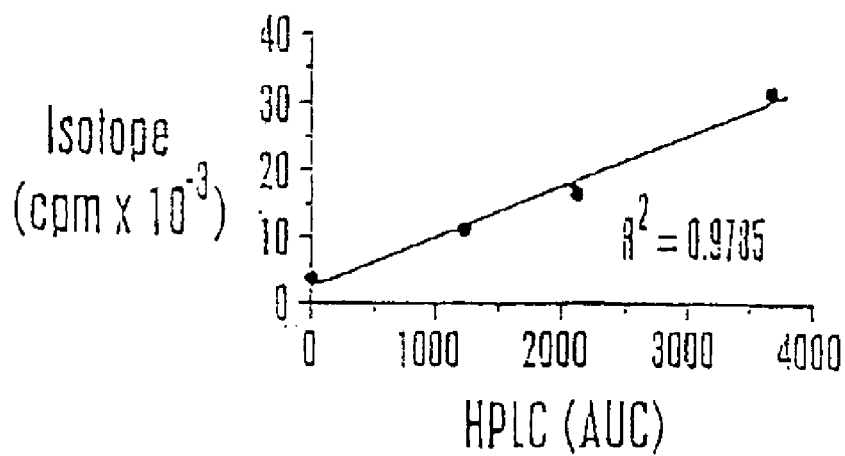
FIG. 5 shows (A) the correlation between the HPLC assay and the isotope tracer assay as demonstrated by plotting the quantitation of benzoic acid formation by both methods, and (B) the $K_m$ for cocaine hydrolysis activity of horse butyrylcholinesterase using the Lineweaver-Burk double-reciprocal plot.

This invention is directed to butyrylcholinesterase variant polypeptides having increased cocaine hydrolysis activity compared to naturally occurring human butyrylcholinesterase, as well as to their encoding nucleic acids. The invention also is directed to methods of hydrolyzing a cocaine-based butyrylcholinesterase substrate and to methods of treating a cocaine-induced condition.

Cholinesterases are ubiquitous, polymorphic carboxylase Type B enzymes capable of hydrolyzing the neurotransmitter acetylcholine and numerous ester-containing compounds. Two major cholinesterases are acetylcholinesterase and butyrylcholinesterase. Butyrylcholinesterase catalyzes the hydrolysis of a number of choline esters as shown:

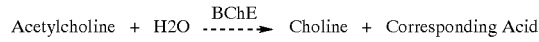

$$\text{Acetylcholine} + \text{H2O} \xrightarrow{\text{BChE}} \text{Choline} + \text{Corresponding Acid}$$

Butyrylcholinesterase preferentially uses butyrylcholine and benzoylcholine as substrates. Butyrylcholinesterase is found in mammalian blood plasma, liver, pancreas, intestinal mucosa and the white matter of the central nervous system. The human gene encoding butyrylcholinesterase is located on chromosome 3 and over thirty naturally occurring genetic variations of butyrylcholinesterase are known. The butyrylcholinesterase polypeptide is 574 amino acids in length and encoded by 1,722 base pairs of coding sequence. Three naturally occurring butyrylcholinesterase variations are the typical alleles referred to as A variant (SEQ ID NO: 45), the J variant (SEQ ID NO: 46) and the K variant (SEQ ID NO: 47), which are aligned in FIG. 4. The A variant has a D70G mutation and is rare (0.5% allelic frequency), while the J variant has an E497V mutation and has only been found in one family. The K variant has a point mutation at nucleotide 1615, which results in an A539T mutation and has an allelic frequency of around 12% in Caucasians.

In addition to the naturally-occurring human variations of butyrylcholinesterase, a number of species variations are known. The amino acid sequence of cat butyrylcholinesterase is 88% identical with human butyrylcholinesterase (see FIG. 4). Of the seventy amino acids that differ, three are located in the active site gorge and are termed A277L, P285L and F398I. Similarly, horse butyrylcholinesterase has three amino acid differences in the active site compared with human butyrylcholinesterase, which are A277V, P285L and F398I (see FIG. 4). The amino acid sequence of rat butyrylcholinesterase contains 6 amino acid differences in the active site gorge, which are A277K, V280L, T284S, P285I, L286R and V288I (see FIG. 4).

Naturally occurring human butyrylcholinesterase variations, species variations as well as recombinantly prepared mutations have previously been described by Xie et al., *Molecular Pharmacology* 55:83–91 (1999). Recombinant human butyrylcholinesterase mutants that have been tested for increased cocaine hydrolysis activity include mutants with the following single or multiple changes: N68Y/Q119/A277W, Q119/V288F/A328Y, Q119Y, E197Q, V288F, A328F, A328Y, F329A and F329S. Out of these mutants, the only butyrylcholinesterase mutant identified that exhibits increased cocaine hydrolysis activity is the A328Y mutant, which has a Tyrosine (Y) rather than an Alanine (A) at amino acid position 328 and exhibits a four-fold increase in cocaine hydrolysis activity compared to human butyrylcholinesterase (Xie et al., supra, 1999).

The invention provides butyrylcholinesterase variant polypeptides encompassing the same or substantially the same amino acid sequence as shown as SEQ ID NOS: 2, 4, 6, 8, 10, 12, 14, 16, 18, 20, 22, 24, 26, 28, 30, 32, 34, 36, 38, 40, 42 and 52 and functional fragments of butyrylcholinesterase variant polypeptides encompassing the same or substantially the same amino acid sequence as shown as SEQ ID NOS: 2, 4, 6, 8, 10, 12, 14, 16, 18, 20, 22, 24, 26, 28, 30, 32, 34, 36, 38, 40, 42 and 52.

The butyrylcholinesterase variant polypeptide encompassing the same or substantially the same amino acid sequence as shown as SEQ ID NO: 2, or functional fragment thereof, has a twenty-four-fold increase in cocaine hydrolysis activity relative to butyrylcholinesterase. The butyrylcholinesterase variant polypeptide encompassing the same or substantially the same amino acid sequence shown as SEQ ID NO: 4, or functional fragment thereof, has a ten-fold increase in cocaine hydrolysis activity relative to butyrylcholinesterase. The butyrylcholinesterase variant polypeptide encompassing the same or substantially the same amino acid sequence shown as SEQ ID NO: 6, or functional fragment thereof, has a sixteen-fold increase in cocaine hydrolysis activity relative to butyrylcholinesterase. The butyrylcholinesterase variant polypeptide encompassing the same or substantially the same amino acid sequence shown as SEQ ID NO: 8, or functional fragment thereof, has a eight-fold increase in cocaine hydrolysis activity relative to butyrylcholinesterase. The butyrylcholinesterase variant polypeptide encompassing the same or substantially the same amino acid sequence shown as SEQ ID NO: 10, or functional fragment thereof, has a one-hundred-fold increase in cocaine hydrolysis activity relative to butyrylcholinesterase. The butyrylcholinesterase variant polypeptide encompassing the same or substantially the same amino acid sequence shown as SEQ ID NO: 12, or functional fragment thereof, has a one-hundred-fold in cocaine hydrolysis activity relative to butyrylcholinesterase. The butyrylcholinesterase variant polypeptide encompassing the same or substantially the same amino acid sequence shown as SEQ ID NO: 14, or functional fragment thereof, has a ninety-seven-fold in cocaine hydrolysis activity relative to butyrylcholinesterase. The butyrylcholinesterase variant polypeptide encompassing the same or substantially the same amino acid sequence shown as SEQ ID NO: 16, or functional fragment thereof, has a ninety-one-fold in cocaine hydrolysis activity relative to butyrylcholinesterase. The butyrylcholinesterase variant polypeptide encompassing the same or substantially the same amino acid sequence shown as SEQ ID NO: 18, or functional fragment thereof, has a sixty-eight-fold in cocaine hydrolysis activity relative to butyrylcholinesterase. The butyrylcholinesterase variant polypeptide encompassing the same or substantially the same amino acid sequence shown as SEQ ID NO: 20, or functional fragment thereof, has an increased cocaine hydrolysis activity relative to butyrylcholinesterase. The butyrylcholinesterase variant polypeptide encompassing the same or substantially the same amino acid sequence shown as SEQ ID NO: 22, or functional fragment thereof, has an increased cocaine hydrolysis activity relative to butyrylcholinesterase. The butyrylcholinesterase variant polypeptide encompassing the same or substantially the same amino acid sequence shown as SEQ ID NO: 24, or functional fragment thereof, has an increased cocaine hydrolysis activity relative to butyrylcholinesterase. The butyrylcholinesterase variant polypeptide encompassing the same or substantially the same amino acid sequence shown as SEQ ID NO: 26, or functional fragment thereof, has an increased cocaine hydrolysis activity relative to butyrylcholinesterase. The butyrylcholinesterase variant polypeptide encompassing the same or substantially the same amino acid sequence shown as SEQ ID NO: 28, or functional fragment thereof, has a four-fold in cocaine hydrolysis activity relative to butyrylcholinesterase. The butyrylcholinesterase variant polypeptide encompassing the same or substantially the same amino acid sequence shown as SEQ ID NO: 30, or functional fragment thereof, has a four-fold increase in cocaine hydrolysis activity relative to butyrylcholinesterase. The butyrylcholinesterase variant polypeptide encompassing the same or substantially the same amino acid sequence shown as SEQ ID NO: 32, or functional fragment thereof, has a two-fold increase in cocaine hydrolysis activity relative to butyrylcholinesterase. The butyrylcholinesterase variant polypeptide encompassing the same or substantially the same amino acid sequence shown as SEQ ID NO: 34, or functional fragment thereof, has a three-fold increase in cocaine hydrolysis activity relative to butyrylcholinesterase. The butyrylcholinesterase variant polypeptide encompassing the same or substantially the same amino acid sequence shown as SEQ ID NO: 36, or functional fragment thereof, has a two-fold increase in cocaine hydrolysis activity relative to butyrylcholinesterase. The butyrylcholinesterase variant polypeptide encompassing the same or substantially the same amino acid sequence shown as SEQ ID NO: 38, or functional fragment thereof, has a two-fold increase in cocaine hydrolysis activity relative to butyrylcholinesterase. The butyrylcholinesterase variant polypeptide encompassing the same or substantially the same amino acid sequence shown as SEQ ID NO: 40, or functional fragment thereof, has a one-and-a-half-fold increase in cocaine hydrolysis activity relative to butyrylcholinesterase. The butyrylcholinesterase variant polypeptide encompassing the same or substantially the same amino acid sequence shown as SEQ ID NO: 42, or functional fragment thereof, has a two-and-a-half-fold increase in cocaine hydrolysis activity relative to butyrylcholinesterase. The butyrylcholinesterase variant polypeptide encompassing the same or substantially the same amino the amino acid sequence shown as SEQ ID NO: 52, or functional fragment thereof, has a one-hundred-fold increase in cocaine hydrolysis activity relative to butyrylcholinesterase.

The butyrylcholinesterase variant polypeptides of the invention hold significant clinical value because of their capability to hydrolyze cocaine at a higher rate than any of the known naturally occurring variants. It is this increase in cocaine hydrolysis activity that enables a much more rapid response to the life-threatening symptoms of cocaine toxicity that confers upon the butyrylcholinesterase variant polypeptides of the invention their therapeutic value. The butyrylcholinesterase variant polypeptides of the invention have two or more amino acid alterations in regions determined to be important for cocaine hydrolysis activity.

As used herein, the term "butyrylcholinesterase" is intended to refer to a polypeptide having the sequence of naturally occurring human butyrylcholinesterase shown as SEQ ID NO: 44.

As used herein, the term "butyrylcholinesterase variant" is intended to refer to a molecule that is structurally similar to a butyrylcholinesterase, but differs by at least one amino acid from the butyrylcholinesterase shown as SEQ ID NO: 44. A butyrylcholinesterase variant is structurally similar to the butyrylcholinesterase shown as SEQ ID NO: 44, but exhibits increased cocaine hydrolysis activity. For example, the cocaine hydrolysis activity of a butyrylcholinesterase variant polypeptide of the invention can be increased by a factor of 5, 6, 7, 8, 9, 10, 12, 14, 16, 18, 20, 24, 28, 32, 36, 40, 80, 100 or more.

A butyrylcholinesterase variant polypeptide can have a one, two, three, four, five, six or more amino acid alterations compared to butyrylcholinesterase. A specific example of a butyrylcholinesterase variant polypeptide has the amino acids Tryptophan and Methionine at positions 328 and 332, respectively, of which the amino acid sequence and encoding nucleic acid sequence is designated as SEQ ID NOS: 2 and 1, respectively. Additional examples of butyrylcholinesterase variant polypeptides are the butyrylcholinesterase variant polypeptide having the amino acids Tryptophan and Proline at positions 328 and 332, respectively of which the amino acid sequence and nucleic acid sequence are described herein and designated SEQ ID NOS: 4 and 3, respectively; the butyrylcholinesterase variant polypeptide having the amino acids Tryptophan and Leucine at positions 328 and 331, respectively, of which the amino acid sequence and nucleic acid sequence are described herein and designated SEQ ID NOS: 6 and 5, respectively; the butyrylcholinesterase variant polypeptide having the amino acids Tryptophan and Serine at positions 328 and 332, respectively, of which the amino acid sequence and nucleic acid sequence are described herein and designated SEQ ID NOS: 8 and 7, respectively; the butyrylcholinesterase variant polypeptide having the amino acids Serine, Alanine, Glycine, Tryptophan and Methionine at positions 199, 227, 287, 328 and 332, respectively, of which the amino acid sequence and nucleic acid sequence are described herein and designated SEQ ID NOS: 10 and 9, respectively; the butyrylcholinesterase variant polypeptide having the amino acids Serine, Alanine, Glycine and Tryptophan at positions 199, 227, 287 and 328, respectively, of which the amino acid sequence and nucleic acid sequence are described herein and designated SEQ ID NOS: 12 and 11, respectively; the butyrylcholinesterase variant polypeptide having the amino acids Serine, Glycine and Tryptophan at positions 199, 287 and 328, respectively, of which the amino acid sequence and nucleic acid sequence are described herein and designated SEQ ID NOS: 14 and 13, respectively; the butyrylcholinesterase variant polypeptide having the amino acids Alanine, Glycine and Tryptophan at positions 227, 287 and 328, respectively, of which the amino acid sequence and nucleic acid sequence are described herein and designated SEQ ID NOS: 16 and 15, respectively; the butyrylcholinesterase variant polypeptide having the amino acids Alanine and Tryptophan at positions 227 and 328, respectively, of which the amino acid sequence and nucleic acid sequence are described herein and designated SEQ ID NOS: 17 and 18, respectively; the butyrylcholinesterase variant polypeptide having the amino acid Serine at position 332, of which the amino acid sequence and nucleic acid sequence are described herein and designated SEQ ID NOS: 20 and 19, respectively; the butyrylcholinesterase variant polypeptide having the amino acid Methionine at position 332, of which the amino acid sequence and nucleic acid sequence are described herein and designated SEQ ID NOS: 22 and 21, respectively; the butyrylcholinesterase variant polypeptide having the amino acid Proline at position 332, of which the amino acid sequence and nucleic acid sequence are described herein and designated SEQ ID NOS: 24 and 23, respectively; the butyrylcholinesterase variant polypeptide having the amino acid Leucine at position 331, of which the amino acid sequence and nucleic acid sequence are described herein and designated SEQ ID NOS: 26 and 25, respectively; the butyrylcholinesterase variant polypeptide having the amino acid Alanine at position 227, of which the amino acid sequence and nucleic acid sequence are described herein and designated SEQ ID NOS: 28 and 27, respectively; the butyrylcholinesterase variant polypeptide having the amino acid Glycine at position 227, of which the amino acid sequence and nucleic acid sequence are described herein and designated SEQ ID NOS: 30 and 29, respectively; the butyrylcholinesterase variant polypeptide having the amino acid Serine at position 227, of which the amino acid sequence and nucleic acid sequence are described herein and designated SEQ ID NOS: 32 and 31, respectively; the butyrylcholinesterase variant polypeptide having the amino acid Proline at position 227, of which the amino acid sequence and nucleic acid sequence are described herein and designated SEQ ID NOS: 34 and 33, respectively; the butyrylcholinesterase variant polypeptide having the amino acid Tyrosine at position 227, of which the amino acid sequence and nucleic acid sequence are described herein and designated SEQ ID NOS: 36 and 35, respectively; the butyrylcholinesterase variant polypeptide having the amino acid Cysteine at position 227, of which the amino acid sequence and nucleic acid sequence are described herein and designated SEQ ID NOS: 38 and 37, respectively; the butyrylcholinesterase variant polypeptide having the amino acid Methionine at position 227, of which the amino acid sequence and nucleic acid sequence are described herein and designated SEQ ID NOS: 40 and 39, respectively; the butyrylcholinesterase variant polypeptide having the amino acid Serine at position 199, of which the amino acid sequence and nucleic acid sequence are described herein and designated SEQ ID NOS: 42 and 41, respectively; and the butyrylcholinesterase variant polypeptide having the amino acids Alanine, Glycine, Tryptophan and Methionine at positions 227, 287, 328 and 332, respectively, of which the amino acid sequence and nucleic acid sequence are described herein and designated SEQ ID NOS: 52 and 51, respectively.

As used herein, the term "polypeptide" is intended to mean two or more amino acids covalently bonded together. A polypeptide of the invention includes small polypeptides having a few or several amino acids as well as large polypeptides having several hundred or more amino acids. Usually, the covalent bond between the two or more amino acid residues is an amide bond. However, the amino acids can be joined together by various other means known to those skilled in the peptide and chemical arts. Therefore, a polypeptide, in whole or in part, can include molecules which contain non-amide linkages between amino acids, amino acid analogs, and mimetics. Similarly, the term also includes cyclic peptides and other conformationally constrained structures. A polypeptide also can be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like.

As described below, polypeptides of the invention also encompass, for example, modified forms of naturally occurring amino acids such as D-stereoisomers, non-naturally occurring amino acids, amino acid analogues and mimetics so long as such variants have substantially the same amino acid sequence as the reference butyrylcholinesterase variant polypeptide and exhibit about the same cocaine hydrolysis activity. A butyrylcholinesterase variant polypeptide of the invention can have two or more amino acid alterations. Furthermore, a butyrylcholinesterase variant polypeptide of the invention can have one or more additional modifications that do not significantly change its cocaine hydrolysis activity, but confer a desirable property such as increased biostability.

It is understood that the amino acid sequences of the invention can have a similar, non-identical sequence, and retaining comparable functional and biological activity of the polypeptide defined by the reference amino acid sequence. A variant polypeptide of the invention encompasses substantially similar amino acid sequences that can have at least about 75%, 80%, 82%, 84%, 86% or 88%, or at least 90%, 91%, 92%, 93% or 94% amino acid identity with respect to the reference amino acid sequence; as well as greater than 95%, 96%, 97%, 98% or 99% amino acid identity as long as such polypeptides retain a biological activity of the reference butyrylcholinesterase variant polypeptide. It is recognized, however, that polypeptides, or encoding nucleic acids, containing less than the described levels of sequence identity arising as splice variants or that are modified by conservative amino acid substitutions, or by substitution of degenerate codons also are encompassed within the scope of the present invention.

A biological activity of a butyrylcholinesterase variant of the invention is cocaine hydrolysis activity as described herein. For example, the butyrylcholinesterase variant A328W/Y332M designated SEQ ID NO: 2 exhibits about a twenty-four-fold increased cocaine hydrolysis activity compared to butyrylcholinesterase; the butyrylcholinesterase variant A328W/Y332P designated SEQ ID NO: 4 exhibits about a ten-fold increased cocaine hydrolysis activity compared to butyrylcholinesterase; the butyrylcholinesterase variant A328W/V331L designated SEQ ID NO: 6 exhibits about a sixteen-fold increased cocaine hydrolysis activity compared to butyrylcholinesterase; the butyrylcholinesterase variant A328W/Y332S designated SEQ ID NO: 8 exhibits about a seven-fold increased cocaine hydrolysis activity compared to butyrylcholinesterase; the butyrylcholinesterase variant A328W/Y332M/S287G/F227A/A199S designated SEQ ID NO: 10 exhibits about a one-hundred-fold increased cocaine hydrolysis activity compared to butyrylcholinesterase; the butyrylcholinesterase variant A328W/S287G/F227A/A199S designated SEQ ID NO: 12 exhibits about a one-hundred-fold increased cocaine hydrolysis activity compared to butyrylcholinesterase; the butyrylcholinesterase variant A328W/S287G/A199S designated SEQ ID NO: 14 exhibits about a ninety-seven-fold increased cocaine hydrolysis activity compared to butyrylcholinesterase; the butyrylcholinesterase variant A328W/S287G/F227A designated SEQ ID NO: 16 exhibits about a ninety-one-fold increased cocaine hydrolysis activity compared to butyrylcholinesterase; the butyrylcholinesterase variant A328W/F227A designated SEQ ID NO: 18 exhibits about a sixty-eight-fold increased cocaine hydrolysis activity compared to butyrylcholinesterase; the butyrylcholinesterase variant Y332S designated SEQ ID NO: 20 exhibits an increased cocaine hydrolysis activity compared to butyrylcholinesterase; the butyrylcholinesterase variant Y332M designated SEQ ID NO: 22 exhibits an increased cocaine hydrolysis activity compared to butyrylcholinesterase; the butyrylcholinesterase variant Y332P designated SEQ ID NO: 24 exhibits an increased cocaine hydrolysis activity compared to butyrylcholinesterase; the butyrylcholinesterase variant V331L designated SEQ ID NO: 26 exhibits an increased cocaine hydrolysis activity compared to butyrylcholinesterase; the butyrylcholinesterase variant F227A designated SEQ ID NO: 28 exhibits about a four-fold increased cocaine hydrolysis activity compared to butyrylcholinesterase; the butyrylcholinesterase variant F227G designated SEQ ID NO: 30 exhibits about a four-fold increased cocaine hydrolysis activity compared to butyrylcholinesterase; the butyrylcholinesterase variant F227S designated SEQ ID NO: 32 exhibits about a two-fold increased cocaine hydrolysis activity compared to butyrylcholinesterase; the butyrylcholinesterase variant F227P designated SEQ ID NO: 34 exhibits about a three-fold increased cocaine hydrolysis activity compared to butyrylcholinesterase; the butyrylcholinesterase variant F227T designated SEQ ID NO: 36 exhibits about a two-fold increased cocaine hydrolysis activity compared to butyrylcholinesterase; the butyrylcholinesterase variant F227C designated SEQ ID NO: 38 exhibits about a two-fold increased cocaine hydrolysis activity compared to butyrylcholinesterase; the butyrylcholinesterase variant F227M designated SEQ ID NO: 40 exhibits about a one-and-a-half-fold increased cocaine hydrolysis activity compared to butyrylcholinesterase; the butyrylcholinesterase variant A199S designated SEQ ID NO: 42 exhibits about a two-and-a-half-fold increased cocaine hydrolysis activity compared to butyrylcholinesterase; and the butyrylcholinesterase variant A328W/Y332M/S287G/F227A designated SEQ ID NO: 52, also referred to as AME-359 herein, exhibits about a one-hundred-fold increased cocaine hydrolysis activity compared to butyrylcholinesterase.

One skilled in the art will appreciate that the exact increase in cocaine hydrolysis activity compared to butyrylcholinesterase that is detected depends on the particular assay chosen. Therefore, while all of the butyrylcholinesterase variants of the invention have increased cocaine hydrolysis activity, the values set forth herein are approximate values that can vary if a different assay were performed.

It is understood that minor modifications in the primary amino acid sequence can result in a polypeptide that has a similar, non-identical sequence, but retains comparable functional or biological activity to a butyrylcholinesterase variant polypeptide of the invention. These modifications can be deliberate, as through site-directed mutagenesis, or may be accidental such as through spontaneous mutation. For example, it is understood that only a portion of the entire primary structure of a butyrylcholinesterase variant polypeptide can retain the cocaine hydrolysis activity of the reference butyrylcholinesterase variant polypeptide. Such functional fragments of the sequence of a butyrylcholinesterase variant polypeptide of the invention are included within the definition as long as at least one biological function of the butyrylcholinesterase variant is retained. It is understood that various molecules can be attached to a polypeptide of the invention, for example, other polypeptides, carbohydrates, lipids, or chemical moieties.

The term "functional fragment," when used in reference to a butyrylcholinesterase variant polypeptide of the invention, refers to a polypeptide fragment that is a portion of the butyrylcholinesterase variant polypeptide, provided that the portion has a biological activity, as described herein, that is characteristic of the reference butyrylcholinesterase variant polypeptide. The amino acid length of a functional fragment of a butyrylcholinesterase variant polypeptide of the present invention can range from about 5 amino acids up to the full-length protein sequence of the reference butyrylcholinesterase variant polypeptide. In certain embodiments, the amino acid lengths include, for example, at least about 10 amino acids, at least about 15, at least about 20, at least about 25, at least about 30, at least about 35, at least about 40, at least about 45, at least about 50, at least about 75, at least about 100, at least about 150, at least about 200, at least about 250 or more amino acids in length up to the full-length butyrylcholinesterase variant polypeptide sequence. The functional fragments can be contiguous amino acid sequences of a butyrylcholinesterase variant polypeptide, including contiguous amino acid sequence corresponding to the substrate binding domain of the butyrylcholinesterase variant polypeptide. A functional fragment of a butyrylcholinesterase variant polypeptide of the invention exhibiting a functional activity can have, for example, at least 8, 10, 15, 20, 30 or 40 amino acids, and often has at least 50, 75, 100, 200, 300, 400 or more amino acids of a polypeptide of the invention, up to the full length polypeptide minus one amino acid. The appropriate length and amino acid sequence of a functional fragment of a polypeptide of the invention can be determined by those skilled in the art, depending on the intended use of the functional fragment. For example, a functional fragment of a butyrylcholinesterase variant is intended to refer to a portion of the butyrylcholinesterase variant that still retains some or all of the cocaine hydrolysis activity of the parent polypeptide.

A functional fragment of a butyrylcholinesterase variant polypeptide can contain active site residues important for the catalytic activity of the enzyme. Regions important for the hydrolysis activity of a butyrylcholinesterase variant polypeptide can be determined or predicted through a variety of methods known in the art. Related enzymes such as, for example, acetylcholinesterase and carboxylesterase, that share a high degree of sequence similarity and have biochemically similar catalytic properties can provide information regarding the regions important for catalytic activity of a butyrylcholinesterase variant polypeptide. For example, structural modeling can reveal the active site of an enzyme, which is a three-dimensional structure such as a cleft, gorge or crevice formed by amino acid residues generally located apart from each other in primary structure. Therefore, a functional fragment of a butyrylcholinesterase variant polypeptide of the invention can encompass amino acid residues that make up regions of a butyrylcholinesterase enzyme important for cocaine hydrolysis activity such as those residues located along the active site gorge.

In addition to structural modeling of a butyrylcholinesterase enzyme, biochemical data can be used to determine or predict regions of a butyrylcholinesterase variant polypeptide important for cocaine hydrolysis activity when preparing a functional fragment of a butyrylcholinesterase variant polypeptide of the invention. In this regard, the characterization of naturally occurring butyrylcholinesterase enzymes with altered cocaine hydrolysis activity can be useful for identifying regions important for the catalytic activity of a butyrylcholinesterase variant polypeptide. Similarly, site-directed mutagenesis studies can provide data regarding catalytically important amino acid residues as reviewed, for example, in Schwartz et al., *Pharmac. Ther.* 67: 283–322 (1992), which is incorporated by reference. In particular, a functional fragment of a butyrylcholinesterase variant polypeptide can include the active site residues corresponding to amino acid positions 82, 112, 128, 231, 329, 332, 430 and 440 of the butyrylcholinesterase shown as SEQ ID NO: 14. Thus, a functional fragment can, for example, be 360 amino acid residues in length and can include residues 80 to 440 of the reference butyrylcholinesterase variant polypeptide.

Therefore, a functional fragment of a butyrylcholinesterase variant polypeptide can encompass an area or region of the amino acid sequence of butyrylcholinesterase that is determined or predicted to be important for cocaine hydrolysis activity. As described above, a region can be determined or predicted to be important for cocaine hydrolysis activity by using one or more of structural, biochemical or modeling methods and, as a consequence, is defined by general rather than absolute boundaries. A region can encompass two or more consecutive amino acid positions of the amino acid sequence of butyrylcholinesterase that are predicted to be important for cocaine hydrolysis activity. A region of butyrylcholinesterase useful as a functional fragment of a butyrylcholinesterase variant polypeptide for practicing the claimed invention is no more than about 30 amino acids in length and preferably is between 2 and 20, between 5 and 15 amino acids in length.

A butyrylcholinesterase variant polypeptide of the invention, or a functional fragment thereof, can have conservative amino acid substitutions as compared with the reference butyrylcholinesterase variant amino acid sequence. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His).

A butyrylcholinesterase variant polypeptide having the same or substantially the same amino acid sequence of SEQ ID NOS: 2, 4, 6, 8, 10, 12, 14, 16, 18, 20, 22, 24, 26, 28, 30, 32, 34, 36, 38, 40, 42 and 52, or a functional fragment thereof, also can be chemically modified, provided that the polypeptide retains a biological activity of the reference butyrylcholinesterase variant polypeptide. For example, chemical modification of a butyrylcholinesterase variant polypeptide of the invention can include alkylation, acylation, carbamylation and iodination. Moreover, modified polypeptides also can include those polypeptides in which free amino groups have been derivatized to form, for example, amine hydrochlorides, p-toluene sulfonyl groups, carbobenzoxy groups, t-butyloxycarbonyl groups, chloroacetyl groups or formyl groups. Free carboxyl groups can be modified to form salts, methyl and ethyl esters or other types of esters or hydrazides. Free hydroxyl groups can be modified to form O-acyl or O-alkyl, derivatives. The imidazole nitrogen of histidine can be derivatized to form N-im-benzylhistidine. A butyrylcholinesterase variant polypeptide of the invention also can include a variety of other modifications well known to those skilled in the art, provided the biological activity of the reference butyrylcholinesterase variant polypeptide remains substantially unaffected.

An isolated polypeptide having the same or substantially the same amino acid sequence of SEQ ID NOS: 2, 4, 6, 8, 10, 12, 14, 16, 18, 20, 22, 24, 26, 28, 30, 32, 34, 36, 38, 40, 42 or 52, or a functional fragment thereof, also can be substituted with one or more amino acid analogs of the twenty standard amino acids, for example, 4-hydroxyproline, 5-hydroxylysine, 3-methylhistidine, homoserine, ornithine or carboxyglutamate, and can include amino acids that are not linked by peptide bonds.

A butyrylcholinesterase variant polypeptide having the same or substantially the same amino acid sequence of SEQ ID NOS: 2, 4, 6, 8, 10, 12, 14, 16, 18, 20, 22, 24, 26, 28, 30, 32, 34, 36, 38, 40, 42 or 52, or a functional fragment thereof, also can contain mimetic portions that orient functional groups, which provide a function of a butyrylcholinesterase enzyme. Therefore, mimetics encompass chemicals containing chemical moieties that mimic the function of the polypeptide. For example, if a polypeptide contains similarly charged chemical moieties having similar functional activity, a mimetic places similar charged chemical moieties in a similar spatial orientation and constrained structure so that the chemical function of the charged moieties is maintained. Exemplary mimetics are peptidomimetics, peptoids, or other peptide-like polymers such as poly-β-amino acids, and also non-polymeric compounds upon which functional groups that mimic a peptide are positioned.

A butyrylcholinesterase variant of the invention can be prepared by a variety of methods well known in the art. If desired, random mutagenesis can be performed to prepare a butyrylcholinesterase variant of the invention. Alternatively, as disclosed herein, site-directed mutagenesis based on the information obtained from structural, biochemical and modeling methods described herein can be performed to target those amino acids predicted to be important for cocaine hydrolysis activity. For example, molecular modeling of cocaine in the active site of butyrylcholinesterase can be utilized to predict amino acid alterations that allow for higher catalytic efficiency based on a better fit between the enzyme and its substrate. As described herein, residues predicted to be important for cocaine hydrolysis activity include 8 hydrophobic gorge residues and the catalytic triad residues. Furthermore, it is understood that amino acid alterations of residues important for the functional structure of a butyrylcholinesterase variant, which include the cysteine residues $^{65}$Cys-$^{92}$Cys, $^{252}$Cys-$^{263}$Cys, and $^{400}$Cys-$^{519}$Cys involved in intrachain disulfide bonds are generally not altered in the preparation of a butyrylcholinesterase variant that has cocaine hydrolysis activity.

Following mutagenesis of butyrylcholinesterase or a butyrylcholinesterase variant expression, purification and functional characterization of the butyrylcholinesterase variant can be performed by methods well known in the art. As disclosed below, a butyrylcholinesterase variant can be expressed in an appropriate host cell line and subsequently purified and characterized for cocaine hydrolysis activity. Butyrylcholinesterase variants characterized as having significantly increased cocaine hydrolysis activity can subsequently be used in the methods of hydrolyzing a cocaine-based substrate as well as the methods of treating a cocaine-induced condition described below.

A butyrylcholinesterase variant of the invention exhibits cocaine hydrolysis activity. As disclosed herein, a butyrylcholinesterase variant of the invention can have increased cocaine hydrolysis activity compared to butyrylcholinesterase and can be used to treat a cocaine-induced condition. A polypeptide having minor modifications compared to a butyrylcholinesterase variant of the invention is encompassed by the invention so long as equivalent cocaine hydrolysis activity is retained. In addition, functional fragments of a butyrylcholinesterase variant that still retain some or all of the cocaine hydrolysis activity of the parent butyrylcholinesterase variant are similarly included in the invention. Similarly, functional fragments of nucleic acids, which encode functional fragments of a butyrylcholinesterase variant of the invention are similarly encompassed by the invention.

A functional fragment of a butyrylcholinesterase variant of the invention can be prepared by recombinant methods involving expression of a nucleic acid molecule encoding the butyrylcholinesterase variant or functional fragment thereof, followed by isolation of the variant or functional fragment thereof by routine biochemical methods described herein. It is understood that functional fragments also can be prepared by enzymatic or chemical cleavage of the full length butyrylcholinesterase variant. Methods for enzymatic and chemical cleavage and for purification of the resultant peptide fragments are well known in the art (see, for example, Deutscher, *Methods in Enzymology*, Vol. 182, "Guide to Protein Purification," San Diego: Academic Press, Inc. (1990), which is incorporated herein by reference).

Furthermore, functional fragments of a butyrylcholinesterase variant can be produced by chemical synthesis. If desired, such molecules can be modified to include D-stereoisomers, non-naturally occurring amino acids, and amino acid analogs and mimetics in order to optimize their functional activity, stability or bioavailability.) Examples of modified amino acids and their uses are presented in Sawyer, *Peptide Based Drug Design*, ACS, Washington (1995) and Gross and Meienhofer, *The Peptides: Analysis, Synthesis, Biology*, Academic Press, Inc., New York (1983), both of which are incorporated herein by reference.

If desired, random segments of a butyrylcholinesterase variant can be prepared and tested in the assays described herein. A fragment having any desired boundaries and modifications compared to the amino acid sequence of the reference butyrylcholinesterase variant of the invention can be prepared. Alternatively, available information obtained by the structural, biochemical and modeling methods described herein can be used to prepare only those fragments of a butyrylcholinesterase variant that are likely to retain the cocaine hydrolysis activity of the parent variant. As described herein, residues predicted to be important for cocaine hydrolysis activity include 8 hydrophobic gorge residues and the catalytic triad residues. Furthermore, residues important for the functional structure of a butyrylcholinesterase variant include the cysteine residues $^{65}$Cys-$^{92}$Cys, $^{252}$Cys-263Cys, and $^{400}$Cys-$^{519}$Cys involved in intrachain disulfide bonds. Therefore, a functional fragment can be a truncated form, region or segment of the reference butyrylcholinesterase variant designed to possess most or all of the residues critical for cocaine hydrolysis activity or functional structure so as to retain equivalent cocaine hydrolysis activity. Similarly, a functional fragment can include non-peptidic structural elements that serve to mimic structurally or functionally important residues of the reference variant. Also included as butyrylcholinesterase variants of the invention are fusion proteins that result from linking a butyrylcholinesterase variant or functional fragment thereof to a heterologous protein, such as a therapeutic protein, as well as fusion constructs of nucleic acids encoding such fusion proteins. Fragments of nucleic acids that can hybridize to a butyrylcholinesterase variant or functional fragment thereof are useful, for example, as hybridization probes and are also encompassed by the claimed invention.

Thus, the invention provides twenty-one butyrylcholinesterase variants encompassing the same or substantially the same amino acid sequences shown as SEQ ID NOS: 2, 4, 6, 8, 10, 12, 14, 16, 18, 20, 22, 24, 26, 28, 30, 32, 34, 36, 38, 40, 42 and 52, and functional fragments thereof. As described herein, each of the invention butyrylcholinesterase variants exhibits about an increased cocaine hydrolysis activity compared to butyrylcholinesterase.

The invention also provides twenty-one nucleic acids shown as SEQ ID NOS: 1, 3, 5, 7, 9, 11, 13, 15, 17, 19, 21, 23, 25, 27, 29, 31, 33, 35, 37, 39, 41 and 51, respectively, and fragments thereof, which encode the butyrylcholinesterase variants encompassing the same or substantially the same amino acid sequences shown as SEQ ID NOS: 2, 4, 6, 8, 10, 12, 14, 16, 18, 20, 22, 24, 26, 28, 30, 32, 34, 36, 38, 40, 42 and 52, respectively. Thus, the present invention provides nucleic acids that encode a butyrylcholinesterase variant encompassing the same or substantially the same amino acid sequences shown as SEQ ID NOS: 2, 4, 6, 8, 10, 12, 14, 16, 18, 20, 22, 24, 26, 28, 30, 32, 34, 36, 38, 40, 42 and 52.

It is understood that a nucleic acid molecule of the invention or a fragment thereof includes sequences having one or more additions, deletions or substitutions with respect to the reference sequence, so long as the nucleic acid molecule retains its ability to selectively hybridize with the subject nucleic acid molecule under moderately stringent conditions, or highly stringent conditions. Moderately stringent conditions are hybridization conditions equivalent to hybridization of filter-bound nucleic acid in 50% formamide, 5× Denhardt's solution, 5×SSPE, 0.2% SDS at 42° C., followed by washing in 0.2×SSPE, 0.2% SDS, at 50°. Highly stringent conditions refers to conditions equivalent to hybridization of filter-bound nucleic acid in 50% formamide, 5× Denhardt's solution, 5×SSPE, 0.2% SDS at 42° C., followed by washing in 0.2×SSPE, 0.2% SDS, at 65°. Other suitable moderately stringent and highly stringent hybridization buffers and conditions are well known to those of skill in the art and are described, for example, in Sambrook et al., *Molecular Cloning: A Laboratory Manual,* 2nd ed., Cold Spring Harbor Press, Plainview, N.Y. (1989); and Ausubel et al., *Current Protocols in Molecular Biology*, John Wiley & Sons, New York (2000). Thus, it is not necessary that two nucleic acids exhibit sequence identity to be substantially complementary, only that they can specifically hybridize or be made to specifically hybridize without detectible cross reactivity with other similar sequences.

In general, a nucleic acid molecule that has substantially the same nucleotide sequence as a reference sequence will have greater than about 60% identity, such as greater than about 65%, 70%, 75% identity with the reference sequence, such as greater than about 80%, 85%, 90%, 95%, 97% or 99% identity to the reference sequence over the length of the two sequences being compared. Identity of any two nucleic acid sequences can be determined by those skilled in the art based, for example, on a BLAST 2.0 computer alignment, using default parameters. BLAST 2.0 searching is available at ncbi.nlm.nih.gov/gorf/bl2.html., as described by Tatiana et al., *FEMS Microbiol Lett.* 174:247–250 (1999).

As used herein, the term "fragment" when used in reference to a nucleic acid encoding the claimed polypeptides is intended to mean a nucleic acid having substantially the same sequence as a portion of a nucleic acid encoding a polypeptide of the invention or segments thereof. The nucleic acid fragment is sufficient in length and sequence to selectively hybridize to a butyrylcholinesterase variant encoding nucleic acid or a nucleotide sequence that is complementary to a butyrylcholinesterase variant encoding nucleic acid. Therefore, fragment is intended to include primers for sequencing and polymerase chain reaction (PCR) as well as probes for nucleic acid blot or solution hybridization.

Similarly, the term "functional fragment" when used in reference to a nucleic acid encoding a butyrylcholinesterase or butyrylcholinesterase variant is intended to refer to a portion of the nucleic acid that encodes a portion of the butyrylcholinesterase variant that still retains some or all of the cocaine hydrolysis activity of the reference variant polypeptide. A functional fragment of a polypeptide of the invention exhibiting a functional activity can have, for example, at least 6 contiguous amino acid residues from the polypeptide, at least 8, 10, 15, 20, 30 or 40 amino acids, and often has at least 50, 75, 100, 200, 300, 400 or more amino acids of a polypeptide of the invention, up to the full length polypeptide minus one amino acid.

As used herein, the term "cocaine hydrolysis activity," is intended to refer to the catalytic action of a butyrylcholinesterase or butyrylcholinesterase variant as measured by the rate of cocaine hydrolysis into the metabolites.

As used herein, the term "effective amount" is intended to mean an amount of a butyrylcholinesterase variant of the invention that can reduce the cocaine-toxicity or the severity of a cocaine-induced condition. Reduction in severity includes, for example, an arrest or a decrease in symptoms, physiological indicators, biochemical markers or metabolic indicators. Symptoms of cocaine overdose include, for example, cardiac arrythmias, seizures and hypertensive crises. A reduction in severity also includes a delay in the onset of symptoms. As used herein, the term "treating" is intended to mean causing a reduction in the severity of a cocaine-induced condition.

As used herein, the term "cocaine-based substrate" refers to (−)-cocaine or any molecule sufficiently similar to (−)-cocaine in structure to be hydrolyzed by butyrylcholinesterase or a butyrylcholinesterase variant including, for example, (+)-cocaine, acetylcholine, butyrylthiocholine, benzoylcocaine and norcocaine.

The nucleic acid shown as SEQ ID NO: 1, or fragment thereof, encodes a butyrylcholinesterase variant encompassing the same or substantially the same amino acid sequence shown as SEQ ID NO: 2. As shown in Table 1, the nucleic acid shown as SEQ ID: 1 differs from the nucleic acid encoding human butyrylcholinesterase shown in FIG. 3 at the codon positions encoding amino acid residues 328 and 332, respectively. In the human butyrylcholinesterase (SEQ ID NO: 13) the codons gct and tat encode Alanine at amino acid position 328 and Tyrosine at amino acid position 332, respectively. In contrast, in the nucleic acid encoding the A328W/Y332M butyrylcholinesterase variant designated SEQ ID NO: 2, the codons tgg and atg encode Tryptophan at amino acid position 328 and Methionine at amino acid position 332, respectively.

The invention provides a further nucleic acid shown as SEQ ID NO: 3, or fragment thereof, encodes a butyrylcholinesterase variant encompassing the same or substantially the same amino acid sequence shown as SEQ ID NO: 4. As shown in Table 1, the nucleic acid shown as SEQ ID: 3 differs from the nucleic acid encoding human butyrylcholinesterase shown in FIG. 3 and designated SEQ ID NO: 13, at the codons encoding amino acid residues 328 and 332. In the human butyrylcholinesterase (SEQ ID NO: 13) the codons gct and tat encode Alanine at amino acid position 328 and Tyrosine at amino acid position 332. In contrast, in the nucleic acid encoding the A328W/Y332P butyrylcholinesterase variant designated SEQ ID NO: 4, the codons tgg and cca encode Tryptophan at amino acid position 328 and Proline at amino acid position 332.

The invention provides a further nucleic acid shown as SEQ ID NO: 5, or fragment thereof, encodes a butyrylcholinesterase variant encompassing the same or substantially the same amino acid sequence shown as SEQ ID NO: 6. As shown in Table 1, the nucleic acid shown as SEQ ID: 5 differs from the nucleic acid encoding human butyrylcholinesterase shown in FIG. 3 and designated SEQ ID NO: 43, at the codon positions encoding amino acid residues 328 and 331. In the human butyrylcholinesterase (SEQ ID NO: 43) the codons gct and gtc encode Alanine at amino acid position 328 and Valine at amino acid position 331. In contrast, in the nucleic acid encoding the A328W/V331L butyrylcholinesterase variant designated SEQ ID NO: 6, the corresponding codons encode Tryptophan at amino acid position 328 and Leucine at amino acid position 331.

The invention provides a further nucleic acid shown as SEQ ID NO: 7, or fragment thereof, encodes a butyrylcholinesterase variant encompassing the same or substantially the same amino acid sequence shown as SEQ ID NO: 8. As shown in Table 1, the nucleic acid shown as SEQ ID: 7 differs from the nucleic acid encoding human butyrylcholinesterase shown in FIG. 3 and designated SEQ ID NO: 43 at the codon positions encoding amino acid residues 328 and 332. In the human butyrylcholinesterase (SEQ ID NO: 43) the codons gct and tat encode Alanine at amino acid position 328 and Tyrosine at amino acid position 332. In contrast, in the nucleic acid encoding the A328W/Y332S butyrylcholinesterase variant designated SEQ ID NO: 8, the codons tgg and tcg encode Tryptophan at amino acid position 328 and Serine at amino acid position 332.

The invention provides a further nucleic acid shown as SEQ ID NO: 9, or fragment thereof, which encodes a butyrylcholinesterase variant encompassing the same or substantially the same amino acid sequence shown as SEQ ID NO: 10. As shown in Table 1, the nucleic acid shown as SEQ ID: 9 differs from the nucleic acid encoding human butyrylcholinesterase shown in FIG. 3 and designated SEQ ID NO: 43, at the codon positions encoding amino acid residues 199, 227, 287, 332 and 328. In the human butyrylcholinesterase (SEQ ID NO: 43) the codons gca, ttt, tca, gct and tat encode Alanine at amino acid position 199, Phenylalanine at amino acid position 227, Serine at amino acid position 287, Alanine at amino acid position 328 and Tyrosine at amino acid position 332. In contrast, in the nucleic acid encoding the A328W/Y332M/S287G/F227A/

A199S butyrylcholinesterase variant designated SEQ ID NO: 10, the codons tca, gcg, ggt, tgg and atg encode Serine at amino acid position 199, Alanine at amino acid position 227, Glycine at amino acid position 287, Tryptophan at amino acid position 328 and Methionine at amino acid position 332, respectively.

The invention provides a further nucleic acid shown as SEQ ID NO: 11, or fragment thereof, encodes a butyrylcholinesterase variant encompassing the same or substantially the same amino acid sequence shown as SEQ ID NO: 12. As shown in Table 1, the nucleic acid shown as SEQ ID: 11 differs from the nucleic acid encoding human butyrylcholinesterase shown in FIG. 3 and designated SEQ ID NO: 43, at the codon positions encoding amino acid residues 199, 227, 287 and 328, respectively. In the human butyrylcholinesterase (SEQ ID NO: 43) the codons gca, ttt, tca and gct encode Alanine at amino acid position 199, Phenylalanine at amino acid position 227, Serine at amino acid position 287, and Alanine at amino acid position 328, respectively. In contrast, in the nucleic acid encoding the A328W/S287G/F227A/A199S butyrylcholinesterase variant designated SEQ ID NO: 12, the codons tca, gcg, ggt and tgg encode Serine at amino acid position 199, Alanine at amino acid position 227, Glycine at amino acid position 287 and Tryptophan at amino acid position 328, respectively.

The invention provides a further nucleic acid shown as SEQ ID NO: 13, or fragment thereof, which encodes a butyrylcholinesterase variant encompassing the same or substantially the same amino acid sequence shown as SEQ ID NO: 14. As shown in Table 1, the nucleic acid shown as SEQ ID: 13 differs from the nucleic acid encoding human butyrylcholinesterase shown in FIG. 3 and designated SEQ ID NO: 43, at the codon positions encoding amino acid residues 199, 287 and 328, respectively. In the human butyrylcholinesterase (SEQ ID NO: 43) the codons gca, tca and gct encode Alanine at amino acid position 199, Serine at amino acid position 287 and Alanine at amino acid position 328, respectively. In contrast, in the nucleic acid encoding the A328W/S287G/A199S butyrylcholinesterase variant designated SEQ ID NO: 14, the codons tca, ggt and tgg, encode Serine at amino acid position 199, Glycine at amino acid position 287 and Tryptophan at amino acid position 328, respectively.

The invention provides a further nucleic acid shown as SEQ ID NO: 15, or fragment thereof, which encodes a butyrylcholinesterase variant encompassing the same or substantially the same amino acid sequence shown as SEQ ID NO: 16. As shown in Table 1, the nucleic acid shown as SEQ ID: 15 differs from the nucleic acid encoding human butyrylcholinesterase shown in FIG. 3 and designated SEQ ID NO: 43, at the codon positions encoding amino acid residues 227, 287 and 328, respectively. In the human butyrylcholinesterase (SEQ ID NO: 43) the codons ttt, tca, gct encode Phenylalanine at amino acid position 227, Serine at amino acid position 287 and Alanine at amino acid position 328, respectively. In contrast, in the nucleic acid encoding the A328W/S287G/F227A butyrylcholinesterase variant designated SEQ ID NO: 16, the codons gcg, ggt and tgg encode Alanine at amino acid position 227, Glycine at amino acid position 287 and Tryptophan at amino acid position 328, respectively.

The invention provides a further nucleic acid shown as SEQ ID NO: 17, or fragment thereof, which encodes a butyrylcholinesterase variant encompassing the same or substantially the same amino acid sequence shown as SEQ ID NO: 18. As shown in Table 1, the nucleic acid shown as SEQ ID: 17 differs from the nucleic acid encoding human butyrylcholinesterase shown in FIG. 3 and designated SEQ ID NO: 43, at the codon positions encoding amino acid residues 227 and 328, respectively. In the human butyrylcholinesterase (SEQ ID NO: 43) the codons ttt and gct at nucleotide encode Phenylalanine at amino acid position 227 and Alanine at amino acid position 328, respectively. In contrast, in the nucleic acid encoding the A328W/F227A butyrylcholinesterase variant designated SEQ ID NO: 18, the codons gcg and tgg encode Alanine at amino acid position 227 and Tryptophan at amino acid position 328, respectively.

The invention provides a further nucleic acid shown as SEQ ID NO: 19, or fragment thereof, which encodes a butyrylcholinesterase variant comprising substantially the same amino acid sequence shown as SEQ ID NO: 20. As shown in Table 1, the nucleic acid shown as SEQ ID: 19 differs from the nucleic acid encoding human butyrylcholinesterase shown in FIG. 3 and designated SEQ ID NO: 43, at the codon position encoding amino acid residue 332. In the human butyrylcholinesterase (SEQ ID NO: 43) the codon tat encodes Tyrosine at amino acid position 332. In contrast, in the nucleic acid encoding the Y332S butyrylcholinesterase variant designated SEQ ID NO: 20, the codon tcg encodes Serine at amino acid position 332.

The invention provides a further nucleic acid shown as SEQ ID NO: 21, or fragment thereof, which encodes a butyrylcholinesterase variant encompassing the same or substantially the same amino acid sequence shown as SEQ ID NO: 22. As shown in Table 1, the nucleic acid shown as SEQ ID: 21 differs from the nucleic acid encoding human butyrylcholinesterase shown in FIG. 3 and designated SEQ ID NO: 43, at the codon position encoding amino acid residue 332. In the human butyrylcholinesterase (SEQ ID NO: 43) the codon tat encodes Tyrosine at amino acid position 332. In contrast, in the nucleic acid encoding the Y332M butyrylcholinesterase variant designated SEQ ID NO: 22, the codon atg encodes Methionine at amino acid position 332.

The invention provides a further nucleic acid shown as SEQ ID NO: 23, or fragment thereof, which encodes a butyrylcholinesterase variant encompassing the same or substantially the same amino acid sequence shown as SEQ ID NO: 24. As shown in Table 1, the nucleic acid shown as SEQ ID: 23 differs from the nucleic acid encoding human butyrylcholinesterase shown in FIG. 3 and designated SEQ ID NO: 43, at the codon position encoding amino acid residue 332. In the human butyrylcholinesterase (SEQ ID NO: 43) the codon tat encodes Tyrosine at amino acid position 332. In contrast, in the nucleic acid encoding the Y332P butyrylcholinesterase variant designated SEQ ID NO: 24, the codon cca encodes Proline at amino acid position 332.

The invention provides a further nucleic acid shown as SEQ ID NO: 25, or fragment thereof, which encodes a butyrylcholinesterase variant encompassing the same or substantially the same amino acid sequence shown as SEQ ID NO: 26. As shown in Table 1, the nucleic acid shown as SEQ ID: 25 differs from the nucleic acid encoding human butyrylcholinesterase shown in FIG. 3 and designated SEQ ID NO: 43, at the codon position encoding amino acid residue 331. In the human butyrylcholinesterase (SEQ ID NO: 43) the codon gtc encodes Valine at amino acid position 331. In contrast, in the nucleic acid encoding the V331L butyrylcholinesterase variant designated SEQ ID NO: 26, the codon ttg encodes Leucine at amino acid position 331.

The invention provides a further nucleic acid shown as SEQ ID NO: 27, or fragment thereof, which encodes a butyrylcholinesterase variant encompassing the same or substantially the same amino acid sequence shown as SEQ ID NO: 28. As shown in Table 1, the nucleic acid shown as SEQ ID: 27 differs from the nucleic acid encoding human butyrylcholinesterase shown in FIG. 3 and designated SEQ ID NO: 43, at the codon position encoding amino acid residue 227. In the human butyrylcholinesterase (SEQ ID NO: 43) the codon ttt encodes Phenylalanine at amino acid position 227. In contrast, in the nucleic acid encoding the F227A butyrylcholinesterase variant designated SEQ ID NO: 28, the codon gcg encodes Alanine at amino acid position 227.

The invention provides a further nucleic acid shown as SEQ ID NO: 29, or fragment thereof, which encodes a butyrylcholinesterase variant encompassing the same or substantially the same amino acid sequence shown as SEQ ID NO: 30. As shown in Table 1, the nucleic acid shown as SEQ ID: 29 differs from the nucleic acid encoding human butyrylcholinesterase shown in FIG. 3 and designated SEQ ID NO: 43, at the codon position encoding amino acid residue 227. In the human butyrylcholinesterase (SEQ ID NO: 43) the codon ttt encodes Phenylalanine at amino acid position 227. In contrast, in the nucleic acid encoding the F227G butyrylcholinesterase variant designated SEQ ID NO: 30, the codon ggg encodes Glycine at amino acid position 227.

The invention provides a further nucleic acid shown as SEQ ID NO: 31, or fragment thereof, which encodes a butyrylcholinesterase variant encompassing the same or substantially the same amino acid sequence shown as SEQ ID NO: 32. As shown in Table 1, the nucleic acid shown as SEQ ID: 31 differs from the nucleic acid encoding human butyrylcholinesterase shown in FIG. 3 and designated SEQ ID NO: 43, at the codon position encoding amino acid residues 227. In the human butyrylcholinesterase (SEQ ID NO: 43) the codon ttt encodes Phenylalanine at amino acid position 227. In contrast, in the nucleic acid encoding the F227S butyrylcholinesterase variant designated SEQ ID NO: 32, the codon agt encodes Serine at amino acid position 227.

The invention provides a further nucleic acid shown as SEQ ID NO: 33, or fragment thereof, which encodes a butyrylcholinesterase variant encompassing the same or substantially the same amino acid sequence shown as SEQ ID NO: 34. As shown in Table 1, the nucleic acid shown as SEQ ID: 33 differs from the nucleic acid encoding human butyrylcholinesterase shown in FIG. 3 and designated SEQ ID NO: 43, at the codon position encoding amino acid residues 227. In the human butyrylcholinesterase (SEQ ID NO: 43) the codon ttt encodes Phenylalanine at amino acid position 227. In contrast, in the nucleic acid encoding the F227P butyrylcholinesterase variant designated SEQ ID NO: 34, the codon ccg encodes Proline at amino acid position 227.

The invention provides a further nucleic acid shown as SEQ ID NO: 35, or fragment thereof, which encodes a butyrylcholinesterase variant encompassing the same or substantially the same amino acid sequence shown as SEQ ID NO: 36. As shown in Table 1, the nucleic acid shown as SEQ ID: 35 differs from the nucleic acid encoding human butyrylcholinesterase shown in FIG. 3 and designated SEQ ID NO: 43, at the codon position encoding amino acid residue 227. In the human butyrylcholinesterase (SEQ ID NO: 43) the codon ttt encodes Phenylalanine at amino acid position 227. In contrast, in the nucleic acid encoding the F227T butyrylcholinesterase variant designated SEQ ID NO: 36, the codon act encodes Threonine at amino acid position 227.

The invention provides a further nucleic acid shown as SEQ ID NO: 37, or fragment thereof, which encodes a butyrylcholinesterase variant encompassing the same or substantially the same amino acid sequence shown as SEQ ID NO: 38. As shown in Table 1, the nucleic acid shown as SEQ ID: 37 differs from the nucleic acid encoding human butyrylcholinesterase shown in FIG. 3 and designated SEQ ID NO: 43, at the codon position encoding amino acid residue 227. In the human butyrylcholinesterase (SEQ ID NO: 43) the codon ttt encodes Phenylalanine at amino acid position 227. In contrast, in the nucleic acid encoding the F227C butyrylcholinesterase variant designated SEQ ID NO: 38, the codon tgt encodes Cysteine at amino acid position 227.

The invention provides a further nucleic acid shown as SEQ ID NO: 39, or fragment thereof, which encodes a butyrylcholinesterase variant encompassing the same or substantially the same amino acid sequence shown as SEQ ID NO: 40. As shown in Table 1, the nucleic acid shown as SEQ ID: 39 differs from the nucleic acid encoding human butyrylcholinesterase shown in FIG. 3 and designated SEQ ID NO: 43, at the codon position encoding amino acid residue 227. In the human butyrylcholinesterase (SEQ ID NO: 43) the codon ttt encodes Phenylalanine at amino acid position 227. In contrast, in the nucleic acid encoding the F227M butyrylcholinesterase variant designated SEQ ID NO: 40, the codon atg encodes Methionine at amino acid position 227.

The invention provides a further nucleic acid shown as SEQ ID NO: 41, or fragment thereof, which encodes a butyrylcholinesterase variant encompassing the same or substantially the same amino acid sequence shown as SEQ ID NO: 42. As shown in Table 1, the nucleic acid shown as SEQ ID: 41 differs from the nucleic acid encoding human butyrylcholinesterase shown in FIG. 3 and designated SEQ ID NO: 43, at the codon position encoding amino acid residue 199. In the human butyrylcholinesterase (SEQ ID NO: 43) the codon gca encodes Alanine at amino acid position 199. In contrast, in the nucleic acid encoding the A199S butyrylcholinesterase variant designated SEQ ID NO: 42, the codon tca encodes Serine at amino acid position 199.

The invention provides a further nucleic acid shown as SEQ ID NO: 51, or fragment thereof, which encodes a butyrylcholinesterase variant encompassing the same or substantially the same amino acid sequence shown as SEQ ID NO: 52. As shown in Table 1, the nucleic acid shown as SEQ ID: 52 differs from the nucleic acid encoding human butyrylcholinesterase shown in FIG. 3 and designated SEQ ID NO: 43, at the codon positions encoding amino acid residues 227, 287, 332 and 328. In the human butyrylcholinesterase (SEQ ID NO: 43) the codons ttt, tca, gct and tat encode Alanine at amino acid position 199, Phenylalanine at amino acid position 227, Serine at amino acid position 287, Alanine at amino acid position 328 and Tyrosine at amino acid position 332. In contrast, in the nucleic acid encoding the A328W/Y332M/S287G/F227A butyrylcholinesterase variant designated SEQ ID NO: 52, the codons gcg, ggt, tgg and atg encode Alanine at amino acid position 227, Glycine at amino acid position 287, Tryptophan at amino acid position 328 and Methionine at amino acid position 332, respectively.

TABLE 1

Nucleotide Sequences Corresponding to Amino Acid Positions 199, 227, 287, 328, 331 and 332. Codon sequences that differ from human butyrylcholinesterase (SEQ ID NO: 43) are set forth below.

| | SEQ ID NO na (aa) | 199 | 227 | 287 | 328 | 331 | 332 |
|---|---|---|---|---|---|---|---|
| Human BchE | 43 (44) | gca | ttt | tca | gct | gtc | tat |
| A328W/Y332M | 1 (2) | | | | tgg | | atg |
| A328W/Y332P | 3 (4) | | | | tgg | | cca |
| A328W/V331L | 5 (6) | | | | tgg | ttg | |
| A328W/Y332S | 7 (8) | | | | tgg | | tcg |
| A328W/Y332M/ S287G/F227A/ A199S | 9 (10) | tca | gcg | ggt | tgg | | atg |
| A328W/S287G/ F227A/A199S | 11(12) | tca | gcg | ggt | tgg | | |
| A328W/S287G/ A199S | 13 (14) | tca | | ggt | tgg | | |
| A328W/S287G/ F227A | 15 (16) | | gcg | ggt | tgg | | |
| A328W/F227A | 17 (18) | | gcg | | tgg | | |
| Y332S | 19 (20) | | | | | | tcg |
| Y332M | 21 (22) | | | | | | atg |
| Y332P | 23 (24) | | | | | | cca |
| V331L | 25 (26) | | | | | ttg | |
| F227A | 27 (28) | | gcg | | | | |
| F227G | 29 (30) | | ggg | | | | |
| F227S | 31 (32) | | agt | | | | |
| F227P | 33 (34) | | ccg | | | | |
| F227T | 35 (36) | | act | | | | |
| F227C | 37 (38) | | tgt | | | | |
| F227M | 39 (40) | | atg | | | | |
| A199S | 41 (42) | tca | | | | | |
| A328W/Y332M/ S287G/F227A | 51 (52) | | gcg | ggt | tgg | | atg |

A butyrylcholinesterase variant can be obtained by screening a library or collection of molecules. A library can contain a few or a large number of different molecules, varying from as small as 2 molecules to as large as $10^{13}$ or more molecules. Therefore, a library can range in size from 2 to 10, 10 to $10^2$, $10^2$ to $10^3$, $10^3$ to $10^5$, $10^5$ to $10^8$, $10^8$ to $10^{10}$ or $10^{10}$ to $10^{13}$ molecules. The molecules making up a library can be nucleic acid molecules such as an RNA, a cDNA or an oligonucleotide; a peptide or polypeptide including a variant or modified peptide or a peptide containing one or more amino acid analogs. In addition, the molecules making up a library can be peptide-like molecules, referred to herein as peptidomimetics, which mimic the activity of a peptide; or a polypeptide such as an enzyme or a fragment thereof. Moreover, a library can be diverse or redundant depending on the intent and needs of the user. Those skilled in the art will know the size and diversity of a library suitable for obtaining a butyrylcholinesterase variant polypeptide.

A library that is sufficiently diverse to contain a butyrylcholinesterase variant with enhanced cocaine hydrolysis activity can be prepared by a variety of methods well known in the art. For example, a library of butyrylcholinesterase variants can be prepared that contains each of the 19 amino acids not found in the reference butyrylcholinesterase at each of the approximately 573 amino acid positions and screening the resultant variant library for butyrylcholinesterase variants with enhanced cocaine hydrolysis activity.

Alternatively, a butyrylcholinesterase variant polypeptide can be obtained from focused library prepared utilizing the structural, biochemical and modeling information relating to butyrylcholinesterase as described herein. It is understood that any information relevant to the determination or prediction of residues or regions important for the cocaine hydrolysis activity or structural function of butyrylcholinesterase can be useful in the design of a focused library of butyrylcholinesterase variants. Thus, the butyrylcholinesterase variants can be focused to contain amino acid alterations at amino acid positions located in regions determined or predicted to be important for cocaine hydrolysis activity. A focused library of butyrylcholinesterase variants can be screened in order to identify a butyrylcholinesterase variant with enhanced cocaine hydrolysis activity by targeting amino acid alterations to regions determined or predicted to be important for cocaine hydrolysis activity.

Regions important for the cocaine hydrolysis activity of butyrylcholinesterase can be determined or predicted. Related enzymes such as, for example, acetylcholinesterase and carboxylesterase, that share a high degree of sequence similarity and have biochemically similar catalytic properties can provide information regarding the regions important for catalytic activity of butyrylcholinesterase. For example, structural modeling can reveal the active site of an enzyme, which is a three-dimensional structure such as a cleft, gorge or crevice formed by amino acid residues generally located apart from each other in primary structure. Therefore, amino acid residues that make up regions of butyrylcholinesterase important for cocaine hydrolysis activity can include residues located along the active site gorge. For a description of structural modeling of butyrylcholinesterase, see for example, Harel et al., *Proc. Nat. Acad. Sci. USA* 89: 10827–10831 (1992) and Soreq et al., *Trends Biochem. Sci.* 17(9): 353–358 (1992), which are incorporated herein by reference.

In addition to structural modeling of butyrylcholinesterase, biochemical data can be used to determine or predict regions of butyrylcholinesterase important for cocaine hydrolysis activity. In this regard, the characterization of naturally occurring butyrylcholinesterase variants with altered cocaine hydrolysis activity is useful for identifying regions important for the catalytic activity of butyrylcholinesterase. Similarly, site-directed mutagenesis studies can provide data regarding catalytically important amino acid residues as reviewed, for example, in Schwartz et al., *Pharmac. Ther.* 67: 283–322 (1992), which is incorporated by reference.

To prepare a butyrylcholinesterase variant having enhanced cocaine hydrolysis activity, distinct types of information can be used alone or combined to determine or predict a region of an amino acid sequence or a specific amino acid residue of butyrylcholinesterase important for cocaine hydrolysis activity. For example, information based on structural modeling and biochemical data is combined to determine a region of an amino acid sequence or a specific amino acid residue of butyrylcholinesterase important for cocaine hydrolysis activity. Because information obtained by a variety of methods can be combined to predict the catalytically active regions, one skilled in the art will appreciate that the regions themselves represent approximations rather than strict confines. As a result, a butyrylcholinesterase variant can have amino acid alterations outside of the regions determined or predicted to be important for cocaine hydrolysis activity. Similarly, a butyrylcholinesterase variant of the invention can have amino acid alterations outside of the regions determined or predicted to be important for cocaine hydrolysis activity. Furthermore, a butyrylcholinesterase variant of the invention can have any other modification that does not significantly change its cocaine hydrolysis activity. It is further understood that the number of regions determined or predicted to be important for cocaine hydrolysis activity can vary based on the predictive methods used.

Once a number of regions or specific residues have been identified by any method appropriate for determination of regions or specific amino acid residues important for cocaine hydrolysis, each region or specific positions can be randomized across some or all amino acid positions to create a library of variants containing the wild-type amino acid plus one or more of the other nineteen naturally occurring amino acids at one or more positions within each of the regions. As summarized in Table 2, regions of an amino acid sequence of butyrylcholinesterase important for cocaine hydrolysis can include, for example, amino acid residues 68 through 82, 110 through 121, 194 through 201, 224 through 234, 277 through 289, 327 through 332, and 429 through 442 corresponding to the human butyrylcholinesterase designated SEQ ID NO: 44.

Methods for preparing libraries containing diverse populations of various types of molecules such as peptides, peptoids and peptidomimetics are well known in the art (see, for example, Ecker and Crooke, *Biotechnology* 13:351–360 (1995), and Blondelle et al., *Trends Anal. Chem.* 14:83–92 (1995), and the references cited therein, each of which is incorporated herein by reference; see, also, Goodman and Ro, *Peptidomimetics for Drug Design*, in "Burger's Medicinal Chemistry and Drug Discovery" Vol. 1 (ed. M. E. Wolff; John Wiley & Sons 1995), pages 803–861, and Gordon et al. *J. Med. Chem.* 37:1385–1401 (1994), each of which is incorporated herein by reference). Where a molecule is a peptide, protein or fragment thereof, the molecule can be produced in vitro directly or can be expressed from a nucleic acid, which can be produced in vitro. Methods of synthetic peptide chemistry are well known in the art.

A butyrylcholinesterase variant of the invention also can be produced, for example, by constructing and subsequently screening a nucleic acid expression library encoding butyrylcholinesterase variants. Methods for producing such libraries are well known in the art (see, for example, Sambrook et al., supra, 1989). A library of nucleic acids can be composed of DNA, RNA or analogs thereof. A library containing RNA molecules can be constructed, for example, by synthesizing the RNA molecules chemically.

A nucleic acid encoding a butyrylcholinesterase variant can be obtained by any means desired by the user. Those skilled in the art will know what methods can be used to obtain a nucleic acid encoding butyrylcholinesterase variant of the invention. For example, a butyrylcholinesterase variant can be generated by mutagenesis of nucleic acids encoding butyrylcholinesterase using methods well known to those skilled in the art (*Molecular Cloning: A Laboratory Manual*, Sambrook et al., supra, 1989). A butyrylcholinesterase variant of the invention can be obtained from a library of nucleic acids that is randomized to be sufficiently diverse to contain nucleic acids encoding every possible naturally occurring amino acid at each amino acid position of butyrylcholinesterase. Alternatively, a butyrylcholinesterase variant of the invention can be obtained from a library of nucleic acids such that it contains a desired amino acid at a predetermined position predicted or determined to be important for cocaine hydrolysis activity.

One or more mutations can be introduced into a nucleic acid molecule encoding a butyrylcholinesterase variant to yield a modified nucleic acid molecule using, for example, site-directed mutagenesis (see Wu (Ed.), *Meth. In Enzymol.* Vol. 217, San Diego: Academic Press (1993); Higuchi, "Recombinant PCR" in Innis et al. (Ed.), *PCR Protocols*, San Diego: Academic Press, Inc. (1990), each of which is incorporated herein by reference). Such mutagenesis can be used to introduce a specific, desired amino acid alteration.

The efficient synthesis and expression of libraries of butyrylcholinesterase variants using oligonucleotide-directed mutagenesis can be accomplished as previously described by Wu et al., *Proc. Natl. Acad. Sci. USA*, 95:6037–6042 (1998); Wu et al., *J. Mol. Biol.*, 294:151–162 (1999); and Kunkel, *Proc. Natl. Acad. Sci. USA*, 82:488–492 (1985), which are incorporated herein by reference. Oligonucleotide-directed mutagenesis is a well-known and efficient procedure for systematically introducing mutations, independent of their phenotype and is, therefore, ideally suited for directed evolution approaches to protein engineering. To perform oligonucleotide-directed mutagenesis a library of nucleic acids encoding the desired mutations is hybridized to single-stranded uracil-containing template of the wild-type sequence. The methodology is flexible, permitting precise mutations to be introduced without the use of restriction enzymes, and is relatively inexpensive if oligonucleotides are synthesized using codon-based mutagenesis.

Codon-based synthesis or mutagenesis represents one method well known in the art for avoiding genetic redundancy while rapidly and efficiently producing a large number of alterations in a known amino acid sequence or for generating a diverse population of random sequences. This method is the subject matter of U.S. Pat. Nos. 5,264,563 and 5,523,388 and is also described in Glaser et al. *J. Immunology* 149:3903–3913 (1992). Briefly, coupling reactions for the randomization of, for example, all twenty codons which specify the amino acids of the genetic code are performed in separate reaction vessels and randomization for a particular codon position occurs by mixing the products of each of the reaction vessels. Following mixing, the randomized reaction products corresponding to codons encoding an equal mixture of all twenty amino acids are then divided into separate reaction vessels for the synthesis of each randomized codon at the next position. If desired, equal frequencies of all twenty amino acids can be achieved with twenty vessels that contain equal portions of the twenty codons. Thus, it is possible to utilize this method to generate random libraries of the entire sequence of butyrylcholinesterase or focused libraries of the regions or specific positions determined or predicted to be important for cocaine hydrolysis activity.

Variations to the above synthesis method also exist and include, for example, the synthesis of predetermined codons at desired positions and the biased synthesis of a predetermined sequence at one or more codon positions as described by Wu et al, supra, 1998. Biased synthesis involves the use of two reaction vessels where the predetermined or parent codon is synthesized in one vessel and the random codon sequence is synthesized in the second vessel. The second vessel can be divided into multiple reaction vessels such as that described above for the synthesis of codons specifying totally random amino acids at a particular position. Alternatively, a population of degenerate codons can be synthesized in the second reaction vessel such as through the coupling of NNG/T nucleotides or NNX/X where N is a mixture of all four nucleotides. Following synthesis of the predetermined and random codons, the reaction products in each of the two reaction vessels are mixed and then redivided into an additional two vessels for synthesis at the next codon position.

A modification to the above-described codon-based synthesis for producing a diverse number of variant sequences can similarly be employed for the production of the libraries of butyrylcholinesterase variants described herein. This modification is based on the two vessel method described above which biases synthesis toward the parent sequence and allows the user to separate the variants into populations containing a specified number of codon positions that have random codon changes.

Briefly, this synthesis is performed by continuing to divide the reaction vessels after the synthesis of each codon position into two new vessels. After the division, the reaction products from each consecutive pair of reaction vessels, starting with the second vessel, is mixed. This mixing brings together the reaction products having the same number of codon positions with random changes. Synthesis proceeds by then dividing the products of the first and last vessel and the newly mixed products from each consecutive pair of reaction vessels and redividing into two new vessels. In one of the new vessels, the parent codon is synthesized and in the second vessel, the random codon is synthesized. For example, synthesis at the first codon position entails synthesis of the parent codon in one reaction vessel and synthesis of a random codon in the second reaction vessel. For synthesis at the second codon position, each of the first two reaction vessels is divided into two vessels yielding two pairs of vessels. For each pair, a parent codon is synthesized in one of the vessels and a random codon is synthesized in the second vessel. When arranged linearly, the reaction products in the second and third vessels are mixed to bring together those products having random codon sequences at single codon positions. This mixing also reduces the product populations to three, which are the starting populations for the next round of synthesis. Similarly, for the third, fourth and each remaining position, each reaction product population for the preceding position are divided and a parent and random codon synthesized.

Following the above modification of codon-based synthesis, populations containing random codon changes at one, two, three and four positions as well as others can be conveniently separated out and used based on the need of the individual. Moreover, this synthesis scheme also allows enrichment of the populations for the randomized sequences over the parent sequence since the vessel containing only the parent sequence synthesis is similarly separated out from the random codon synthesis. This method can be used to synthesize a library of nucleic acids encoding butyrylcholinesterase variants having amino acid alterations in one or more regions of butyrylcholinesterase predicted to be important for cocaine hydrolysis activity.

Alternatively, a library of nucleic acids encoding butyrylcholinesterase variants can also be generated using gene shuffling. Gene shuffling or DNA shuffling is a method for directed evolution that generates diversity by recombination (see, for example, Stemmer, *Proc. Natl. Acad. Sci. USA* 91:10747–10751 (1994); Stemmer, *Nature* 370:389–391 (1994); Crameri et al., *Nature* 391:288–291 (1998); Stemmer et al., U.S. Pat. No. 5,830,721, issued Nov. 3, 1998). Gene shuffling or DNA shuffling is a method using in vitro homologous recombination of pools of selected mutant genes. For example, a pool of point mutants of a particular gene can be used. The genes are randomly fragmented, for example, using DNase, and reassembled by PCR. If desired, DNA shuffling can be carried out using homologous genes from different organisms to generate diversity (Crameri et al., supra, 1998). The fragmentation and reassembly can be carried out in multiple rounds, if desired. The resulting reassembled genes constitute a library of butyrylcholinesterase variants that can be used in the invention compositions and methods.

Thus, the invention also provides nucleic acids shown as SEQ ID NOS: SEQ ID NOS: 1, 3, 5, 7, 9, 11, 13, 15, 17, 19, 21, 23, 25, 27, 29, 31, 33, 35, 37, 39, 41, and 51, respectively, or fragments thereof, which encode the butyrylcholinesterase variants encompassing the same or substantially the same amino acid sequences shown as SEQ ID NOS: 2, 4, 6, 8, 10, 12, 14, 16, 18, 20, 22, 24, 26, 28, 30, 32, 34, 36, 38, 40, 42 and 52, respectively.

The invention nucleic acids encoding butyrylcholinesterase variants can be expressed in a variety of eukaryotic cells. For example, the nucleic acids can be expressed in mammalian cells, insect cells, plant cells, and non-yeast fungal cells. Mammalian cell lines useful for expressing the invention library of nucleic acids encoding butyrylcholinesterase variants include, for example, Chinese Hamster Ovary (CHO), human T293 and Human NIH 3T3 cell lines. Expression of the invention library of nucleic acids encoding butyrylcholinesterase variants can be achieved by both stable or transient cell transfection (see Example III, Table 3).

The incorporation of variant nucleic acids or heterologous nucleic acid fragments at an identical site in the genome functions to create isogenic cell lines that differ only in the expression of a particular variant or heterologous nucleic acid. Incorporation at a single site minimizes positional effects from integration at multiple sites in a genome that affect transcription of the mRNA encoded by the nucleic acid and complications from the incorporation of multiple copies or expression of more than one nucleic acid species per cell. Techniques known in the art that can be used to target a variant or a heterologous nucleic acid to a specific location in the genome include, for example, homologous recombination, retroviral targeting and recombinase-mediated targeting.

One approach for targeting variant or heterologous nucleic acids to a single site in the genome uses Cre recombinase to target insertion of exogenous DNA into the eukaryotic genome at a site containing a site specific recombination sequence (Sauer and Henderson, *Proc. Natl. Acad. Sci. USA,* 85:5166–5170 (1988); Fukushige and Sauer, *Proc. Natl. Acad. Sci. U.S.A.* 89:7905–7909 (1992); Bethke and Sauer, *Nuc. Acids Res.,* 25:2828–2834 (1997)). In addition to Cre recombinase, Flp recombinase can also be used to target insertion of exogenous DNA into a particular site in the genome (Dymecki, *Proc. Natl. Acad. Sci. U.S.A.* 93:6191–6196 (1996)). The target site for Flp recombinase consists of 13 base-pair repeats separated by an 8 base-pair spacer: 5'-GAAGTTCCTATTC[TCTAGAAA]GTATAGGAACTTC-3'. As described herein, the butyrylcholinesterases designated SEQ ID NOS: 2, 4, 6, 8, 10, 12, 14, 16, 18, 20, 22, 24, 26, 28, 30, 32, 34, 36, 38, 40, 42 and 52, were obtained by transfection of variant libraries corresponding to the regions set forth in Table 2 of human butyrylcholinesterase into mammalian cells using Flp recombinase and the human 293T cell line. It is understood that any combination of site-specific recombinase and corresponding recombination site can be used in methods of the invention to target a nucleic acid to a particular site in the genome.

A suitable recombinase can be encoded on a vector that is co-transfected with a vector containing a nucleic acid encoding a butyrylcholinesterase variant. Alternatively, the expression element of a recombinase can be incorporated into the same vector expressing a nucleic acid encoding a butyrylcholinesterase variant. In addition to simultaneously transfecting the nucleic acid encoding a recombinase with the nucleic acids encoding a butyrylcholinesterase variant, a vector encoding the recombinase can be transfected into a cell, and the cells can be selected for expression of recombinase. A cell stably expressing the recombinase can subsequently be transfected with nucleic acids encoding variant nucleic acids.

As disclosed herein, the precise site-specific DNA recombination mediated by Cre recombinase can be used to create stable mammalian transformants containing a single copy of exogenous DNA encoding a butyrylcholinesterase variant. As exemplified below, the frequency of Cre-mediated targeting events can be enhanced substantially using a modified doublelox strategy. The doublelox strategy is based on the observation that certain nucleotide changes within the core region of the lox site alter the site selection specificity of Cre-mediated recombination with little effect on the efficiency of recombination (Hoess et al., Nucleic Acids Res. 14:2287–2300 (1986)). Incorporation of loxP and an altered loxP site, termed lox511, in both the targeting vector and the host cell genome results in site-specific recombination by a double crossover event. The doublelox approach increases the recovery of site-specific integrants by 20-fold over the single crossover insertional recombination, increasing the absolute frequency of site-specific recombination such that it exceeds the frequency of illegitimate recombination (Bethke and Sauer, Nuc. Acids Res., 25:2828–2834 (1997)).

Following the expression of a library of butyrylcholinesterase variants in a mammalian cell line, randomly selected clones can be sequenced and screened for increased cocaine hydrolysis activity. Methods for sequencing selected clones are well known to those of skill in the art and are described, for example, in Sambrook et al., supra, 1989, and in Ausubel et al., supra, 2000. Selecting a suitable method for measuring the cocaine hydrolysis activity of a butyrylcholinesterase variant depends on a variety of factors such as, for example, the amount of the butyrylcholinesterase variant that is available. The cocaine hydrolysis activity of a butyrylcholinesterase variant can be measured, for example, by spectrophotometry, by a microtiter-based assay utilizing a polyclonal anti-butyrylcholinesterase antibody to uniformly capture the butyrylcholinesterase variants and by high-performance liquid chromatography (HPLC).

Enhanced cocaine hydrolysis activity of a butyrylcholinesterase variant compared to butyrylcholinesterase can be determined by a comparison of catalytic efficiencies. Clones expressing butyrylcholinesterase variants exhibiting increased cocaine hydrolysis activity can be sequenced to confirm the precise location and nature of the mutation. To ensure that a library of butyrylcholinesterase variants has been screened exhaustively, screening of each library can be continued until clones encoding identical butyrylcholinesterase amino acid alterations have been identified on multiple occasions.

Clones expressing a butyrylcholinesterase variant with increased cocaine hydrolysis activity can be used to establish larger-scale cultures suitable for purifying larger quantities of the butyrylcholinesterase. A butyrylcholinesterase variant of interest can be cloned into an expression vector and used to transfect a cell line, which can subsequently be expanded. Those skilled in the art will know what type of expression vector is suitable for a particular application. A butyrylcholinesterase variant exhibiting increased cocaine hydrolysis activity can be cloned, for example, into an expression vector carrying a gene that confers resistance to a particular chemical agent to allow positive selection of the transfected cells. An expression vector suitable for transfection of, for example, mammalian cell lines can contain a promoter such as the cytomegalovirus (CMV) promoter for selection in mammalian cells. As described herein, a butyrylcholinesterase variant can be cloned into a mammalian expression vector and transfected into Chinese Hamster Ovary cells (CHO). Expression vectors suitable for expressing a butyrylcholinesterase variant are well known in the art and commercially available.

Clones expressing butyrylcholinesterase variants can be selected and tested for cocaine hydrolysis activity. Cells carrying clones exhibiting enhanced cocaine hydrolysis activity can be expanded by routine cell culture systems to produce larger quantities of a butyrylcholinesterase variant of interest. The concentrated recombinant butyrylcholinesterase variant can be harvested and purified by methods well known in the art and described, for example, by Masson et al., Biochemistry 36: 2266–2277 (1997), which is incorporated herein by reference.

A butyrylcholinesterase variant exhibiting increased cocaine hydrolysis activity in vitro can be utilized for the treatment of cocaine toxicity and addiction in vivo. The potency for treating cocaine toxicity of a butyrylcholinesterase variant exhibiting increased cocaine hydrolysis activity in vitro can be tested using an acute overdose animal model as disclosed herein (see Example VI). In addition, animal models of reinforcement and discrimination are used to predict the efficacy of a butyrylcholinesterase variant for treatment of cocaine addiction as disclosed below (see Example VI). Suitable animal subjects for overdose as well as reinforcement and discrimination models are known in the art and include, for example, rodent and primate models. A butyrylcholinesterase variant effective in reducing either cocaine toxicity or cocaine addiction in one or more animal models can be used to treat a cocaine-induced condition by administering an effective amount of the butyrylcholinesterase variant to an individual.

A butyrylcholinesterase variant having an increased serum half-life can be useful for testing a butyrylcholinesterase variant in a subject or treating a cocaine-induced condition in an individual. Useful methods for increasing the serum half-life of a butyrylcholinesterase variant include, for example, conversion of the butyrylcholinesterase variant into a tetramer, covalently attaching synthetic and natural polymers such as polyethylene glycol (PEG) and dextrans to the truncated butyrylcholinesterase variant, liposome formulations, or expression of the enzyme as an Ig-fusion protein. Furthermore, conversion of a butrylcholinesterase variant into a tetramer can be achieved by co-transfecting the host cell line with the COLQ gene as well as by addition of poly-L-proline to the media of transfected cells. These and other methods known in the art for increasing the serum half-life of a butyrylcholinesterase variant are useful for testing a butyrylcholinesterase variant in an animal subject or treating a cocaine-induced condition in an individual.

The invention also provides a method of hydrolyzing a cocaine-based butyrylcholinesterase substrate including contacting a butyrylcholinesterase substrate with a butyrylcholinesterase variant selected from the group shown as SEQ ID NOS: 2, 4, 6, 8, 10, 12, 14, 16, 18, 20, 22, 24, 26, 28, 30, 32, 34, 36, 38, 40, 42 and 52, under conditions that allow hydrolysis of cocaine into metabolites, wherein the butyrylcholinesterase variant exhibits increased cocaine hydrolysis activity compared to butyrylcholinesterase as described herein for each of these variants.

The invention further provides a method of treating a cocaine-induced condition including administering to an individual an effective amount of the butyrylcholinesterase variant selected from the group shown as SEQ ID NOS: 2, 4, 6, 8, 10, 12, 14, 16, 18, 20, 22, 24, 26, 28, 30, 32, 34, 36, 38, 40, 42 and 52, wherein the butyrylcholinesterase variant exhibits increased cocaine hydrolysis activity compared to butyrylcholinesterase as described herein for each of these variants.

As described herein, a butyrylcholinesterase variant exhibiting increased cocaine hydrolysis activity can hydrolyze a cocaine-based butyrylcholinesterase substrate in vitro as well as in vivo. A cocaine-based butyrylcholinesterase substrate can be contacted with a butyrylcholinesterase variant of the invention in vitro, for example, by adding the substrate to supernatant isolated from cultures of butyrylcholinesterase variant library clones. Alternatively, the butyrylcholinesterase variant can be purified prior to being contacted by the substrate. Appropriate medium conditions in which to contact a cocaine-based substrate with a butyrylcholinesterase variant of the invention are readily determined by those skilled in the art. For example, 100 μM cocaine in 10 mM Tris at pH 7.4 can be contacted with a butyrylcholinesterase variant at 37° C. As described below, butyrylcholinesterase variants from culture supernatants can further be immobilized using a capture agent, such as an antibody prior to being contacted with a substrate, which allows for removal of culture supernatant components and enables contacting of the immobilized variants with substrate in the absence of contaminants. Following contacting of a butyrylcholinesterase variant of the invention with a cocaine-based substrate, cocaine hydrolysis activity can be measured by a variety of methods known in the art and described herein, for example, by high-performance liquid chromatography or the isotope tracer cocaine hydrolysis assay.

Figure 8:
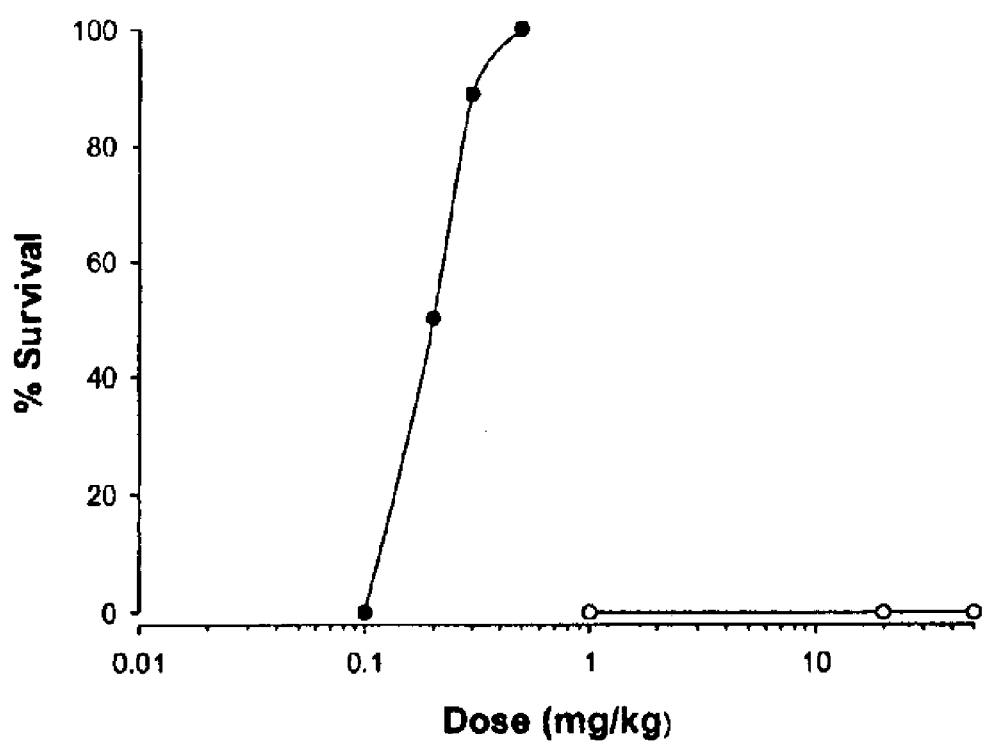
FIG. 8 shows the effect of pre-treatment with AME-359 (solid circles) or wild-type BChE (open circles) on cocaine-induced toxicity. AME-359 exhibited statistically significant protection against cocaine (Chi-squared test; p<0.001).

The invention also provides a method of treating cocaine overdose as well as cocaine addiction in an individual by administering a therapeutically effective amount of the butyrylcholinesterase variant. Treatment of a cocaine-induced condition encompasses prophylactic applications of the invention method in which the invention variant is administered to an individual predicted to be exposed to cocaine at a future time. In prophylactic embodiments of the invention method, a therapeutically effective amount of the butyrylcholinesterase variant is administered prior to cocaine-exposure. As demonstrated in FIGS. 8 and 12 for the A328W/Y332M/S287G/F227A variant (SEQ ID NO: 52), pre-treatment with an invention variant has a therapeutic effect by decreasing cocaine-toxicity in general as well as by delaying the time-of-onset of symptoms associated with cocaine-induced toxicity.

The dosage of a butyrylcholinesterase variant required to be effective depends, for example, on whether an acute overdose or chronic addiction is being treated, the route and form of administration, the potency and bio-active half-life of the molecule being administered, the weight and condition of the individual, and previous or concurrent therapies. The appropriate amount considered to be an effective dose for a particular application of the method can be determined by those skilled in the art, using the teachings and guidance provided herein. For example, the amount can be extrapolated from in vitro or in vivo butyrylcholinesterase assays described herein. One skilled in the art will recognize that the condition of the individual needs to be monitored throughout the course of treatment and that the amount of the composition that is administered can be adjusted accordingly.

For treating cocaine-overdose, a therapeutically effective amount of a butyrylcholinesterase variant of the invention can be, for example, between about 0.1 mg/kg to 0.15 mg/kg body weight, for example, between about 0.15 mg/kg to 0.3 mg/kg, between about 0.3 mg/kg to 0.5 mg/kg or preferably between about 1 mg/kg to 5 mg/kg, depending on the treatment regimen. For example, if a butyrylcholinesterase variant is administered to an individual symptomatic of cocaine overdose a higher one-time dose is appropriate, while an individual symptomatic of chronic cocaine addiction may be administered lower doses from one to several times a day, weekly, monthly or less frequently. Similarly, formulations that allow for timed-release of a butyrylcholinesterase variant would provide for the continuous release of a smaller amount of a butyrylcholinesterase variant to an individual treated for chronic cocaine addiction. It is understood, that the dosage of a butyrylcholinesterase variant has to be adjusted based on the catalytic activity of the variant, such that a lower dose of a variant exhibiting significantly enhanced cocaine hydrolysis activity can be administered compared to the dosage necessary for a variant with lower cocaine hydrolysis activity.

Figure 9:
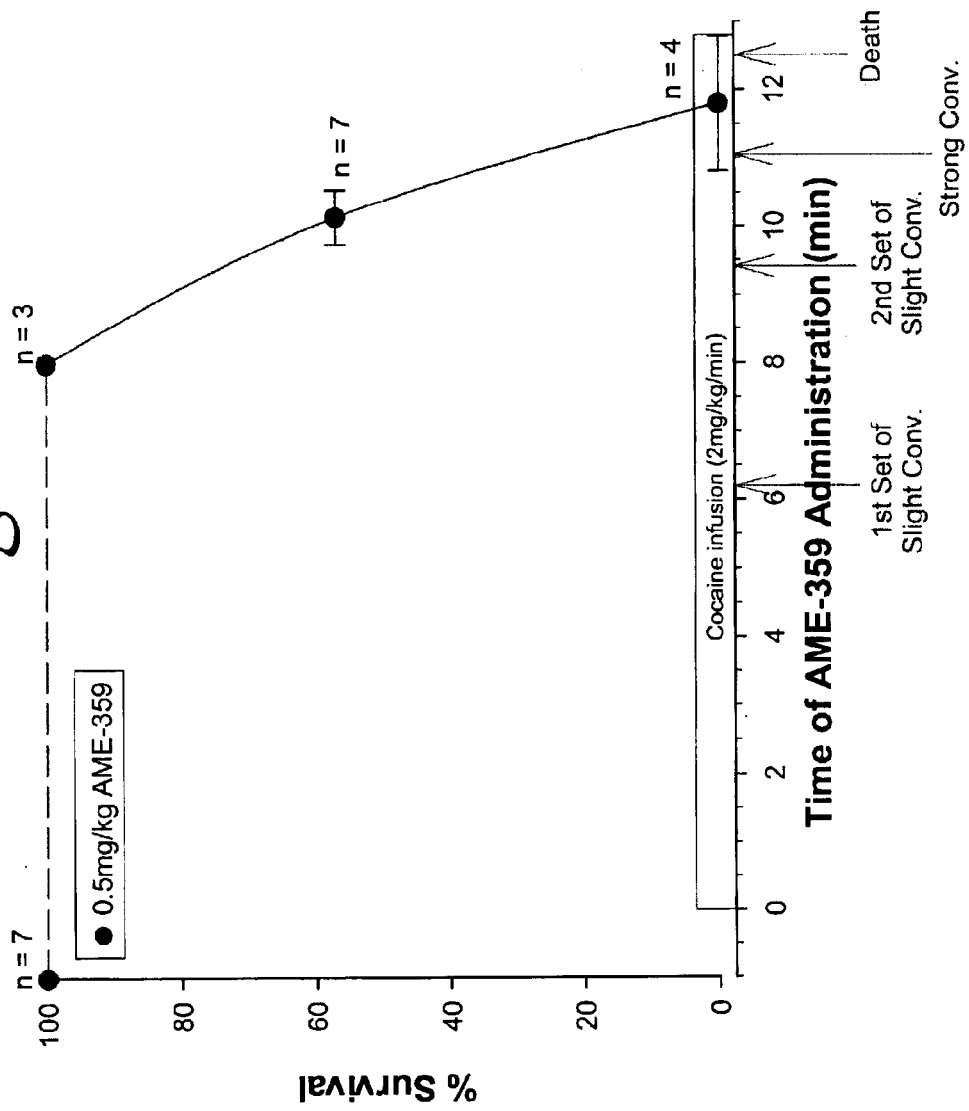
FIG. 9 shows the effect of therapeutic treatment with AME-359 on cocaine-induced toxicity. AME-359 maintained full protection when administered at 8 minutes into the cocaine infusion (in particular, measured from the first set of slight convulsions) and decreased in ability to protect when administered at later time points.

The time for commencing treatment with a butyrylcholinesterase variant can be prior to contact with the cocaine-based substrate, for example, cocaine, or can be following contact with the cocaine-based substrate. For treatment of a cocaine overdose it is desirable to administer the invention variant as soon as possible after contact so as to maximize therapeutic effect. As shown in FIG. 9 for the butyrylcholinesterase variant designated A328W/Y332M/S287G/F227A (SEQ ID NO: 52), the effect of therapeutic treatment on cocaine-induced toxicity maintains full protection when administered at 8 minutes after contact and decreased when administered at later time points as a result of onset of physiologically irreversible symptoms of cocaine-toxicity. Nevertheless, as shown in FIG. 9, treatment with an invention variant is effective even after onset of symptoms associated with cocaine-induced toxicity. Therefore, for treatment of cocaine-induced toxicity a butyrylcholinesterase variant of the invention can be administered prior to contact as well as following contact, for example, within seconds or minutes, including after about 1 minute or less, about 2 minutes or less, about 3 minutes or less, about 4 minutes or less, about 5 minutes or less, about 6 minutes or less, about 7 minutes or less, about 8 minutes or less, about 9 minutes or less, about 10 minutes or less, about 11 minutes or less, about 12 minutes or less, about 13 minutes or less, about 14 minutes or less, about 15 minutes or less, about 16 minutes or less, about 17 minutes or less, about 18 minutes or less, about 19 minutes or less, about 20 minutes or less, about 21 minutes or less, about 22 minutes or less, about 23 minutes or less, about 24 minutes or less, about 25 minutes or less, about 30 minutes or less, about 35 minutes or less, about 40 minutes or less, about 45 minutes or less, about 50 minutes or less, about 55 minutes or less, about 60 minutes or less, about 90 minutes or less, and about 120 minutes or less.

It is understood that the timing of effective treatment for toxicity is limited only by the irreversibility of the physiological symptoms and damage associated with the cocaine-induced toxicity. As shown in FIG. 9, effective treatment was fully sustained through onset of particular symptoms, in particular, the first set of slight convulsions, and was significantly sustained even through the onset of more advanced symptoms, in particular, the second set of convulsions. Thus, it is further understood that effectiveness of treatment can be generally associated with time after contact, but also can be viewed as it corresponds to the progression of symptoms. For example, it can be useful to observe progression of symptoms following contact to choose particular treatment parameters based on observations regarding the progression of symptoms rather than on progression of time.

A butyrylcholinesterase variant can be delivered systemically, such as intravenously or intraarterially. A butyrylcholinesterase variant can be provided in the form of isolated and substantially purified polypeptides and polypeptide fragments in pharmaceutically acceptable formulations using formulation methods known to those of ordinary skill in the art. These formulations can be administered by standard routes, including for example, topical, transdermal, intraperitoneal, intracranial, intracerebroventricular, intracerebral, intravaginal, intrauterine, oral, rectal or parenteral (e.g., intravenous, intraspinal, subcutaneous or intramuscular) routes. In addition, a butyrylcholinesterase variant can be incorporated into biodegradable polymers allowing for sustained release of the compound useful for treating individual symptomatic of cocaine addiction. Biodegradable polymers and their use are described, for example, in detail in Brem et al., *J. Neurosurg.* 74:441–446 (1991), which is incorporated herein by reference.

A butyrylcholinesterase variant can be administered as a solution or suspension together with a pharmaceutically acceptable medium. Such a pharmaceutically acceptable medium can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester. A pharmaceutically acceptable medium can additionally contain physiologically acceptable compounds that act, for example, to stabilize or increase the absorption of the butyrylcholinesterase variant. Such physiologically acceptable compounds include, for example, carbohydrates such as glucose, sucrose or dextrans; antioxidants such as ascorbic acid or glutathione; chelating agents such as EDTA, which disrupts microbial membranes; divalent metal ions such as calcium or magnesium; low molecular weight proteins; lipids or liposomes; or other stabilizers or excipients.

Formulations suitable for parenteral administration include aqueous and non-aqueous sterile injection solutions such as the pharmaceutically acceptable mediums described above. The solutions can additionally contain, for example, buffers, bacteriostats and solutes which render the formulation isotonic with the blood of the intended recipient. Other formulations include, for example, aqueous and non-aqueous sterile suspensions which can include suspending agents and thickening agents. The formulations can be presented in unit-dose or multi-dose containers, for example, sealed ampules and vials, and can be stored in a lyophilized condition requiring, for example, the addition of the sterile liquid carrier, immediately prior to use. Extemporaneous injection solutions and suspensions can be prepared from sterile powders, granules and tablets of the kind previously described.

The butyrylcholinesterase variant of the invention can further be utilized in combination therapies with other therapeutic agents. Combination therapies that include a butyrylcholinesterase variant can consist of formulations containing the variant and the additional therapeutic agent individually in a suitable formulation. Alternatively, combination therapies can consist of fusion proteins, where the butyrylcholinesterase variant is linked to a heterologous protein, such as a therapeutic protein.

The butyrylcholinesterase variant of the invention also can be delivered to an individual by administering an encoding nucleic acid for the peptide or variant. The encoding nucleic acids for the butyrylcholinesterase variant of the invention are useful in conjunction with a wide variety of gene therapy methods known in the art for delivering a therapeutically effective amount of the polypeptide or variant. Using the teachings and guidance provided herein, encoding nucleic acids for a butyrylcholinesterase variant can be incorporated into a vector or delivery system known in the art and used for delivery and expression of the encoding sequence to achieve a therapeutically effective amount. Applicable vector and delivery systems known in the art include, for example, retroviral vectors, adenovirus vectors, adenoassociated virus, ligand conjugated particles and nucleic acids for targeting, isolated DNA and RNA, liposomes, polylysine, and cell therapy, including hepatic cell therapy, employing the transplantation of cells modified to express a butyrylcholinesterase variant, as well as various other gene delivery methods and modifications known to those skilled in the art, such as those described in Shea et al., *Nature Biotechnology* 17:551–554 (1999), which is incorporated herein by reference.

Specific examples of methods for the delivery of a butyrylcholinesterase variant by expressing the encoding nucleic acid sequence are well known in art and described in, for example, U.S. Pat. No. 5,399,346; U.S. Pat. Nos. 5,580,859; 5,589,466; 5,460,959; 5,656,465; 5,643,578; 5,620,896; 5,460,959; 5,506,125; European Patent Application No. EP 0 779 365 A2; PCT No. WO 97/10343; PCT No. WO 97/09441; PCT No. WO 97/10343, all of which are incorporated herein by reference. Other methods known to those skilled in the art also exist and are similarly applicable for the delivery of a butyrylcholinesterase variant by expressing the encoding nucleic acid sequence.

In addition to the treatment of cocaine-induced conditions such as cocaine overdose or cocaine addiction, a butyrylcholinesterase can also be administered prophylactically to avoid the onset of a cocaine overdose upon subsequent entry of cocaine into the bloodstream. It is further contemplated that a butyrylcholinesterase variant exhibiting increased cocaine hydrolysis activity of the invention can have diagnostic value by providing a tool for efficiently determining the presence and amount of a cocaine-induced substance in a medium.

It is understood that modifications that do not substantially affect the activity of the various embodiments of this invention are also included within the definition of the invention provided herein. Accordingly, the following examples are intended to illustrate but not limit the present invention.

EXAMPLE I

Development of a Cocaine Hydrolysis Assay

This example describes the development of a cocaine hydrolysis assay that permits the efficient analysis of hundreds of butyrylcholinesterase variants simultaneously.

Development of an Isotope Tracer Cocaine Hydrolysis Assay.

For the purpose of validating new cocaine hydrolysis assays, butyrylcholinesterase hydrolysis of cocaine was first measured as described previously (Xie et al., *Mol. Pharmacol.* 55:83–91 (1999)), using high-performance liquid chromatography (HPLC). Briefly, reactions containing 100 $\mu$M cocaine in 10 mM Tris, pH 7.4 were initiated by the addition of horse butyrylcholinesterase (ICN Pharmaceuticals, Inc., Costa Mesa, Calif.) and incubated 2–4 hours at 37° C. Following the incubation, the pH was adjusted to 3, and the sample was filtered. Subsequently, the sample was applied to a Hypersil ODS-C 18 reversed phase column (Hewlett Packard, Wilmington, Del.) previously equilibrated with an 80:20 mixture of 0.05 M potassium phosphate, pH 3.0 and acetonitrile. The isocratic elution of cocaine, benzoylecgonine, and benzoic acid was quantitated at 220 nm. Measurement of the formation of ecgonine methyl ester and benzoic acid was dependent both on the amount of butyrylcholinesterase in the reaction and on the time of reaction.

At the conclusion of the isotope tracer assay, an aliquot of the reaction mix is acidified in order to take advantage of the solubility difference between the product and the substrate at pH 3.0. At pH 3.0, [3H]-benzoic acid (pKa=4.2) is soluble in a scintillation cocktail consisting of 2,5-diphenyloxazole (PPO) and [1,4-bis-2-(4-methyl-8-phenyloxazolyl)-benzene] (POPOP) (PPO-dimethyl-POPOP scintillation fluor, Research Products International Corp., Mt. Prospect, Ill.) while [3H]-cocaine is not. The signal generated by acidified reaction mixture from enzyme blanks was less than 2% of the total dpm placed in the fluor, consistent with cocaine being insoluble in PPO-dimethyl-POPOP.

Figure 5B:
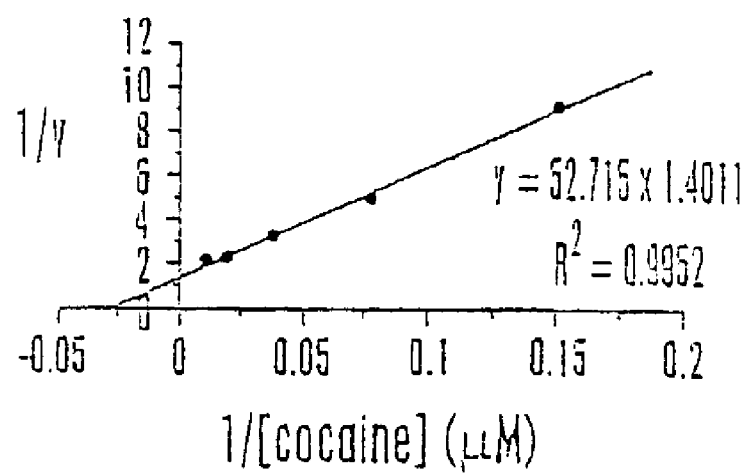

The isotope tracer cocaine hydrolysis assay was validated by direct comparison with the established HPLC assay and the accuracy of the isotope assay was demonstrated by determining the $K_m$ value for horse butyrylcholinesterase. The rate of cocaine hydrolysis, determined by measuring the rate of formation of benzoic acid was quantitated both by HPLC and the isotope tracer assay in reactions containing variable amounts of butyrylcholinesterase. Formation of [$^3$H]-benzoic acid was dependent on the length of assay incubation and on the amount of butyrylcholinesterase added. Good correlation between the established HPLC assay and the isotope tracer assay was observed, as demonstrated by plotting the quantitation of benzoic acid formation measured by HPLC versus the benzoic acid formation measured in the isotope assay (see FIG. 5A; $r^2$=0.979). To demonstrate the precision and sensitivity of the isotope assay the amount of cocaine was varied and the $K_m$ was determined using the Lineweaver-Burk double-reciprocal plot of cocaine hydrolysis by horse butyrylcholinesterase depicted in FIG. 5B. Velocity was calculated as cpm benzoic acid formed×$10^{-5}$ following a 2 hour incubation at 37° C. Based on these data the $K_m$ for cocaine hydrolysis is approximately 37.6 $\mu$M (×intercept=-1/$k_m$), which is in close agreement with previously published values of 38 $\mu$M (Gatley, supra, 1991) and 45±5 $\mu$M (Xie et al., supra, 1999) for horse butyrylcholinesterase.

Immobilization of Active Butyrylcholinesterase

The supernatants isolated from each of the butyrylcholinesterase variant library clones contains variable butyrylcholinesterase enzyme concentrations. Consequently, the cocaine hydrolysis activity measured from equal volumes of culture supernatants from distinct butyrylcholinesterase variant clones reflects the expression level as well as the enzyme activity. In order to be able to compare equal enzyme concentrations and more rapidly identify variants with the desired activity, butyrylcholinesterase from culture supernatants are immobilized using a capture reagent, such as an antibody, that is saturated at low butyrylcholinesterase concentrations as described previously by Watkins et al., Anal. Biochem. 253: 37–45 (1997). As a result, butyrylcholinesterase from dilute samples is concentrated and uniform quantities of different butyrylcholinesterase variant clones are immobilized, regardless of the initial concentration of butyrylcholinesterase in the culture supernatant. Subsequently, unbound butyrylcholinesterase and other culture supernatant components that potentially interfere with the assay (such as unrelated serum or cell-derived proteins with significant esterase activity) are washed away and the activity of the immobilized butyrylcholinesterase is determined by measuring the formation of benzoic acid as described above.

To assess the efficiency of the above assay, efficient capture of human butyrylcholinesterase, as well as a truncated soluble monomeric form of human butyrylcholinesterase (Blong et al., Biochem. J. 327: 747–757 (1997)), was demonstrated in a microtiter format using a commercially available rabbit anti-human cholinesterase polyclonal antibody (DAKO, Carpinteria, Calif.)(FIG. 6). In order to determine the optimal conditions for capturing butyrylcholinesterase a microtiter plate was coated with increasing quantities of rabbit anti-butyrylcholinesterase, was blocked, and incubated with varying amounts of culture supernatant. The amount of active butyrylcholinesterase captured was determined calorimetrically using an assay that measures butyrylthiocholine hydrolysis at 405 nm in the presence of dithiobisnitrobenzoic acid (Xie et al., supra, 1999). Subsequently, the butyrylcholinesterase activity captured from dilutions of culture supernatants from cells expressing either the wild-type human butyrylcholinesterase or the monomeric truncated version was measured. The rabbit anti-butyrylcholinesterase capture antibody was saturated by the butyrylcholinesterase present in 25 $\mu$l of culture supernatant with greater butyrylcholinesterase activity being captured from supernatant containing the full length wild-type form of the enzyme (FIG. 6, compare filled circles with open circles). Unbound material was removed by washing with 100 mM Tris, pH 7.4 and the amount of active butyrylcholinesterase captured was quantitated by measuring butyrylthiocholine hydrolysis. Butyrylcholinesterase is expressed in culture supernatants at quantities sufficient to saturate a polyclonal anti-butyrylcholinesterase antibody on a microtiter plate. In addition, the captured enzyme is active, as demonstrated by the hydrolysis of butyrylthiocholine.

Measurement of Cocaine Hydrolysis with Isotope Tracer Assay and Immobilized Butyrylcholinesterase The optimal conditions for immobilization of active butyrylcholinesterase are used in conjunction with the cocaine isotope tracer assay to measure the cocaine hydrolysis activity in a microtiter format. The assay is characterized by determining the $K_m$ for cocaine hydrolysis activity, as described above. At least three approaches are used to either increase the assay sensitivity or the assay signal.

First, longer assay incubation times that proportionately increase the signal can be used. Second, the sensitivity of the assay can be enhanced by increasing the specific activity of the radiolabeled cocaine substrate. Third, a previously identified butyrylcholinesterase mutant which is 4-fold more efficient for cocaine hydrolysis can used (Xie et al., supra, 1999), which in conjunction with doubling the assay incubation time and increasing the specific activity of the cocaine 10-fold, can increase the assay signal about 80-fold.

EXAMPLE II

Synthesis and Characterization of Butyrylcholinesterase Variant Libraries

This example describes the synthesis and characterization of butyrylcholinesterase variant libraries expressed in mammalian cells.

In order to facilitate the synthesis of libraries of butyrylcholinesterase variants, DNA encoding wild-type human butyrylcholinesterase, a truncated, enzymatically active, monomeric version of human butyrylcholinesterase, and the A328Y mutant that displays a four-fold increased cocaine hydrolysis activity are cloned into a modified doublelox targeting vector, using unique restriction sites. In preliminary assays the wild-type human butyrylcholinesterase was captured more efficiently and, therefore, serves as the initial DNA template for the synthesis of libraries of butyrylcholinesterase variants.

Synthesis of Focused Libraries of Butyrylcholinesterase Variants by Codon-Based Mutagenesis A variety of information can be used to focus the synthesis of the initial libraries of butyrylcholinesterase variants to discreet regions. For example, butyrylcholinesterase and Torpedo acetylcholinesterase (AChE) share a high degree of homology (53% identity). Furthermore, residues 4 to 534 of Torpedo AChE can be aligned with residues 2 to 532 of butyrylcholinesterase without deletions or insertions. The catalytic triad residues (butyrylcholinesterase residues Ser198, Glu325, and His438) and the intrachain disulfides are all in the same positions. Due to the high degree of similarity between these proteins, a refined 2.8—Å x-ray structure of Torpedo AChE (Sussman et al., Science 253: 872–879 (1991)) has been used to model butyrylcholinesterase structure (Harel et al., supra, 1992)).

Studies with cholinesterases have revealed that the catalytic triad and other residues involved in ligand binding are positioned within a deep, narrow, active-site gorge rich in hydrophobic residues (reviewed in Soreq et al., *Trends Biochem. Sci.* 17:353–358 (1992)). The sites of seven focused libraries of butyrylcholinesterase variants (FIG. 2, underlined residues) were selected to include amino acids determined to be lining the active site gorge (FIG. 2, hydrophobic active site gorge residues are shaded).

In addition to the structural modeling of butyrylcholinesterase, butyrylcholinesterase biochemical data was integrated into the library design process. For example, characterization of naturally occurring butyrylcholinesterases with altered cocaine hydrolysis activity and site-directed mutagenesis studies provide information regarding amino acid positions and segments important for cocaine hydrolysis activity (reviewed in Schwartz et al., *Pharmac. Ther.* 67: 283–322(1995)). Moreover, comparison of sequence and cocaine hydrolysis data of butyrylcholinesterases from different species can also provide information regarding regions important for cocaine hydrolysis activity of the molecule based on comparison of the cocaine hydrolysis activities of these butyrylcholinesterases. The previously identified A328Y mutant is present in the library corresponding to region 6 and serves as a control to demonstrate the quality of the library synthesis and expression in mammalian cells as well as the sensitivity of the microtiter-based cocaine hydrolysis assay.

TABLE 2

Butyrylcholinesterase Regions Predicted to be Important for Catalytic Efficiency.

| Region | Location | Length |
|---|---|---|
| 1 | 68–82 | 15 |
| 2 | 110–121 | 12 |
| 3 | 194–201 | 8 |
| 4 | 224–234 | 11 |
| 5 | 277–289 | 13 |
| 6 | 327–332 | 6 |
| 7 | 429–442 | 14 |

The seven regions of butyrylcholinesterase selected for focused library synthesis span residues that include the 8 aromatic active site gorge residues (W82, W112, Y128, W231, F329, Y332, W430 and Y440) as well as two of the catalytic triad residues. The integrity of intrachain disulfide bonds, located between $^{65}$Cys-$^{92}$Cys, $^{252}$Cys-$^{263}$Cys, and $^{400}$Cys-$^{519}$Cys is maintained to ensure functional butyrylcholinesterase structure. In addition, putative glycosylation sites (N-X-S/T) located at residues 17, 57, 106, 241, 256, 341, 455, 481, 485, and 486 also are avoided in the library synthesis. In total, the seven focused libraries span 79 residues, representing approximately 14% of the butyrylcholinesterase linear sequence, and result in the expression of about 1500 distinct butyrylcholinesterase variants.

Libraries of nucleic acids corresponding to the seven regions of human butyrylcholinesterase to be mutated are synthesized by codon-based mutagenesis, as described above and as depicted schematically in FIG. 7. Briefly, multiple DNA synthesis columns are used for synthesizing the oligonucleotides by β-cyanoethyl phosphoramidite chemistry, as described previously by Glaser et al., supra, 1992. In the first step, trinucleotides encoding for the amino acids of butyrylcholinesterase are synthesized on one column while a second column is used to synthesize the trinucleotide NN(G/T), where N is a mixture of dA, dG, dC, and, dT cyanoethyl phosphoramidities. Using the trinucleotide NN(G/T) results in thorough mutagenesis with minimal degeneracy, accomplished through the systematic expression of all twenty amino acids at every position.

Following the synthesis of the first codon, resins from the two columns are mixed together, divided, and replaced in four columns. By adding additional synthesis columns for each codon and mixing the column resins in the manner illustrated in FIG. 7, pools of degenerate oligonucleotides will be segregated based on the extent of mutagenesis. The resin mixing aspect of codon-based mutagenesis makes the process rapid and cost-effective because it eliminates the need to synthesize multiple oligonucleotides. In the present study, the pool of oligonucleotides encoding single amino acid mutations is used to synthesize focused butyrylcholinesterase libraries.

The oligonucleotides encoding the butyrylcholinesterase variants containing a single amino acid mutation is cloned into the doublelox targeting vector using oligonucleotide-directed mutagenesis (Kunkel, supra, 1985). To improve the mutagenesis efficiency and diminish the number of clones expressing wild-type butyrylcholinesterase, the libraries are synthesized in a two-step process. In the first step, the butyrylcholinesterase DNA sequence corresponding to each library site is deleted by hybridization mutagenesis. In the second step, uracil-containing single-stranded DNA for each deletion mutant, one deletion mutant corresponding to each library, is isolated and used as template for synthesis of the libraries by oligonucleotide-directed mutagenesis. This approach has been used routinely for the synthesis of antibody libraries and results in more uniform mutagenesis by removing annealing biases that potentially arise from the differing DNA sequence of the mutagenic oligonucleotides. In addition, the two-step process decreases the frequency of wild-type sequences relative to the variants in the libraries, and consequently makes library screening more efficient by eliminating repetitious screening of clones encoding wild-type butyrylcholinesterase.

The quality of the libraries and the efficiency of mutagenesis is characterized by obtaining DNA sequence from approximately 20 randomly selected clones from each library. The DNA sequences demonstrate that mutagenesis occurs at multiple positions within each library and that multiple amino acids were expressed at each position. Furthermore, DNA sequence of randomly selected clones demonstrates that the libraries contain diverse clones and are not dominated by a few clones.

Optimization of Transfection Parameters for Site-Specific Integration

Optimization of transfection parameters for Cre-mediated site-specific integration was achieved utilizing Bleomycin Resistance Protein (BRP) DNA as a model system.

Cre recombinase is a well-characterized 38-kDa DNA recombinase (Abremski et al., Cell 32:1301–1311 (1983)) that is both necessary and sufficient for sequence-specific recombination in bacteriophage P1. Recombination occurs between two 34-base pair loxP sequences each consisting of two inverted 13-base pair recombinase recognition sequences that surround a core region (Sternberg and Hamilton, J. Mol. Biol. 150:467–486 (1981a); Sternberg and Hamilton, J. Mol. Biol., 150:487–507 (1981b)). DNA cleavage and strand exchange occurs on the top or bottom strand at the edges of the core region. Cre recombinase also catalyzes site-specific recombination in eukaryotes, including both yeast (Sauer, Mol. Cell. Biol. 7:2087–2096 (1987)) and mammalian cells (Sauer and Henderson, Proc. Natl. Acad. Sci. USA, 85:5166–5170 (1988); Fukushige and Sauer, Proc. Natl. Acad. Sci. U.S.A. 89:7905–7909 (1992); Bethke and Sauer, Nuc. Acids Res., 25:2828–2834 (1997)).

Calcium phosphate transfection of 13-1 cells was previously demonstrated to result in targeted integration in 1% of the viable cells plated (Bethke and Sauer, Nuc. Acids Res., 25:2828–2834 (1997)). Therefore, initial studies were conducted using calcium phosphate to transfect 13-1 cells with 4 μg pBS185 and 10, 20, 30, or 40 μg of pBS397-fl(+)/BRP. The total level of DNA per transfection was held constant using unrelated pBluescript II KS DNA (Stratagene; La Jolla, Calif.), and transformants were selected 48 hours later by replating in media containing 400 μg/ml geneticin. Colonies were counted 10 days later to determine the efficiency of targeted integration. Optimal targeted integration was typically observed using 30 μg of targeting vector and 4 μg of Cre recombinase vector pBS185, consistent with the 20 μg targeting vector and 5 μg of pBS185 previously reported (Bethke and Sauer, Nuc. Acids Res., 25:2828–2834 (1997)). The frequency of targeted integration observed was generally less than 1%. Despite the sensitivity of the calcium phosphate methodology to the amount of DNA used and the buffer pH, targeted integration efficiencies observed were sufficient to express the protein libraries.

As shown in Table 3, several cell lines as well as other transfection methods were also characterized. As disclosed herein, Flp recombinase also can be used to target insertion of exogenous DNA into a particular site in the genome as described by Dymecki, supra, 1996. The target site for Flp recombinase consists of 13 base-pair repeats separated by an 8 base-pair spacer: 5'-GAAGTTCCTATTC[TCTAGAAA]GTATAGGAACTTC-3'. Briefly, variant libraries corresponding to the region of butyrylcholinesterase corresponding to amino acids 327 to 332 of butyrylcholinesterase (shown as region 6 in Table 2) were transfected into mammalian cells using flp recombinase and the 293T cell line. The butyrylcholinesterase variants designated SEQ ID NOS: 2, 4, 6 and 8 were identified and characterized using the methods described herein utilizing Flp recombinase and the 293T human cell line.

In general, lipid-mediated transfection methods are more efficient than methods that alter the chemical environment, such as calcium phosphate and DEAE-dextran transfection. In addition, lipid-mediated transfections are less affected by contaminants in the DNA preparations, salt concentration, and pH and thus generally provide more reproducible results (Felgner et al., Proc. Natl. Acad. Sci. USA, 84:7413–7417 (1987)). Consequently, a formulation of the neutral lipid dioleoyl phosphatidylethanolamine and a cationic lipid, termed GenePORTER transfection reagent (Gene Therapy Systems; San Diego, Calif.), was evaluated as an alternative transfection approach. Briefly, endotoxin-free DNA was prepared for both the targeting vector pBS397-fl(+)/BRP and the Cre recombinase vector pBS185 using the EndoFree Plasmid Maxi kit (QIAGEN; Valencia, Calif.). Next, 5 μg pBS185 and varying amounts of pBS397-fl(+)/BRP were diluted in serum-free medium and mixed with the GenePORTER transfection reagent. The DNA/lipid mixture was then added to a 60–70% confluent monolayer of 13-1 cells consisting of approximately $5 \times 10^5$ cells/100-mm dish and incubated at 37° C. Five hours later, fetal calf serum was added to 10%, and the next day the transfection media was removed and replaced with fresh media.

Transfection of the cells with variable quantities of the targeting vector yielded targeted integration efficiencies ranging from 0.1% to 1.0%, with the optimal targeted integration efficiency observed using 5 μg each of the targeting vector and the Cre recombinase vector. Lipid-based transfection of the 13-1 host cells under the optimized conditions resulted in 0.5% targeted integration efficiency being consistently observed. A 0.5% targeted integration is slightly less than the previously reported 1.0% efficiency (Bethke and Sauer, Nuc. Acids Res., 25:2828–2834 (1997)), and is sufficient to express large protein libraries and allows expressing libraries of protein variants in mammalian cells.

TABLE 3

Expression of a single butyrylcholinesterase variant per cell using either stable or transient cell transfection.

| Cell Line | Expression | Integration Method | Integration? (PCR) | Integration? (Activity) |
|---|---|---|---|---|
| NIH3T3 (13-1) | Transient (lipid-based) | N/A | N/A | Transient, very low activity |
| NIH3T3 (13-1) | Stable | Cre recombinase | Yes | No measurable activity |
| CHO | Transient (lipid-based) | N/A | N/A | Transient, measurable activity (colorimetric and cocaine hydrolysis) |
| 293 | Transient (lipid-based) | N/A | N/A | Transient, measurable activity (colorimetric and cocaine hydrolysis) |
| 293 | Stable | Flp recombinase | Yes | Measurable activity (colorimetric and cocaine hydrolysis) |

These results demonstrate optimization of transfection conditions for targeted insertion in NIH3T3 13-1 cells. Conditions for a simple, lipid-based transfection method that required a small amount of DNA and generated reproducible 0.5% targeting efficiency were established.

Expression of Butyrylcholinesterase Variant Libraries in Mammalian Cells

Each of the seven libraries of butyrylcholinesterase variants are transformed into a host mammalian cell line using the doublelox targeting vector and the optimized transfection conditions described above. Following Cre-mediated transformation the host cells are plated at limiting dilutions to isolate distinct clones in butyrylcholinesterase variants integrated in the Cre/lox targeting site are selected with geneticin. Subsequently, the DNA encoding butyrylcholinesterase variants from 20–30 randomly selected clones from each library are sequenced and analyzed as described above. Briefly, total cellular DNA is isolated from about $10^4$ cells of each clone of interest using DNeasy Tissue Kits (Qiagen, Valencia, Calif.). Next, the butyrylcholinesterase gene is amplified using PfuTurbo DNA polymerase (Stratagene; La Jolla, Calif.) and an aliquot of the PCR product is then used for sequencing the DNA encoding butyrylcholinesterase variants from randomly selected clones by the fluorescent dideoxynucleotide termination method (Perkin-Elmer, Norwalk, Conn.) using a nested oligonucleotide primer.

As described previously, the sequencing demonstrates uniform introduction of the library and the diversity of mammalian transformants resembles the diversity of the library in the doublelox targeting vector following transformation of bacteria.

TABLE 4

Relative Activity of butyrylcholinesterase variants (WT = 1) with enhanced cocaine hydrolase activity and corresponding codon changes.

| | | |
|---|---|---|
| Wild-type | | 1 |
| A199S | GCA to TCA | 2.5 |
| F227A | TTT to GCG | 4.1 |
| F227G | TTT to GGG | 4.0 |
| F227S | TTT to AGT | 2.3 |
| F227P | TTT to CCG | 2.9 |
| F227T | TTT to ACT | 1.9 |
| F227C | TTT to TGT | 1.9 |
| F227M | TTT to ATG | 1.4 |
| P285Q | CCT to CAG | 2.4 |
| P285S | CCT to AGC | 1.9 |
| S287G | TCA to GGT | 4.1 |
| A328W | GCT to TGG | 7 |
| V331L | GTC to TTG | n.d |
| Y332S | TAT to TCG | n.d |
| Y332M | TAT to ATG | n.d |
| Y332P | TAT to CCA | n.d |
| A328W/Y332M/S287G/F227A/A199S | | 100 |
| A328W/S287G/F227A/A199S | | 100 |
| A328W/S287G/A199S | | 97 |
| A328W/S287G/F227A | | 91 |
| A328W/F227A | | 68 |
| A328W/Y332M | | 24 |
| A328W/Y332P | | 10 |
| A328W/V331L | | 16 |
| A328W/Y332S | | 8 |

As described herein, a library corresponding to region five of butyrylcholinesterase was expressed and individual variants were screened by measuring the hydrolysis of [$^3$H]-cocaine using the microtiter assay. The catalytic efficiency ($V_{max}/K_m$) of variants with enhanced activity were characterized using the microtiter assay to determine their relative $K_m$ and $V_{max}$. Twenty-one butyrylcholinesterase variants were identified that have enhanced cocaine hydrolase activity: A328W/Y332M(SEQ ID NO: 2), A328W/Y332P (SEQ ID NO: 4), A328W/V331L (SEQ ID NO: 6) and A328W/Y332S(SEQ ID NO: 8), A328W/Y332M/S287G/F227A/A199S (SEQ ID NO: 10), A328W/S287G/F227A/A199S (SEQ ID NO: 12), A328W/S287G/A199S (SEQ ID NO: 14), A328W/S287G/F227A (SEQ ID NO: 16), A328W/F227A (SEQ ID NO: 18), Y322S (SEQ ID NO: 20), Y332M (SEQ ID NO: 22), Y332P (SEQ ID NO: 24), V331L (SEQ ID NO: 26), F227A (SEQ ID NO: 28), F227G (SEQ ID NO: 30), F227S (SEQ ID NO: 32), F227P (SEQ ID NO: 34), F227T (SEQ ID NO: 36), F227C (SEQ ID NO: 38), F227M (SEQ ID NO: 40), A199S (SEQ ID NO: 42).

EXAMPLE III

Characterization of Butyrylcholinesterase Variants that Display Enhanced Cocaine Hydrolysis Activity This example describes the molecular characterization of butyrylcholinesterase variants that display enhanced cocaine hydrolysis activity in the microtiter assay described below. The cocaine hydrolysis activity measured in the microtiter assay format is further confirmed using greater amounts of the butyrylcholinesterase variants of interest. In addition to the microtiter-based assay, the activity of the clones is demonstrated in solution phase with product formation measured by the HPLC assay to verify the increased cocaine hydrolysis activity of the butyrylcholinesterase variants and confirm that the enhanced hydrolysis is at the benzoyl ester group.

The kinetic constants for wild-type butyrylcholinesterase and the best variants are determined and used to compare the catalytic efficiency of the variants relative to wild-type butyrylcholinesterase. $K_m$ values for (−)-cocaine are determined at 37° C. $V_{max}$ and $K_m$ values are calculated using Sigma Plot (Jandel Scientific, San Rafael, Calif.). The number of active sites of butyrylcholinesterase is determined by the method of residual activity using echothiopate iodide or diisopropyl fluorophosphates as titrants, as described previously by Masson et al., *Biochemistry* 36: 2266–2277 (1997). Alternatively, the number of butyrylcholinesterase active sites is estimated using an ELISA to quantitate the mass of butyrylcholinesterase or butyrylcholinesterase variants present in culture supernatants. Purified human butyrylcholinesterase is used as the standard for the ELISA quantitation assay. The catalytic rate constant, $k_{cat}$, is calculated by dividing $V_{max}$ by the concentration of active sites. Finally, the catalytic efficiencies of the best variants are compared to wild-type butyrylcholinesterase by determining $k_{cat}/K_m$ for each butyrylcholinesterase variant.

In order to better characterize all the clones expressing butyrylcholinesterase variants with increased cocaine hydrolysis activity, the DNA encoding the variants is sequenced. DNA sequencing reveals the precise location and nature of the mutations and thus, quantifies the total number of distinct butyrylcholinesterase variants identified. Screening of each library is complete when clones encoding identical butyrylcholinesterase mutations are identified on multiple occasions, indicating that the libraries have been screened exhaustively.

EXAMPLE IV

Synthesis and Characterization of Combinatorial Butyrylcholinesterase Variant Libraries This example demonstrates synthesis and characterization of combinatorial libraries of butyrylcholinesterase variants expressed in mammalian cells.

The beneficial mutations identified from screening libraries of butyrylcholinesterase variants containing a single amino acid mutation are combined in vitro to further improve the butyrylcholinesterase cocaine hydrolysis activity. The positive combination of beneficial mutations designated biochemical additivity has been observed on multiple occasions. For example, the iterative process of increasing antibody affinity in a stepwise fashion through the accumulation and subsequent combination of beneficial mutations has led to the identification of antibodies displaying 500-fold enhanced affinity using variant libraries containing less than 2,500 distinct variants. Importantly, the principle of biochemical additivity is not restricted to improving the affinity of antibodies, and has been exploited to achieve improvements in other physical properties, such as thermostability, catalytic efficiency, or enhanced resistance to pesticides.

The best mutations identified from screening the seven focused butyrylcholinesterase libraries are used to synthesize a combinatorial library. The number of distinct variants in the combinatorial library is expected to be small, typically a fraction of the number of distinct variants from the initial libraries. For example, combinatorial analysis of single mutations at eight distinct sites would require a library that contains $2^8$, or 256, unique variants. The combinatorial library is synthesized by oligonucleotide-directed mutagenesis, characterized, and expressed in the mammalian host cell line. Variants are screened and characterized as described above. DNA sequencing reveals additive mutations.

EXAMPLE V

Expression and Purification of Butyrylcholinesterase Variants

This example demonstrates the expression in a mammalian cell line and subsequent purification of butyrylcholinesterase variants.

Clones expressing the most catalytically active butyrylcholinesterase variants, as well as wild-type butyrylcholinesterase, are used to establish larger-scale cultures in order to purify quantities of the enzyme necessary for in vivo studies. It is estimated that approximately 100 mg each of wild-type butyrylcholinesterase and the optimal variant is required to complete the in vivo toxicity and addiction studies in rats as described below.

The butyrylcholinesterase variants of interest are cloned into the pCMV/Zeo vector (Invitrogen, Carlsbad, Calif.) using unique restriction sites. The cloning of the variants is verified using restriction mapping and DNA sequencing. Subsequently, the variants are expressed in transfected Chinese Hamster ovary cells CHO Kl(ATCC CCL 61). CHO cells were selected for expression because butyrylcholinesterase is a glycoprotein and these cells have been previously used for the expression of recombinant human therapeutic glycoproteins (Goochee et al., *Biotechnology* 9:1347–1355 (1991); Jenkins and Curling, *Enzyme Microb. Technol.* 16:354–364 (1994)) as well as fully active recombinant butyrylcholinesterase (Masson et al., supra, 1997). Initially, the CHO cells are transiently transfected with all the butyrylcholinesterase variants to confirm expression of functional butyrylcholinesterase. Subsequently, the cells are stably transfected and clones expressing butyrylcholinesterase variants are selected using the antibiotic Zeocin (Invitrogen. Carlsbad, Calif.). Colonies are picked with a sterile cotton-tipped stick and transferred to 24-well plates. The butyrylcholinesterase expression is measured and the colonies with the highest activity are further expanded. The kinetic constants of the butyrylcholinesterase variants are determined to ensure that expression in CHO cells does not diminish the enzymatic activity compared to butyrylcholinesterase variants expressed in NIH3T3 cells.

The cells are expanded in T175 flasks and expanded further into multiple 3 L spinner flasks until approximately $5 \times 10^8$ cells are obtained. Subsequently, the cell lines are transferred to CELL-PHARM System 2000 hollow fiber cell culture systems (Unisyn Technologies, Hopkinton, Mass.) for the production and continuous recovery of butyrylcholinesterase. The hollow fiber system permits high cell densities to be obtained ($10^8$/ml) from which 60–120 ml of concentrated butyrylcholinesterase is harvested each day. It is anticipated that it requires one month to produce sufficient quantities of butyrylcholinesterase for further evaluation.

The concentrated recombinant butyrylcholinesterase harvested from the hollow fiber systems are purified, essentially as described previously (Masson et al., supra, 1997). The serum-free medium is centrifuged to remove particulates, its ionic strength is reduced by dilution with two volumes of water, and subsequently, the sample is loaded on a procainamide Sepharose affinity column. Butyrylcholinesterase is eluted with procainamide, purified further by ion exchange chromatography and concentrated. A recombinant butyrylcholinesterase mutant expressed in CHO cells has previously been enriched to 99% purity with over 50% yields using this purification approach (Lockridge et al., *Biochemistry* 36:786–795 (1997)). The enzyme is filter-sterilized through a 0.22-$\mu$m membrane and stored at 4° C. Under these conditions, butyrylcholinesterase retains over 90% of its original activity after 18 months (Lynch et al., *Toxicology and Applied Pharmacol.* 55:83–91 (1999)).

EXAMPLE VI

Evaluation of Wild-Type Butyrylcholinesterase and Butyrylcholinesterase Variants This example describes the evaluation of wild-type butyrylcholinesterase and butyrylcholinesterase variants in rat cocaine toxicity and reinforcement models.

Butyrylcholinesterase variants that display increased cocaine hydrolysis activity in vitro display greater potency for the treatment of cocaine toxicity and addiction in vivo. To characterize the butyrylcholinesterase variants in vivo, an acute overdose model is used to measure the potency of butyrylcholinesterase variants for toxicity, while models of reinforcement and discrimination are used to predict the potency of butyrylcholinesterase variants for the treatment of addiction. Although the pharmacokinetics of human butyrylcholinesterase variants are not expected to be optimal in models, the rat cocaine models are well characterized and require significantly smaller quantities of purified butyrylcholinesterase than do primate models. It is anticipated that both wild-type butyrylcholinesterase and the butyrylcholinesterase variants with increased cocaine hydrolysis activity display dose-dependent responses. Furthermore, the butyrylcholinesterase variant optimized for cocaine hydrolysis activity are efficacious at substantially smaller doses than the wild-type butyrylcholinesterase.

Modification of the Toxicity of Cocaine

The effect of butyrylcholinesterase variants on cocaine toxicity is evaluated as previously described in rat model of overdose by Mets et al., *Proc. Nat. Acad. Sci. USA* 95:10176–10181 (1998). This model uses co-infusion of catecholamines because variable endogenous catecholamine levels have been shown to affect cocaine toxicity (Mets et al., *Life Sci.* 59:2021–2031 (1996)). Infusion of cocaine at 1 mg/kg/min produces $LD_{50}$=10 mg/kg and $LD_{90}$=16 mg/kg when the levels of catecholamines are standardized.

Six groups of six rats each are used in this study. The rats are Sprague-Dawley males, weighing 250–275 g upon receipt in the vivarium, which is maintained on a 12 hour light-dark cycle. The rats have food and water available ad libitum at all times. Prior to treatment the rats are fitted with femoral arterial and venous catheters and permitted to recover. Subsequently, the rats are treated with varying amounts of the butyrylcholinesterase variants (0.35, 1.76, or 11.8 mg/kg) or equivalent volumes of saline 15 minutes prior to the co-infusion of catecholamines and cocaine (1 mg/kg/min). The infusion is for 16 minutes to deliver the $LD_{90}$ of cocaine, unless the animals expire sooner. Based on the relative catalytic efficiencies of wild-type butyrylcholinesterase and the previously described catalytic antibody (Mets et al., supra, 1998), it is anticipated that increasing doses of butyrylcholinesterase confer increased survival rate to the rats relative to the saline controls and that the highest butyrylcholinesterase dose (11.8 mg/kg) protects all the animals. A butyrylcholinesterase variant that hydrolyzes cocaine 10-fold more efficiently in vitro is be expected to confer protection to all of the animals at a lower dose (1 mg/kg, for example).

Modification of the Abuse of Cocaine

The discriminative and reinforcing pharmacological effects of cocaine are believed to most closely reflect the actions of cocaine that embody abuse of the drug. Therefore, the butyrylcholinesterase variants are evaluated in both cocaine reinforcement and cocaine discrimination models in rats.

The rat model of the reinforcing effects of cocaine has been used extensively to evaluate other potential therapies for cocaine (Koob et al., *Neurosci. Lett.* 79: 315–320(1987); Hubner and Moreton, *Psychopharmacology* 105: 151–156 (1991); Caine and Koob, *J. Pharmacol. Exp. Ther.* 270:209–218 (1994); Richardson et al., *Brain Res.* 619: 15–21 (1993)).

Male Sprague-Dawley rats are maintained as described above. Six operant chambers (Med Associates, St. Albans, Vt.), equipped with a house light, retractable lever, dipper mechanism, red, yellow, and green stimulus lights, and a pneumatic syringe-drive pump apparatus (IITC Life Sciences, Inc., Woodland Hills, Calif.) for drug delivery are interfaced with an IBM-compatible computer through input and output cards (Med Associates, Inc., St. Albans, Vt.). The chambers are housed within an air conditioned, sound attenuating cubicle (Med Associates). Custom self-administration programs, controlling scheduled contingencies and stimulus arrays within the operant chambers, are written using the Med-PC programming language for DOS.

The reinforcing effects of cocaine are assessed in a model that quantitates the number of injections taken by rats under conditions in which intravenous administration is contingent upon a response made by the animal (Mets et al., supra, 1998). The rats are trained in the operant conditioning chambers to press a lever in order to gain access to 0.5 ml of a sweetened milk solution. After the rats have acquired the lever-press response on a fixed-ratio 1 (FR1) schedule of reinforcement, the response requirements are successively increased to an FR5 schedule. When the rats display stable rates of milk-maintained responding over three consecutive days on this schedule (less than 10% variability in reinforcer deliveries over the one-hour session) a catheter is surgically introduced in the left internal jugular vein and the rats are given a minimum of two days to recover from surgery.

On the first operant training session following surgery, rats are allowed to respond on the lever, in a one-hour session, for the simultaneous 5-second delivery of both milk and an intravenous bolus of cocaine (0.125 mg/kg/injection). The milk is then removed from the chamber and for the next three days, the rats are given access to one of three doses of cocaine (0.125, 0.25, or 0.5 mg/kg/injection) for one hour each, in self-administration sessions six hours in duration. Thus, the rats are allowed access to each dose twice per session and the doses are presented in repeated ascending order (i.e., 0.125, 0.25, 0.5, 0.125, 0.25, 0.5 mg/kg/injection). Within each one-hour long dose-component, the original FR5 schedule with a 10-second timeout is retained. In addition, 10-minute timeout periods are instituted after each dose component in an attempt to minimize carryover effects across the individual one-hour sessions.

When the rats display consistent cocaine self-administration (over 160 injections per six-hour session with less than 15% variability) over three consecutive days, they are placed on a schedule in which smaller doses, as well as saline, are available during single daily sessions. Each session is divided into two components, with saline and three doses of cocaine available in each component. The first component of each session provides access to a series of low doses (0–0.0625 mg/kg/injection) while the second component provides access to a wider range of doses (0–0.5 mg/kg/injection).

After the rates of cocaine self-administration are stabilized the rats are divided between six groups and each group (n=6 rats) is given 0.35, 1.76, or 11.8 mg/kg of either wild-type butyrylcholinesterase, the optimized butyrylcholinesterase variant or an equivalent volume of saline 30 minutes prior to the beginning of the daily self-administration sessions. The effects of the pretreatment are monitored for several days until the cocaine self-administration behavior of the rat returns to baseline.

Using a fixed ratio (FR) schedule, the number of injections is limited only by the duration of the session and consequently, the number of injections is used as the dependent variable to compare the potency of optimized butyrylcholinesterase with wild-type butyrylcholinesterase. Following administration of varying concentrations of wild-type butyrylcholinesterase or the optimized butyrylcholinesterase variant, the dose response curves are analyzed using a mixed factor MANOVA. The butyrylcholinesterase concentration (0.35, 1.76, or 11.8 mg/kg) is loaded as the between-subjects factor and the cocaine dose (0, 0.015, 0.03, 0.06, 0.125, 0.25, 0.5 mg/kg/injection) is loaded as the within-subjects factor. All individual comparisons across butyrylcholinesterase treatment groups at individual cocaine doses use the Tukey HSD post-hoc procedure (see Gravetter, F. J. and Wallnau, L. B., Statistics for the Behavioural Sciences (5th ed., 2000, Wadsworth Publ., Belmont, Calif.)) and the criterion for statistical significance is set at $p<0.05$. At higher butyrylcholinesterase doses (11.8 mg/kg), the number of injections taken by the rats is expected to be lower than the untreated (saline) control group. Furthermore, rats treated with the butyrylcholinesterase variant displaying enhanced cocaine hydrolysis are expected to reduce their number of injections at a smaller dose (0.35 mg/kg) than the animals treated with the wild-type butyrylcholinesterase.

Drug discrimination is relevant to the subjective effect of cocaine in clinical situations and antagonism of cocaine discrimination following pretreatment is considered clear evidence of therapeutic potential (Holtzman, *Modern Methods in Pharmacology, Testing and Evaluation of Drug Abuse*, Wiley-Liss Inc., New York, (1990); Spealman, *NIDA Res. Mon.* 119: 175–179 (1992)). The most frequently used procedure to establish and evaluate the discriminative stimulus effect of drugs is to train animals in a controlled operant procedure to use the injected drug as a stimulus to control distribution of responding on two levers. Dose-effect curves consisting of distribution of the responses on the "drug-associated" lever as a function of drug dose are easily generated. These cocaine dose-effect curves can be altered by the administration of a competitive antagonist. The amount of the shift of the curve and time required for the original sensitivity of the animal to cocaine to return are useful data for evaluating the potential therapeutic use of wild-type butyrylcholinesterase and the optimized variant. The discriminative stimulus effects of cocaine in rat models have been used to evaluate the therapeutic potential of 5 dopamine reuptake inhibitors, as well as agonists and antagonists to the dopamine receptors (Witkin et al., *J. Pharmacol. Exp. Ther.* 257: 706–713 (1989); Kantak et al., *J. Pharmacol. Exp. Ther.* 274: 657–665 (1995); Barret and Appel, *Psychopharmacology* 99: 13–16 (1989); Callahan et al., *Psychopharmacology* 103: 50–55 (1991)).

A multiple trial procedure for training and testing cocaine as a discriminative stimulus is used to evaluate the potency of butyrylcholinesterase in rats as previously described in Bertalmio et al. J. Pharmacol. Methods 7: 289–299 (1982) and Schecter, *Eur. J. Pharmacol.* 326: 113–118 (1997). A dose-response curve for cocaine is obtained in a single session in the presence of butyrylcholinesterase or the optimized butyrylcholinesterase variant. Subsequently, the recovery of the rat's original sensitivity to cocaine is tracked on a twice-weekly basis to assess the duration of action of the butyrylcholinesterase.

The rats are deprived to 80% of their free-feeding weight at the beginning of the experiment in order to train them in the food-reinforced operant procedure. Each rat is placed in an operant conditioning chamber equipped with two light stimuli and two retractable levers, one on either side of a milk delivery system and trained to press on one of the levers to receive access to 0.5 ml of sweetened condensed milk. Once the rats have learned to respond on this lever, a multiple-trials procedure is initiated. Each session consists of 6 trials with each trial lasting 15 minutes. The first 10 minutes of each trial are a blackout period, during which no lights are on and responding has no consequence. This 10-minute period allows for drug absorption in the subsequent testing phases of the study. The last 5 minutes of each trial are a milk-reinforced period (FR5). Once the rats respond consistently and rapidly during the 5-minute response period (signaling period), cocaine is introduced into the procedure.

Initially, 10 mg/kg cocaine is given 10 minutes prior to the beginning of three of six weekly sessions. During these sessions, the "non-cocaine" lever (saline) previously extended is retracted and the other, "cocaine-associated," lever is extended on the other side of the milk delivery cup. Responses (initially only a single response; eventually five responses) on this second lever result in milk presentation if cocaine was administered prior to the session. The rats are being trained to respond on the second lever if they detect the interoceptive effects of the administered cocaine. Because cocaine's interoceptive effects are not believed to extend beyond 30 minutes, the sessions following cocaine administration lasts for only two trials (15 minutes each). At this juncture the rats do not receive a cocaine injection on three days of the week and on those days they are reinforced with milk (FR5) for responding on the available non-cocaine lever during the signaling periods of six trials. On the remaining three days of the week, the rats are given 10 mg/kg cocaine before the beginning of the session and are reinforced for responding on the available cocaine lever during the signaling periods on each of two trials.

Subsequently, each daily session is initiated with one to four trials without cocaine administration, followed by the administration of 10 mg/kg cocaine. Thus, each session ends with two trials in which responding on the cocaine-appropriate lever is required for food delivery. Although only the "correct" levers are extended during this phase, the critical step of making both levers available during the entire session is taken as soon as the animals learn to switch from the non-cocaine to the cocaine lever within daily sessions. Subsequently, each session begins with a 10-minute blackout period followed by presentation of both levers for five minutes. During the first 1 to 4 trials of a daily session, no cocaine is given, and 5 consecutive responses on the non-cocaine lever result in food during this 5-minute period. If the rat switches from one lever to the other or responds on the incorrect lever, he does not get reinforced and both levers are retracted for 10 seconds, at which time the levers are presented again and the trial restarted. At the start of the second, third, or fourth trial, 10 mg/kg cocaine are given and the rat is returned to the test box. When the light is illuminated and the levers presented on the next two trials, five consecutive responses on the cocaine lever are required for milk presentation to demonstrate that the rats are learning to switch their responding from the non-cocaine lever to the cocaine lever using the interoceptive effects of cocaine as a cue to tell them which lever is correct on a given trial.

A cocaine dose-effect curve is obtained as soon as the rats meet criterion of 80% correct lever selection on three consecutive sessions. On the first trial of a test session, saline is given. On subsequent trials, 0.1, 0.3, 1.0, 3.2, and 10 mg/kg cocaine is administered, each at the start of the 10 minute blackout that begins each trial. During these test trials, five consecutive responses on either lever result in milk presentation, but switching from one lever to the other prior to completion of an FR results in lever retraction for 10 seconds. It is anticipated that animals begin this session with responses on the non-cocaine lever and gradually increase the percent of responses made on the cocaine lever until all responses are made on that lever. Thus, a dose-response curve of lever selection versus dose of cocaine administered is established during each test session.

Once cocaine has been established as a discriminative stimulus, the rats are placed in separate groups (n=6 per group) that receive 0.35, 1.76, or 11.8 mg/kg of either wild-type butyrylcholinesterase or the optimized variant. The discriminative stimulus effects of cocaine is determined 30 minutes following enzyme administration and daily afterwards until sensitivity to cocaine is re-established. On the initial test session following administration of butyrylcholinesterase, larger doses of cocaine are given if there is no selection of the cocaine lever following any of the smaller test doses. Doses as large as 100 mg/kg cocaine are given if the animals fail to select the cocaine-appropriate lever following administration of 10 or 32 mg/kg cocaine. Because dose-response curves to cocaine can be obtained in a single session, this protocol provides information on the relative ability of the two types of butyrylcholinesterase to decrease the potency of cocaine as a discriminative stimulus, which is a relevant aspect of its abuse liability. The butyrylcholinesterase variant displaying enhanced cocaine hydrolysis activity in vitro is more potent.

EXAMPLE VII

In Vivo Confirmation of the Therapeutic Effect of Butyrylcholinesterase Variant on Cocaine-Toxicity This example describes the confirmation, in vivo, of the therapeutic effect of butyrylcholinesterase variants provided by the invention on cocaine toxicity.

Briefly, unilateral/bilateral jugular cannulations were performed under isoflurane anesthesia (max. 20 min) on 350 g male Sprague Dawley®SD® rats (Harlan Sprague Dawley, Inc.) The animals were allowed to recover for 24 hours before studies commenced. For in vivo confirmation of the therapeutic effect on cocaine toxicity of butyrylcholinesterase variant designated A328W/Y332M/S287G/F227A (SEQ ID NO: 52), wild-type BChE (10–50 mg/kg) or the A328W/Y332M/S287G/F227A variant (0.1–0.5 mg/kg) was injected intravenously, then flushed with 200 ml saline. One minute later, the cannula was connected to an infusion pump (Harvard Apparatus) and cocaine (HCl salt) was infused at 6 mls/hr (2 mg/kg/min) for 15 minutes corresponding to a total dose equal to 30 mg/kg. The time-to-onset for slight convulsions, strong convulsions and death were recorded. In pilot studies, the lethal dose of cocaine was determined to be approximately 25 mg/kg. In a second series of studies, 0.5 mg/kg of the A328W/Y332M/S287G/F227A variant was administered at various time points after initiation of the 30 mg/kg cocaine infusion and gross observations recorded. As demonstrated in FIG. 8, which shows the effect of pre-treatment with the A328W/Y332M/S287G/F227A variant (solid circles) or wild-type BChE (open circles) on cocaine-induced toxicity, the A328W/Y332M/S287G/F227A variant exhibited statistically significant protection against cocaine (Chi-squared test; $p<0.001$).

FIG. 9 further demonstrates the therapeutic effect on cocaine-induced toxicity of the variant, by showing that the A328W/Y332M/S287G/F227A variant provided full protection when administered at 8 minutes into the cocaine infusion (i.e. after the first set of slight convulsions) and decreased in ability to protect when administered at later time points.

Figure 10:
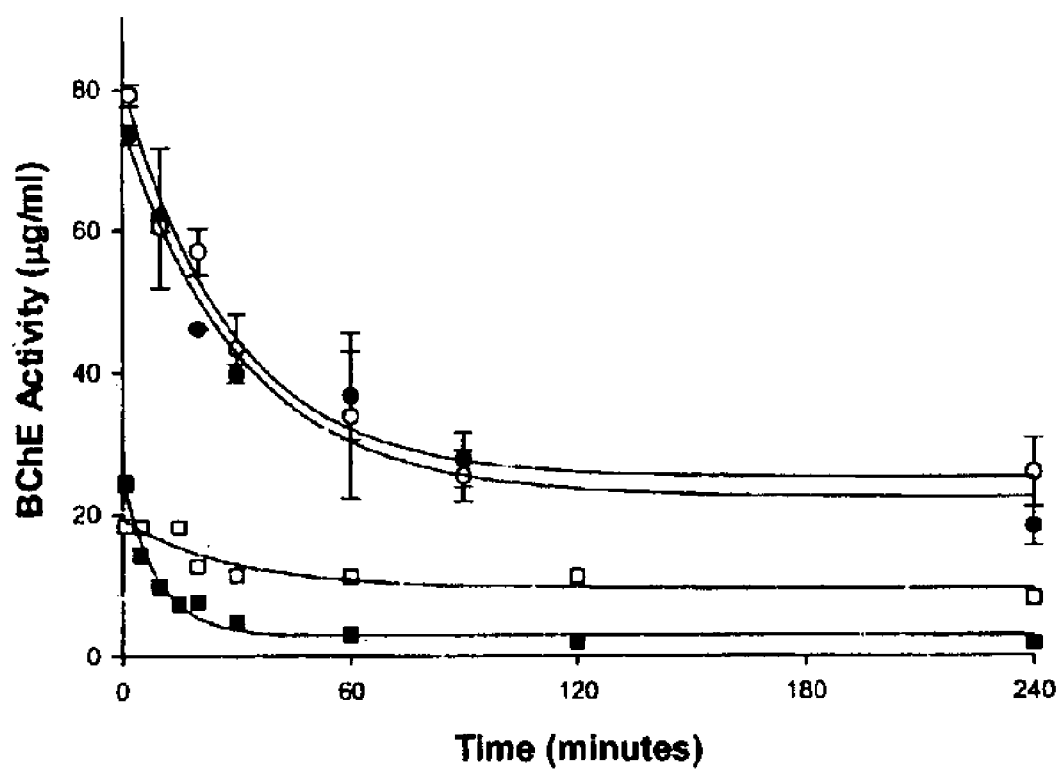
FIG. 10 shows plasma levels of wt BChE and AME-359 following an i.v. bolus of 1 mg/kg. Wild-type BChE pool I or pool II (open squares and open circles, respectively) and AME-359 pool I or pool II (solid squares and solid circles, respectively). BChE activity was determined by enzymatic assay utilizing butyrylthiocholine as the substrate.

For pharmacokinetic studies cannulated rats were injected with wild-type BChE and the A328W/Y332M/S287G/F227A variant at 1 mg/kg and plasma was collected at the indicated timepoints. Plasma was analyzed for BChE activity using a standard assay for BChE utilizing butyrylthiocholine as the substrate. In a separate set of studies, a 10 mg/kg i.v. bolus of cocaine was administered followed immediately by the A328W/Y332M/S287G/F227A variant (0.01, 0.02 or 0.5 mg/kg) and plasma collected at the indicated time points. Circulating cocaine levels in these samples were determined by ELISA (Immunalysis, Pomona, Calif.). FIG. 10 shows the plasma levels of wt BChE and the A328W/Y332M/S287G/F227A variant following an intravenous bolus of 1 mg/kg. Wild-type BChE pool I or pool II (open squares and open circles, respectively) and the A328W/Y332M/S287G/F227A variant pool I or pool II (solid squares and solid circles, respectively). BChE activity was determined by enzymatic assay utilizing butyrylthiocholine as the substrate.

Figure 11:
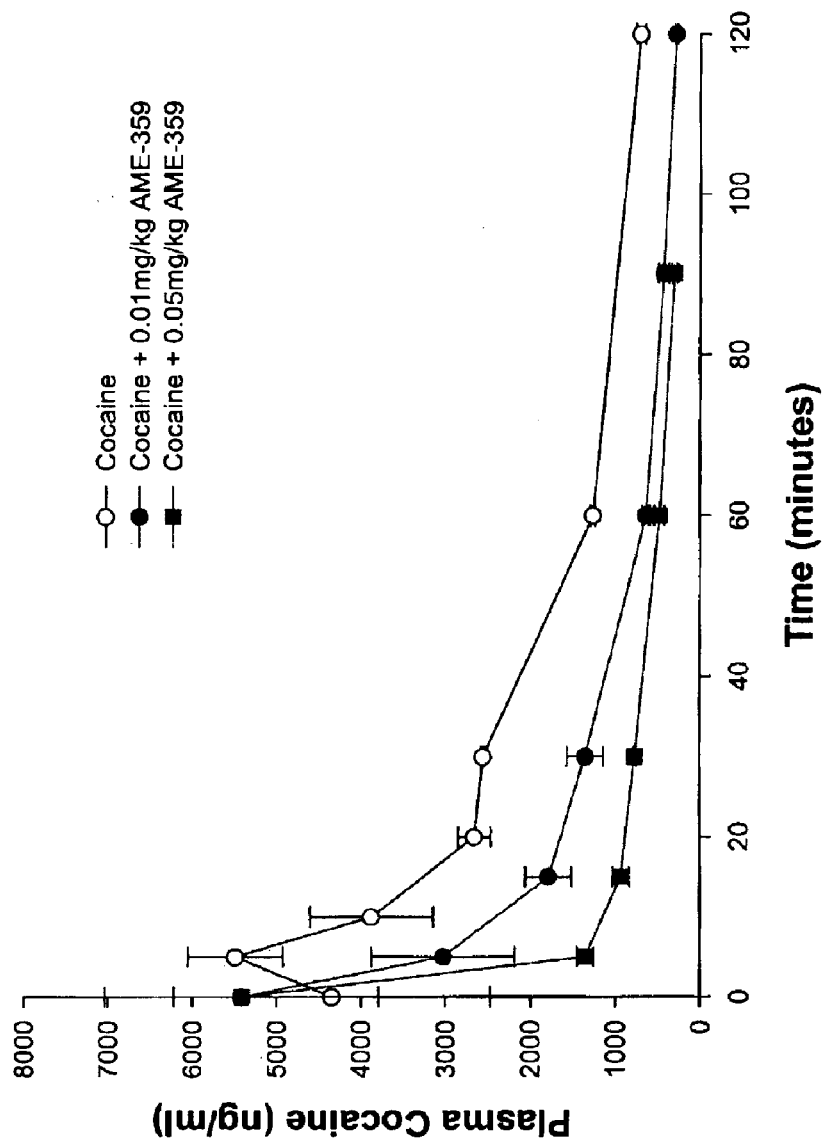
FIG. 11 shows plasma levels of an intravenous bolus of cocaine after treatment with AME-359. Cocaine was administered at 10 mg/kg (open circles) and AME-359 administered immediately at 0.01 mg/kg and 0.05 mg/kg (solid circles and solid squares, respectively).

FIG. 11 shows plasma levels of an intravenous bolus of Cocaine after treatment with the A328W/Y332M/S287G/F227A variant. Cocaine was administered at 10 mg/kg (open circles) and the A328W/Y332M/S287G/F227A variant administered immediately at 0.01 mg/kg and 0.05 mg/kg (solid circles and solid squares, respectively). Plasma samples were collected at the indicated time points and analyzed for cocaine levels by ELISA.

Figure 12:
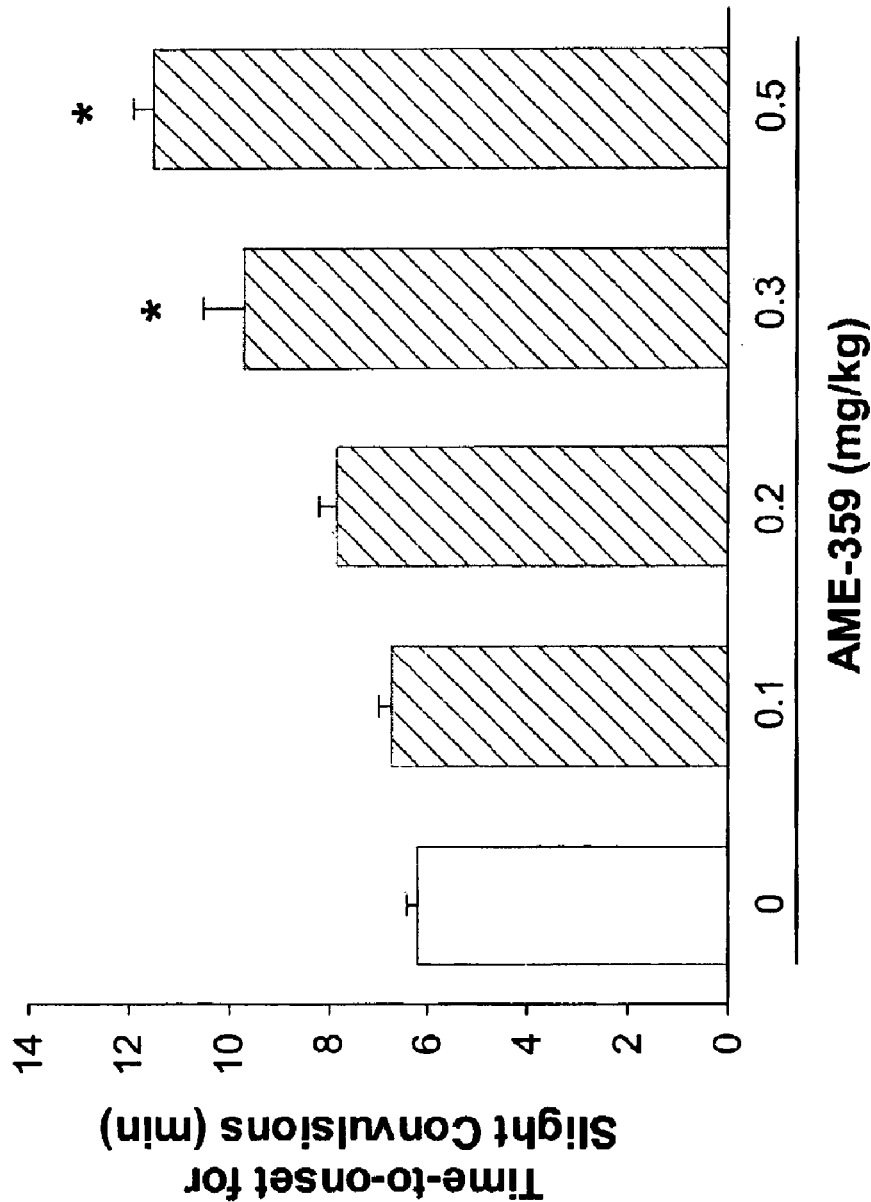
FIG. 12 shows the prophylactic effect of the butyrylcholinesterase variant designated A328W/Y332M/S287G/F227A on cocaine-induced convulsions. The variant was administered at the indicated doses, 1 minute prior to infusion of 30 mg/kg cocaine (2 mg/kg/min for 15 minutes). The data is presented as mean±sem.*p<0.001 vs. control, 0.1 mg/kg or 0.2 mg/kg variant-treated animals; ANOVA followed by Bonferroni post-test.

FIG. 12 shows the effect of pre-treatment with the A328W/Y332M/S287G/F227A variant on time-to-onset for slight convulsions. The variant was administered at the indicated doses, 1 minute prior to infusion of 30 mg/kg cocaine (2 mg/kg/min for 15 minutes). The data in FIG. 12 is presented as mean±sem.*$p<0.001$ vs. control, 0.1 mg/kg or 0.2 mg/kg variant-treated animals; ANOVA followed by Bonferroni post-test.

This example demonstrates the therapeutic effect of the A328W/Y332M/S287G/F227A variant (SEQ ID NO: 52) on cocaine-toxicity for pre-treatment as well as for treatment subsequent to cocaine exposure.

Throughout this application various publications have been referenced. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

We claim:

1. A butyrylcholinesterase variant polypeptide comprising an amino acid sequence set forth as SEQ ID NO: 52.

2. A nucleic acid encoding a butyrylcholinesterase variant polypeptide comprising an amino acid sequence set forth as SEQ ID NO: 52.

3. A nucleic acid encoding a butyrylcholinesterase variant polypeptide comprising a nucleic acid sequence set forth as SEQ ID NO: 51.

4. A method of treating a cocaine-induced condition comprising administering to an individual an effective amount of the butyrylcholinesterase variant polypeptide of claim 1.

5. The method of claim 4, wherein said cocaine-based substance is cocaine.

6. The method of claim 5, wherein said individual is symptomatic of a cocaine-overdose.

7. The method of claim 5, wherein said individual is symptomatic of cocaine addiction.

8. A method of hydrolyzing a cocaine-based butyrylcholinesterase substrate comprising contacting said butyrylcholinesterase substrate with the butyrylcholinesterase variant polypeptide of claim 1, under conditions that allow hydrolysis of cocaine into metabolites, wherein said butyrylcholinesterase variant polypeptide exhibits a one-hundred-fold or more increase in cocaine hydrolysis activity compared to butyrylcholinesterase.

9. A method of treating a cocaine-induced condition comprising administering to an individual an effective amount of a butyrylcholinesterase variant polypeptide of claim 1, wherein said butyrylcholinesterase variant polypeptide exhibits a one-hundred-fold or more increase in cocaine hydrolysis activity compared to butyryleholinesterase.

10. The method of claim 9, wherein said cocaine-based substance is cocaine.

11. The method of claim 10, wherein said individual is symptomatic of a cocaine-overdose.

12. The method of claim 10, wherein said individual is symptomatic of cocaine addiction.

* * * * *

SEQUENCE LISTING

<160> NUMBER OF SEQ ID NOS: 53

<210> SEQ ID NO 1
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 1

| | | | | | |
|---|---|---|---|---|---|
| tactgaatgt | cagtgcagtc | caatttacag | gctggagcag | cagctgcatc | ctgcatttcc | 60 |
| ccgaagtatt | acatgatttt | cactccttgc | aaactttacc | atctttgttg | cagagaatcg | 120 |
| gaaatcaata | tgcatagcaa | agtcacaatc | atatgcatca | gatttctctt | ttggtttctt | 180 |
| ttgctctgca | tgcttattgg | gaagtcacat | actgaagatg | acatcataat | tgcaacaaag | 240 |
| aatggaaaag | tcagagggat | gaacttgaca | gtttttggtg | gcacggtaac | agcctttctt | 300 |
| ggaattccct | atgcacagcc | acctcttggt | agacttcgat | tcaaaaagcc | acagtctctg | 360 |
| accaagtggt | ctgatatttg | gaatgccaca | aaatatgcaa | attcttgctg | tcagaacata | 420 |

-continued

```
gatcaaagtt ttccaggctt ccatggatca gagatgtgga acccaaacac tgacctcagt      480
gaagactgtt tatatctaaa tgtatggatt ccagcaccta aaccaaaaaa tgccactgta      540
ttgatatgga tttatggtgg tggttttcaa actggaacat catctttaca tgtttatgat      600
ggcaagtttc tggctcgggt tgaaagagtt attgtagtgt caatgaacta tagggtgggt      660
gccctaggat tcttagcttt gccaggaaat cctgaggctc cagggaacat gggtttattt      720
gatcaacagt tggctcttca gtgggttcaa aaaaatatag cagcctttgg tggaaatcct      780
aaaagtgtaa ctctctttgg agaaagtgca ggagcagctt cagttagcct gcatttgctt      840
tctcctggaa gccattcatt gttcaccaga gccattctgc aaagtggatc ctttaatgct      900
ccttgggcgg taacatctct ttatgaagct aggaacagaa cgttgaactt agctaaattg      960
actggttgct ctagagagaa tgagactgaa ataatcaagt gtcttagaaa taaagatccc     1020
caagaaattc ttctgaatga agcatttgtt gtcccctatg ggactccttt gtcagtaaac     1080
tttggtccga ccgtggatgg tgattttctc actgacatgc agacatatt acttgaactt     1140 ggacaattta aaaaacccca gattttggtg gtgttaata aagatgaagg gacatggttt     1200
ttagtcatgg gtgctcctgg cttcagcaaa gataacaata gtatcataac tagaaaagaa     1260
tttcaggaag gtttaaaaat atttttttcca ggagtgagtg agtttggaaa ggaatccatc     1320 cttttcatt acacagactg ggtagatgat cagagacctg aaaactaccg tgaggccttg     1380
ggtgatgttg ttgggggatta taatttcata tgccctgcct tggagttcac caagaagttc     1440
tcagaatggg gaaataatgc cttttctac tattttgaac accgatcctc caaacttccg     1500
tggccagaat ggatgggagt gatgcatggc tatgaaattg aatttgtctt tggtttacct     1560
ctggaaagaa gagataatta cacaaaagcc gaggaaattt tgagtagatc catagtgaaa     1620
cggtgggcaa attttgcaaa atatgggaat ccaaatgaga ctcagaacaa tagcacaagc     1680
tggcctgtct tcaaaagcac tgaacaaaaa tatctaacct tgaatacaga gtcaacaaga     1740
ataatgacga aactacgtgc tcaacaatgt cgattctgga catcattttt tccaaaagtc     1800
ttggaaatga caggaaatat tgatgaagca gaatgggagt ggaaagcagg attccatcgc     1860
tggaacaatt acatgatgga ctggaaaaat caatttaacg attacactag caagaaagaa     1920
agttgtgtgg gtctctaatt aatagattta ccctttatag aacatatttt cctttagatc     1980
aaggcaaaaa tatcaggagc ttttttacac acctactaaa aaagttatta tgtagctgaa     2040
acaaaaatgc cagaaggata atattgattc ctcacatctt taacttagta ttttacctag     2100
catttcaaaa cccaaatggc tagaacatgt ttaattaaat ttcacaatat aaagttctac     2160
agttaattat gtgcatatta aaacaatggc ctggttcaat ttctttcttt ccttaataaa     2220
tttaagtttt ttcccccccaa aattatcagt gctctgcttt tagtcacgtg tattttcatt     2280
accactcgta aaaggtatc tttttttaaat gaattaaata ttgaaacact gtacaccata     2340
gtttacaata ttatgtttcc taattaaaat aagaattgaa tgtcaatatg agatattaaa     2400
ataagcacag aaaatc                                                     2416
```

<210> SEQ ID NO 2
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (328)..(328)

```
<223> OTHER INFORMATION: A328W
<220> FEATURE:
<221> NAME/KEY: MISC_FEATURE
<222> LOCATION: (332)..(332)
<223> OTHER INFORMATION: Y332M

<400> SEQUENCE: 2

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
            85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
            115                 120                 125

Asp Gly Lys Phe Leu Ala Arg Val Glu Arg Val Ile Val Val Ser Met
        130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
            165                 170                 175

Trp Val Gln Lys Asn Ile Ala Ala Phe Gly Gly Asn Pro Lys Ser Val
        180                 185                 190

Thr Leu Phe Gly Glu Ser Ala Gly Ala Ala Ser Val Ser Leu His Leu
    195                 200                 205

Leu Ser Pro Gly Ser His Ser Leu Phe Thr Arg Ala Ile Leu Gln Ser
210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
            245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Met Gly Ala Pro Gly
            325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380
```

-continued

```
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430
Trp Met Gly Val Met His Gly Tyr Glu Ile Glu Phe Val Phe Gly Leu
        435                 440                 445
Pro Leu Glu Arg Arg Asp Asn Tyr Thr Lys Ala Glu Glu Ile Leu Ser
    450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
            500                 505                 510
Lys Leu Arg Ala Gln Gln Cys Arg Phe Trp Thr Ser Phe Phe Pro Lys
        515                 520                 525
Val Leu Glu Met Thr Gly Asn Ile Asp Glu Ala Glu Trp Glu Trp Lys
    530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570

<210> SEQ ID NO 3
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 3
tactgaatgt cagtgcagtc caatttacag gctggagcag cagctgcatc ctgcatttcc     60
ccgaagtatt acatgatttt cactccttgc aaactttacc atctttgttg cagagaatcg    120
gaaatcaata tgcatagcaa agtcacaatc atatgcatca gatttctctt ttggtttctt    180
ttgctctgca tgcttattgg gaagtcacat actgaagatg acatcataat tgcaacaaag    240
aatggaaaag tcagagggat gaacttgaca gtttttggtg gcacggtaac agcctttctt    300
ggaattccct atgcacagcc acctcttggt agacttcgat tcaaaaagcc acagtctctg    360
accaagtggt ctgatatttg gaatgccaca aaatatgcaa attcttgctg tcagaacata    420
gatcaaagtt ttccaggctt ccatggatca gagatgtgga acccaaacac tgacctcagt    480
gaagactgtt tatatctaaa tgtatggatt ccagcaccta aaccaaaaaa tgccactgta    540
ttgatatgga tttatggtgg tggttttcaa actggaacat catctttaca tgtttatgat    600
ggcaagtttc tggctcgggt tgaaagagtt attgtagtgt caatgaacta tagggtgggt    660
gccctaggat tcttagcttt gccaggaaat cctgaggctc cagggaacat gggtttattt    720
gatcaacagt tggctcttca gtgggttcaa aaaaatatag cagcctttgg tggaaatcct    780
aaaagtgtaa ctctctttgg agaaagtgca ggagcagctt cagttagcct gcatttgctt    840
tctcctggaa gccattcatt gttcaccaga gccattctgc aaagtggatc ctttaatgct    900
ccttgggcgg taacatctct ttatgaagct aggaacagaa cgttgaactt agctaaattg    960
```

-continued

```
actggttgct ctagagagaa tgagactgaa ataatcaagt gtcttagaaa taaagatccc      1020
caagaaattc ttctgaatga agcatttgtt gtcccctatg ggactccttt gtcagtaaac      1080
tttggtccga ccgtggatgg tgattttctc actgacatgc cagacatatt acttgaactt      1140
ggacaattta aaaaaaccca gattttggtg ggtgttaata aagatgaagg gacatggttt      1200
ttagtcccag gtgctcctgg cttcagcaaa gataacaata gtatcataac tagaaaagaa      1260
tttcaggaag gtttaaaaat atttttttcca ggagtgagtg agtttggaaa ggaatccatc      1320 cttttcatt acacagactg ggtagatgat cagagacctg aaaactaccg tgaggccttg      1380
ggtgatgttg ttggggatta aatttcata tgccctgcct tggagttcac caagaagttc      1440
tcagaatggg gaaataatgc cttttctac tattttgaac accgatcctc caaacttccg      1500
tggccagaat ggatgggagt gatgcatggc tatgaaattg aatttgtctt tggtttacct      1560
ctggaaagaa gagataatta cacaaaagcc gaggaaattt tgagtagatc catagtgaaa      1620
cggtgggcaa attttgcaaa atatgggaat ccaaatgaga ctcagaacaa tagcacaagc      1680
tggcctgtct tcaaaagcac tgaacaaaaa tatctaacct gaatacaga gtcaacaaga      1740 ataatgacga aactacgtgc tcaacaatgt cgattctgga catcattttt tccaaaagtc      1800
ttggaaatga caggaaatat tgatgaagca gaatgggagt ggaaagcagg attccatcgc      1860
tggaacaatt acatgatgga ctggaaaaat caatttaacg attacactag caagaaagaa      1920
agttgtgtgg gtctctaatt aatagattta ccctttatag aacatatttt cctttagatc      1980
aaggcaaaaa tatcaggagc ttttttacac acctactaaa aaagttatta tgtagctgaa      2040
acaaaaatgc cagaaggata atattgattc ctcacatctt taacttagta ttttacctag      2100
catttcaaaa cccaaatggc tagaacatgt ttaattaaat ttcacaatat aaagttctac      2160
agttaattat gtgcatatta aaacaatggc ctggttcaat ttctttcttt ccttaataaa      2220
tttaagtttt ttccccccaa aattatcagt gctctgcttt tagtcacgtg tattttcatt      2280
accactcgta aaaggtatc ttttttaaat gaattaaata ttgaaacact gtacaccata      2340
gtttacaata ttatgtttcc taattaaaat aagaattgaa tgtcaatatg agatattaaa      2400
ataagcacag aaaatc                                                     2416
```

<210> SEQ ID NO 4
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (328)..(328)
<223> OTHER INFORMATION: A328W
<220> FEATURE:
<221> NAME/KEY: MISC_FEATURE
<222> LOCATION: (332)..(332)
<223> OTHER INFORMATION: Y332P

<400> SEQUENCE: 4

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60
```

-continued

```
Cys Cys Gln Asn Ile Asp Gln Ser Phe Pro Gly Phe His Gly Ser Glu
 65              70                  75                  80

Met Trp Asn Pro Asn Thr Asp Leu Ser Glu Asp Cys Leu Tyr Leu Asn
                 85                  90                  95

Val Trp Ile Pro Ala Pro Lys Pro Lys Asn Ala Thr Val Leu Ile Trp
                100                 105                 110

Ile Tyr Gly Gly Gly Phe Gln Thr Gly Thr Ser Ser Leu His Val Tyr
            115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
                180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Pro Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480
```

| | | | | | | | | | | | | |
|---|---|---|---|---|---|---|---|---|---|---|---|---|
|Asn|Glu|Thr|Gln|Asn|Asn|Ser|Thr|Ser|Trp|Pro|Val|Phe|Lys|Ser|Thr|
| | | | |485| | | | |490| | | | |495| |

| | | | | | | | | | | | |
|---|---|---|---|---|---|---|---|---|---|---|---|
|Glu|Gln|Lys|Tyr|Leu|Thr|Leu|Asn|Thr|Glu|Ser|Thr|Arg|Ile|Met|Thr|
| | | | |500| | | | |505| | | | |510| |

Lys Leu Arg Ala Gln Gln Cys Arg Phe Trp Thr Ser Phe Phe Pro Lys
            515                    520                    525

Val Leu Glu Met Thr Gly Asn Ile Asp Glu Ala Glu Trp Glu Trp Lys
     530                  535                  540

Ala Gly Phe His Arg Trp Asn Asn Tyr Met Met Asp Trp Lys Asn Gln
545                  550                  555              560

Phe Asn Asp Tyr Thr Ser Lys Lys Glu Ser Cys Val Gly Leu
            565                    570

<210> SEQ ID NO 5
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 5

```
tactgaatgt cagtgcagtc caatttacag gctggagcag cagctgcatc ctgcat

-continued

```
ctggaaagaa gagataatta cacaaaagcc gaggaaattt tgagtagatc catagtgaaa    1620
cggtgggcaa attttgcaaa atatgggaat ccaaatgaga ctcagaacaa tagcacaagc    1680
tggcctgtct tcaaaagcac tgaacaaaaa tatctaacct tgaatacaga gtcaacaaga    1740
ataatgacga aactacgtgc tcaacaatgt cgattctgga catcattttt tccaaaagtc    1800
ttggaaatga caggaaatat tgatgaagca aatgggagt ggaaagcagg attccatcgc     1860
tggaacaatt acatgatgga ctggaaaaat caatttaacg attacactag caagaaagaa    1920
agttgtgtgg gtctctaatt aatagattta ccctttatag aacatatttt cctttagatc    1980
aaggcaaaaa tatcaggagc ttttttacac acctactaaa aaagttatta tgtagctgaa    2040
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttccccccaa aattatcagt gctctgcttt tagtcacgtg tattttcatt    2280
accactcgta aaaggtatc ttttttaaat gaattaaata ttgaaacact gtacaccata     2340
gtttacaata ttatgtttcc taattaaaat aagaattgaa tgtcaatatg agatattaaa    2400
ataagcacag aaaatc                                                   2416
```

<210> SEQ ID NO 6
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (328)..(328)
<223> OTHER INFORMATION: A328W
<220> FEATURE:
<221> NAME/KEY: MISC_FEATURE
<222> LOCATION: (331)..(331)
<223> OTHER INFORMATION: V331L

<400> SEQUENCE: 6

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160
```

-continued

```
Glu Ala Pro Gly Asn Met Gly Leu Phe Asp Gln Gln Leu Ala Leu Gln
                165                 170                 175
Trp Val Gln Lys Asn Ile Ala Ala Phe Gly Asn Pro Lys Ser Val
            180                 185                 190
Thr Leu Phe Gly Glu Ser Ala Gly Ala Ala Ser Val Ser Leu His Leu
        195                 200                 205
Leu Ser Pro Gly Ser His Ser Leu Phe Thr Arg Ala Ile Leu Gln Ser
    210                 215                 220
Gly Ser Phe Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
                260                 265                 270
Leu Leu Asn Glu Ala Phe Val Val Pro Tyr Gly Thr Pro Leu Ser Val
            275                 280                 285
Asn Phe Gly Pro Thr Val Asp Gly Asp Phe Leu Thr Asp Met Pro Asp
        290                 295                 300
Ile Leu Leu Glu Leu Gly Gln Phe Lys Lys Thr Gln Ile Leu Val Gly
305                 310                 315                 320
Val Asn Lys Asp Glu Gly Thr Trp Phe Leu Leu Tyr Gly Ala Pro Gly
                325                 330                 335
Phe Ser Lys Asp Asn Asn Ser Ile Ile Thr Arg Lys Glu Phe Gln Glu
                340                 345                 350
Gly Leu Lys Ile Phe Phe Pro Gly Val Ser Glu Phe Gly Lys Glu Ser
            355                 360                 365
Ile Leu Phe His Tyr Thr Asp Trp Val Asp Asp Gln Arg Pro Glu Asn
        370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
            420                 425                 430
Trp Met Gly Val Met His Gly Tyr Glu Ile Glu Phe Val Phe Gly Leu
        435                 440                 445
Pro Leu Glu Arg Arg Asp Asn Tyr Thr Lys Ala Glu Glu Ile Leu Ser
    450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
                500                 505                 510
Lys Leu Arg Ala Gln Gln Cys Arg Phe Trp Thr Ser Phe Phe Pro Lys
            515                 520                 525
Val Leu Glu Met Thr Gly Asn Ile Asp Glu Ala Glu Trp Glu Trp Lys
        530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570
```

-continued

<210> SEQ ID NO 7
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 7

```
tactgaatgt cagtgcagtc caatttacag gctggagcag cagctgcatc ctgcatttcc     60
ccgaagtatt acatgatttt cactccttgc aaactttacc atctttgttg cagagaatcg    120
gaaatcaata tgcatagcaa agtcacaatc atatgcatca gatttctctt ttggtttctt    180
ttgctctgca tgcttattgg gaagtcacat actgaagatg acatcataat tgcaacaaag    240
aatggaaaag tcagagggat gaacttgaca gtttttggtg gcacggtaac agcctttctt    300
ggaattccct atgcacagcc acctcttggt agacttcgat tcaaaaagcc acagtctctg    360
accaagtggt ctgatatttg gaatgccaca aaatatgcaa attcttgctg tcagaacata    420
gatcaaagtt ttccaggctt ccatggatca gagatgtgga acccaaacac tgacctcagt    480
gaagactgtt tatatctaaa tgtatggatt ccagcaccta aaccaaaaaa tgccactgta    540
ttgatatgga tttatggtgg tggttttcaa actggaacat catctttaca tgtttatgat    600
ggcaagtttc tggctcgggt tgaaagagtt attgtagtgt caatgaacta tagggtgggt    660
gccctaggat tcttagcttt gccaggaaat cctgaggctc cagggaacat gggtttattt    720
gatcaacagt tggctcttca gtgggttcaa aaaaatatag cagcctttgg tggaaatcct    780
aaaagtgtaa ctctctttgg agaaagtgca ggagcagctt cagttagcct gcatttgctt    840
tctcctggaa gccattcatt gttcaccaga gccattctgc aaagtggatc ctttaatgct    900
ccttgggcgg taacatctct ttatgaagct aggaacagaa cgttgaactt agctaaattg    960
actggttgct ctagagagaa tgagactgaa ataatcaagt gtcttagaaa taaagatccc   1020
caagaaattc ttctgaatga agcatttgtt gtcccctatg ggactccttt gtcagtaaac   1080
tttggtccga ccgtggatgg tgattttctc actgacatgc cagacatatt acttgaactt   1140
ggacaattta aaaaaaccca gattttggtg ggtgttaata aagatgaagg gacatggttt   1200
ttagtctcgg gtgctcctgg cttcagcaaa gataacaata gtatcataac tagaaaagaa   1260
tttcaggaag gtttaaaaat attttttcca ggagtgagtg agtttggaaa ggaatccatc   1320
ctttttcatt acacagactg ggtagatgat cagagacctg aaaactaccg tgaggccttg   1380
ggtgatgttg ttggggatta taatttcata tgccctgcct tggagttcac caagaagttc   1440
tcagaatggg gaaataatgc ctttttctac tattttgaac accgatcctc caaacttccg   1500
tggccagaat ggatgggagt gatgcatggc tatgaaattg aatttgtctt tggtttacct   1560
ctggaaagaa gagataatta cacaaaagcc gaggaaattt tgagtagatc catagtgaaa   1620
cggtgggcaa attttgcaaa atatgggaat ccaaatgaga ctcagaacaa tagcacaagc   1680
tggcctgtct tcaaaagcac tgaacaaaaa tatctaacct tgaatacaga gtcaacaaga   1740
ataatgacga aactacgtgc tcaacaatgt cgattctgga catcattttt tccaaaagtc   1800
ttggaaatga caggaaatat tgatgaagca gaatgggagt ggaaagcagg attccatcgc   1860
tggaacaatt acatgatgga ctggaaaaat caatttaacg attacactag caagaaagaa   1920
agttgtgtgg gtctctaatt aatagattta ccctttatag aacatatttt cctttagatc   1980
aaggcaaaaa tatcaggagc ttttttacac acctactaaa aaagttatta tgtagctgaa   2040
acaaaaatgc cagaaggata atattgattc ctcacatctt taacttagta ttttacctag   2100
```

-continued

```
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttccccccaa aattatcagt gctctgcttt tagtcacgtg tattttcatt    2280
accactcgta aaaggtatc ttttttaaat gaattaaata ttgaaacact gtacaccata     2340
gtttacaata ttatgtttcc taattaaaat aagaattgaa tgtcaatatg agatattaaa    2400
ataagcacag aaaatc                                                    2416
```

```
<210> SEQ ID NO 8
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (328)..(328)
<223> OTHER INFORMATION: A328W
<220> FEATURE:
<221> NAME/KEY: MISC_FEATURE
<222> LOCATION: (332)..(332)
<223> OTHER INFORMATION: Y332S

<400> SEQUENCE: 8
```

| Glu | Asp | Asp | Ile | Ile | Ile | Ala | Thr | Lys | Asn | Gly | Lys | Val | Arg | Gly | Met |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asn | Leu | Thr | Val | Phe | Gly | Gly | Thr | Val | Thr | Ala

-continued

```
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Ser Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 9
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 9
tactgaatgt cagtgcagtc caatttacag gctggagcag cagctgcatc ctgcatttcc     60
ccgaagtatt acatgatttt cactccttgc aaactttacc atctttgttg cagagaatcg    120
gaaatcaata tgcatagcaa agtcacaatc atatgcatca gatttctctt ttggtttctt    180
ttgctctgca tgcttattgg gaagtcacat actgaagatg acatcataat tgcaacaaag    240
aatggaaaag tcagagggat gaacttgaca gtttttggtg gcacggtaac agcctttctt    300
```

-continued

```
ggaattccct atgcacagcc acctcttggt agacttcgat tcaaaaagcc acagtctctg    360
accaagtggt ctgatatttg aatgccaca aatatgcaa attcttgctg tcagaacata    420
gatcaaagtt ttccaggctt ccatggatca gagatgtgga acccaaacac tgacctcagt    480
gaagactgtt tatatctaaa tgtatggatt ccagcaccta aaccaaaaaa tgccactgta    540
ttgatatgga tttatggtgg tggttttcaa actggaacat catctttaca tgtttatgat    600
ggcaagtttc tggctcgggt tgaaagagtt attgtagtgt caatgaacta tagggtgggt    660
gccctaggat tcttagcttt gccaggaaat cctgaggctc cagggaacat gggtttattt    720
gatcaacagt tggctcttca gtgggttcaa aaaatatag cagcctttgg tggaaatcct    780
aaaagtgtaa ctctctttgg agaaagttca ggagcagctt cagttagcct gcatttgctt    840
tctcctggaa gccattcatt gttcaccaga gccattctgc aaagtggatc cgcgaatgct    900
ccttgggcgg taacatctct ttatgaagct aggaacagaa cgttgaactt agctaaattg    960
actggttgct ctagagagaa tgagactgaa ataatcaagt gtcttagaaa taaagatccc   1020
caagaaattc ttctgaatga agcatttgtt gtccccctatg ggactccttt gggtgtaaac   1080
tttggtccga ccgtggatgg tgattttctc actgacatgc agacatatt acttgaactt   1140 ggacaattta aaaaaaccca gattttggtg ggtgttaata agatgaagg acatggtttt   1200 ttagtcatgg gtgctcctgg cttcagcaaa gataacaata gtatcataac tagaaaagaa   1260
tttcaggaag gttttaaaaat attttttcca ggagtgagtg agtttggaaa ggaatccatc   1320 cttttttcatt acacagactg ggtagatgat cagagacctg aaaactaccg tgaggccttg   1380
ggtgatgttg ttggggatta taatttcata tgccctgcct tggagttcac caagaagttc   1440
tcagaatggg gaaataatgc cttttttctac tattttgaac accgatcctc caaacttccg   1500
tggccagaat ggatgggagt gatgcatggc tatgaaattg aatttgtctt tggtttacct   1560
ctggaaagaa gagataatta cacaaaagcc gaggaaattt tgagtagatc catagtgaaa   1620
cggtgggcaa attttgcaaa atatgggaat ccaaatgaga ctcagaacaa tagcacaagc   1680
tggcctgtct tcaaaagcac tgaacaaaaa tatctaacct tgaatacaga gtcaacaaga   1740
ataatgacga aactacgtgc tcaacaatgt cgattctgga catcatttt tccaaaagtc   1800 ttggaaatga caggaaatat tgatgaagca gaatgggagt ggaaagcagg attccatcgc   1860
tggaacaatt acatgatgga ctggaaaaat caatttaacg attacactag caagaaagaa   1920
agttgtgtgg gtctctaatt aatagattta ccctttatag aacatatttt cctttagatc   1980
aaggcaaaaa tatcaggagc ttttttacac acctactaaa aaagttatta tgtagctgaa   2040
acaaaaatgc cagaaggata atattgattc ctcacatctt taacttagta tttttacctag   2100 catttcaaaa cccaaatggc tagaacatgt ttaattaaat ttcacaatat aaagttctac   2160
agttaattat gtgcatatta aaacaatggc ctggttcaat ttctttcttt ccttaataaa   2220
tttaagtttt ttccccccaa aattatcagt gctctgcttt tagtcacgtg tattttcatt   2280
accactcgta aaaggtatc ttttttaaat gaattaaata ttgaaacact gtacaccata   2340
gtttacaata ttatgtttcc taattaaaat aagaattgaa tgtcaatatg agatattaaa   2400
ataagcacag aaaatc                                                   2416
```

<210> SEQ ID NO 10
<211> LENGTH: 574
<212> TYPE: PRT
<213> ORGANISM: Artificial
<220> FEATURE:
<223> OTHER INFORMATION: Butyrylcholinesterase variant -continued

```
<220> FEATURE:
<221> NAME/KEY: MISC_FEATURE
<222> LOCATION: (199)..(199)
<223> OTHER INFORMATION: A199S
<220> FEATURE:
<221> NAME/KEY: MISC_FEATURE
<222> LOCATION: (227)..(227)
<223> OTHER INFORMATION: F227A
<220> FEATURE:
<221> NAME/KEY: MISC_FEATURE
<222> LOCATION: (287)..(287)
<223> OTHER INFORMATION: S287G
<220> FEATURE:
<221> NAME/KEY: MISC_FEATURE
<222> LOCATION: (328)..(328)
<223> OTHER INFORMATION: A328W
<220> FEATURE:
<221> NAME/KEY: MISC_FEATURE
<222> LOCATION: (332)..(332)
<223> OTHER INFORMATION: Y332M

<400> SEQUENCE: 10

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Gly Val
        275                 280                 285

Asn Phe Gly Pro Thr Val Asp Gly Asp Phe Leu Thr Asp Met Pro Asp
    290                 295                 300
```

-continued

```
Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Met Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 11
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 11

```
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat actgaagatg acatcataat tgcaacaaag     240
aatggaaaag tcagagggat gaacttgaca gtttttggtg gcacggtaac agcctttctt     300
ggaattccct atgcacagcc acctcttggt agacttcgat tcaaaaagcc acagtctctg     360
accaagtggt ctgatatttg gaatgccaca aaatatgcaa attcttgctg tcagaacata     420
gatcaaagtt ttccaggctt ccatggatca gagatgtgga acccaaacac tgacctcagt     480
gaagactgtt tatatctaaa tgtatggatt ccagcaccta aaccaaaaaa tgccactgta     540
```

-continued

```
ttgatatgga tttatggtgg tggttttcaa actggaacat catctttaca tgtttatgat     600
ggcaagtttc tggctcgggt tgaaagagtt attgtagtgt caatgaacta tagggtgggt     660
gccctaggat tcttagcttt gccaggaaat cctgaggctc cagggaacat gggtttattt     720
gatcaacagt tggctcttca gtgggttcaa aaaaatatag cagcctttgg tggaaatcct     780
aaaagtgtaa ctctctttgg agaaagttca ggagcagctt cagttagcct gcatttgctt     840
tctcctggaa gccattcatt gttcaccaga gccattctgc aaagtggatc cgcgaatgct     900
ccttgggcgg taacatctct ttatgaagct aggaacagaa cgttgaactt agctaaattg     960
actggttgct ctagagagaa tgagactgaa ataatcaagt gtcttagaaa taaagatccc    1020
caagaaattc ttctgaatga agcatttgtt gtcccctatg ggactccttt gggtgtaaac    1080
tttggtccga ccgtggatgg tgattttctc actgacatgc agacatatt acttgaactt    1140
ggacaattta aaaaaaccca gattttggtg gtgttaata aagatgaagg acatggtttt    1200
ttagtctatg gtgctcctgg cttcagcaaa gataacaata gtatcataac tagaaaagaa    1260
tttcaggaag gtttaaaaat attttttcca ggagtgagtg agtttggaaa ggaatccatc    1320
cttttttcatt acacagactg ggtagatgat cagagacctg aaaactaccg tgaggccttg    1380
ggtgatgttg ttgggggatta taatttcata tgccctgcct tggagttcac caagaagttc    1440
tcagaatggg gaaataatgc ctttttctac tattttgaac accgatcctc caaacttccg    1500
tggccagaat ggatgggagt gatgcatggc tatgaaattg aatttgtctt tggtttacct    1560
ctggaaagaa gagataatta cacaaaagcc gaggaaattt tgagtagatc catagtgaaa    1620
cggtgggcaa attttgcaaa atatgggaat ccaaatgaga ctcagaacaa tagcacaagc    1680
tggcctgtct tcaaaagcac tgaacaaaaa tatctaaccct tgaatacaga gtcaacaaga    1740
ataatgacga aactacgtgc tcaacaatgt cgattctgga catcattttt tccaaaagtc    1800
ttggaaatga caggaaatat tgatgaagca gaatgggagt ggaaagcagg attccatcgc    1860
tggaacaatt acatgatgga ctggaaaaat caatttaacg attacactag caagaaagaa    1920
agttgtgtgg gtctctaatt aatagattta ccctttatag aacatatttt cctttagatc    1980
aaggcaaaaa tatcaggagc tttttttacac acctactaaa aaagttatta tgtagctgaa    2040
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttccccccaa aattatcagt gctctgcttt tagtcacgtg tattttcatt    2280
accactcgta aaaaggtatc ttttttaaat gaattaaata ttgaaacact gtacaccata    2340
gtttacaata ttatgtttcc taattaaaat aagaattgaa tgtcaatatg agatattaaa    2400
ataagcacag aaaatc                                                    2416
```

<210> SEQ ID NO 12
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (199)..(199)
<223> OTHER INFORMATION: A199S
<220> FEATURE:
<221> NAME/KEY: MISC_FEATURE
<222> LOCATION: (227)..(227)

```
<223> OTHER INFORMATION: F227A
<220> FEATURE:
<221> NAME/KEY: MISC_FEATURE
<222> LOCATION: (287)..(287)
<223> OTHER INFORMATION: S287G
<220> FEATURE:
<221> NAME/KEY: MISC_FEATURE
<222> LOCATION: (328)..(328)
<223> OTHER INFORMATION: A328W

<400> SEQUENCE: 12
```

| | | | | | | | | | | | | | | |
|---|---|---|---|---|---|---|---|---|---|---|---|---|---|---|
| Glu | Asp | Asp | Ile | Ile | Ile | Ala | Thr | Lys | Asn | Gly | Lys | Val | Arg | Gly | Met |
| 1 | | | | 5 | | | | | 10 | | | | | 15 | |
| Asn | Leu | Thr | Val | Phe | Gly | Gly | Thr | Val | Thr | Ala | Phe | Leu | Gly | Ile | Pro |
| | | | 20 | | | | | 25 | | | | | 30 | | |
| Tyr | Ala | Gln | Pro | Pro | Leu | Gly | Arg | Leu | Arg | Phe | Lys | Lys | Pro | Gln | Ser |
| | | 35 | | | | | 40 | | | | | 45 | | | |
| Leu | Thr | Lys | Trp | Ser | Asp | Ile | Trp | Asn | Ala | Thr | Lys | Tyr | Ala | Asn | Ser |
| | 50 | | | | | 55 | | | | | 60 | | | | |
| Cys | Cys | Gln | Asn | Ile | Asp | Gln | Ser | Phe | Pro | Gly | Phe | His | Gly | Ser | Glu |
| 65 | | | | | 70 | | | | | 75 | | | | | 80 |
| Met | Trp | Asn | Pro | Asn | Thr | Asp | Leu | Ser | Glu | Asp | Cys | Leu | Tyr | Leu | Asn |
| | | | | 85 | | | | | 90 | | | | | 95 | |
| Val | Trp | Ile | Pro | Ala | Pro | Lys | Pro | Lys | Asn | Ala | Thr | Val | Leu | Ile | Trp |
| | | | 100 | | | | | 105 | | | | | 110 | | |
| Ile | Tyr | Gly | Gly | Gly | Phe | Gln | Thr | Gly | Thr | Ser | Ser | Leu | His | Val | Tyr |
| | | 115 | | | | | 120 | | | | | 125 | | | |
| Asp | Gly | Lys | Phe | Leu | Ala | Arg | Val | Glu | Arg | Val | Ile | Val | Val | Ser | Met |
| | 130 | | | | | 135 | | | | | 140 | | | | |
| Asn | Tyr | Arg | Val | Gly | Ala | Leu | Gly | Phe | Leu | Ala | Leu | Pro | Gly | Asn | Pro |
| 145 | | | | | 150 | | | | | 155 | | | | | 160 |
| Glu | Ala | Pro | Gly | Asn | Met | Gly | Leu | Phe | Asp | Gln | Gln | Leu | Ala | Leu | Gln |
| | | | | 165 | | | | | 170 | | | | | 175 | |
| Trp | Val | Gln | Lys | Asn | Ile | Ala | Ala | Phe | Gly | Gly | Asn | Pro | Lys | Ser | Val |
| | | | 180 | | | | | 185 | | | | | 190 | | |
| Thr | Leu | Phe | Gly | Glu | Ser | Ser | Gly | Ala | Ala | Ser | Val | Ser | Leu | His | Leu |
| | | 195 | | | | | 200 | | | | | 205 | | | |
| Leu | Ser | Pro | Gly | Ser | His | Ser | Leu | Phe | Thr | Arg | Ala | Ile | Leu | Gln | Ser |
| | 210 | | | | | 215 | | | | | 220 | | | | |
| Gly | Ser | Ala | Asn | Ala | Pro | Trp | Ala | Val | Thr | Ser | Leu | Tyr | Glu | Ala | Arg |
| 225 | | | | | 230 | | | | | 235 | | | | | 240 |
| Asn | Arg | Thr | Leu | Asn | Leu | Ala | Lys | Leu | Thr | Gly | Cys | Ser | Arg | Glu | Asn |
| | | | | 245 | | | | | 250 | | | | | 255 | |
| Glu | Thr | Glu | Ile | Ile | Lys | Cys | Leu | Arg | Asn | Lys | Asp | Pro | Gln | Glu | Ile |
| | | | 260 | | | | | 265 | | | | | 270 | | |
| Leu | Leu | Asn | Glu | Ala | Phe | Val | Val | Pro | Tyr | Gly | Thr | Pro | Leu | Gly | Val |
| | | 275 | | | | | 280 | | | | | 285 | | | |
| Asn | Phe | Gly | Pro | Thr | Val | Asp | Gly | Asp | Phe | Leu | Thr | Asp | Met | Pro | Asp |
| | 290 | | | | | 295 | | | | | 300 | | | | |
| Ile | Leu | Leu | Glu | Leu | Gly | Gln | Phe | Lys | Lys | Thr | Gln | Ile | Leu | Val | Gly |
| 305 | | | | | 310 | | | | | 315 | | | | | 320 |
| Val | Asn | Lys | Asp | Glu | Gly | Thr | Trp | Phe | Leu | Val | Tyr | Gly | Ala | Pro | Gly |
| | | | | 325 | | | | | 330 | | | | | 335 | |
| Phe | Ser | Lys | Asp | Asn | Asn | Ser | Ile | Ile | Thr | Arg | Lys | Glu | Phe | Gln | Glu |
| | | | 340 | | | | | 345 | | | | | 350 | | |
| Gly | Leu | Lys | Ile | Phe | Phe | Pro | Gly | Val | Ser | Glu | Phe | Gly | Lys | Glu | Ser |

-continued

```
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 13
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 13

```
tactgaatgt cagtgcagtc caatttacag gctggagcag cagctgcatc ctgcatttcc     60
ccgaagtatt acatgatttt cactccttgc aaactttacc atctttgttg cagagaatcg    120
gaaatcaata tgcatagcaa agtcacaatc atatgcatca gatttctctt ttggtttctt    180
ttgctctgca tgcttattgg gaagtcacat actgaagatg acatcataat tgcaacaaag    240
aatggaaaag tcagagggat gaacttgaca gtttttggtg gcacggtaac agcctttctt    300
ggaattccct atgcacagcc acctcttggt agacttcgat tcaaaaagcc acagtctctg    360
accaagtggt ctgatatttg gaatgccaca aaatatgcaa attcttgctg tcagaacata    420
gatcaaagtt ttccaggctt ccatggatca gagatgtgga acccaaacac tgacctcagt    480
gaagactgtt tatatctaaa tgtatggatt ccagcaccta aaccaaaaaa tgccactgta    540
ttgatatgga tttatggtgg tggttttcaa actggaacat catctttaca tgtttatgat    600
ggcaagtttc tggctcgggt tgaaagagtt attgtagtgt caatgaacta tagggtgggt    660
gccctaggat tcttagcttt gccaggaaat cctgaggctc cagggaacat gggtttattt    720
gatcaacagt tggctcttca gtgggttcaa aaaaatatag cagcctttgg tggaaatcct    780
aaaagtgtaa ctctctttgg agaaagttca ggagcagctt cagttagcct gcatttgctt    840
```

```
tctcctggaa gccattcatt gttcaccaga gccattctgc aaagtggatc ctttaatgct      900
ccttgggcgg taacatctct ttatgaagct aggaacagaa cgttgaactt agctaaattg      960
actggttgct ctagagagaa tgagactgaa ataatcaagt gtcttagaaa taaagatccc     1020
caagaaattc ttctgaatga agcatttgtt gtcccctatg ggactccttt gggtgtaaac     1080
tttggtccga ccgtggatgg tgattttctc actgacatgc agacatatt acttgaactt     1140
ggacaattta aaaaaccca gattttggtg ggtgttaata aagatgaagg gacatggttt     1200
ttagtctatg gtgctcctgg cttcagcaaa gataacaata gtatcataac tagaaaagaa     1260
tttcaggaag gtttaaaaat attttttcca ggagtgagtg agtttggaaa ggaatccatc     1320
cttttcatt acacagactg gtagatgat cagagacctg aaaactaccg tgaggccttg       1380
ggtgatgttg ttggggatta taatttcata tgccctgcct ggagttcac caagaagttc      1440
tcagaatggg gaaataatgc cttttctac tattttgaac accgatcctc caaacttccg      1500
tggccagaat ggatgggagt gatgcatggc tatgaaattg aatttgtctt ggtttacct      1560
ctggaaagaa gagataatta cacaaaagcc gaggaaattt tgagtagatc catagtgaaa     1620
cggtgggcaa atttttgcaaa atatgggaat ccaaatgaga ctcagaacaa tagcacaagc    1680
tggcctgtct tcaaaagcac tgaacaaaaa tatctaacct tgaatacaga gtcaacaaga    1740
ataatgacga aactacgtgc tcaacaatgt cgattctgga catcattttt tccaaaagtc    1800
ttggaaatga caggaaatat tgatgaagca gaatgggagt ggaaagcagg attccatcgc    1860
tggaacaatt acatgatgga ctggaaaaat caatttaacg attacactag caagaaagaa    1920
agttgtgtgg gtctctaatt aatagattta ccctttatag aacatatttt cctttagatc    1980
aaggcaaaaa tatcaggagc ttttttacac acctactaaa aaagttatta tgtagctgaa    2040
acaaaaatgc cagaaggata atattgattc ctcacatctt aacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttcccccccaa aattatcagt gctctgcttt tagtcacgtg tattttcatt    2280
accactcgta aaaggtatc tttttttaaat gaattaaata ttgaaacact gtacaccata     2340
gtttacaata ttatgtttcc taattaaaat aagaattgaa tgtcaatatg agatattaaa    2400
ataagcacag aaaatc                                                    2416
```

<210> SEQ ID NO 14
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (199)..(199)
<223> OTHER INFORMATION: A199

```
Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Gly Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
```

-continued

```
        435                 440                 445

Pro Leu Glu Arg Arg Asp Asn Tyr Thr Lys Ala Glu Glu Ile Leu Ser
    450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
            500                 505                 510
Lys Leu Arg Ala Gln Gln Cys Arg Phe Trp Thr Ser Phe Phe Pro Lys
        515                 520                 525
Val Leu Glu Met Thr Gly Asn Ile Asp Glu Ala Glu Trp Glu Trp Lys
    530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570
```

<210> SEQ ID NO 15
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 15

```
tactgaatgt cagtgcagtc caatttacag gctggagcag cagctgcatc ctgcatttcc     60
ccgaagtatt acatgatttt cactccttgc aaactttacc atctttgttg cagagaatcg    120
gaaatcaata tgcatagcaa agtcacaatc atatgcatca gatttctctt ttggtttctt    180
ttgctctgca tgcttattgg gaagtcacat actgaagatg acatcataat tgcaacaaag    240
aatggaaaag tcagagggat gaacttgaca gtttttggtg gcacggtaac agcctttctt    300
ggaattccct atgcacagcc acctcttggt agacttcgat tcaaaaagcc acagtctctg    360
accaagtggt ctgatatttg gaatgccaca aaatatgcaa attcttgctg tcagaacata    420
gatcaaagtt ttccaggctt ccatggatca gagatgtgga acccaaacac tgacctcagt    480
gaagactgtt tatatctaaa tgtatggatt ccagcaccta aaccaaaaaa tgccactgta    540
ttgatatgga tttatggtgg tggttttcaa actggaacat catctttaca tgtttatgat    600
ggcaagtttc tggctcgggt tgaaagagtt attgtagtgt caatgaacta tagggtgggt    660
gccctaggat tcttagcttt gccaggaaat cctgaggctc cagggaacat gggtttattt    720
gatcaacagt tggctcttca gtgggttcaa aaaaatatag cagcctttgg tggaaatcct    780
aaaagtgtaa ctctctttgg agaaagtgca ggagcagctt cagttagcct gcatttgctt    840
tctcctggaa gccattcatt gttcaccaga gccattctgc aaagtggatc cgcgaatgct    900
ccttgggcgg taacatctct ttatgaagct aggaacagaa cgttgaactt agctaaattg    960
actggttgct ctagagagaa tgagactgaa ataatcaagt gtcttagaaa taaagatccc   1020
caagaaattc ttctgaatga agcatttgtt gtcccctatg ggactccttt gggtgtaaac   1080
tttggtccga ccgtggatgg tgattttctc actgacatgc cagacatatt acttgaactt   1140
ggacaattta aaaaaaccca gattttggtg ggtgttaata aagatgaagg gacatggttt   1200
ttagtctatg gtgctcctgg cttcagcaaa gataacaata gtatcataac tagaaaagaa   1260
tttcaggaag gtttaaaaat attttttcca ggagtgagtg agtttggaaa ggaatccatc   1320
```

```
cttttttcatt acacagactg ggtagatgat cagagacctg aaaactaccg tgaggccttg   1380
ggtgatgttg ttgggggatta taatttcata tgccctgcct tggagttcac caagaagttc   1440
tcagaatggg gaaataatgc ctttttctac tattttgaac accgatcctc caaacttccg   1500
tggccagaat ggatgggagt gatgcatggc tatgaaattg aatttgtctt tggtttacct   1560
ctggaaagaa gagataatta cacaaaagcc gaggaaattt tgagtagatc catagtgaaa   1620
cggtgggcaa attttgcaaa atatgggaat ccaaatgaga ctcagaacaa tagcacaagc   1680
tggcctgtct tcaaaagcac tgaacaaaaa tatctaacct gaatacaga gtcaacaaga   1740 ataatgacga aactacgtgc tcaacaatgt cgattctgga catcattttt tccaaaagtc   1800
ttggaaatga caggaaatat tgatgaagca gaatgggagt ggaaagcagg attccatcgc   1860
tggaacaatt acatgatgga ctggaaaaat caatttaacg attacactag caagaaagaa   1920
agttgtgtgg gtctctaatt aatagattta ccctttatag aacatatttt cctttagatc   1980
aaggcaaaaa tatcaggagc ttttttacac acctactaaa aaagttatta tgtagctgaa   2040
acaaaaatgc cagaaggata atattgattc ctcacatctt taacttagta ttttacctag   2100
catttcaaaa cccaaatggc tagaacatgt ttaattaaat ttcacaatat aaagttctac   2160
agttaattat gtgcatatta aaacaatggc ctggttcaat ttctttcttt ccttaataaa   2220
tttaagtttt ttccccccaa aattatcagt gctctgcttt tagtcacgtg tattttcatt   2280
accactcgta aaaaggtatc ttttttaaat gaattaaata ttgaaacact gtacaccata   2340
gtttacaata ttatgttttcc taattaaaat aagaattgaa tgtcaatatg agatattaaa   2400
ataagcacag aaaatc                                                    2416
```

```
<210> SEQ ID NO 16
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (227)..(227)
<223> OTHER INFORMATION: F227A
<220> FEATURE:
<221> NAME/KEY: MISC_FEATURE
<222> LOCATION: (287)..(287)
<223> OTHER INFORMATION: S287G
<220> FEATURE:
<221> NAME/KEY: MISC_FEATURE
<222> LOCATION: (328)..(328)
<223> OTHER INFORMATION: A328W

<400> SEQUENCE: 16

Glu Asp Asp Ile Ile Ile Ala Thr Lys Asn Gly Lys Val Arg Gly Met
1               5                   10                  15

Asn Leu Thr Val

-continued

```
Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
            115                 120                 125

Asp Gly Lys Phe Leu Ala Arg Val Glu Arg Val Ile Val Val Ser Met
            130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
                180                 185                 190

Thr Leu Phe Gly Glu Ser Ala Gly Ala Ala Ser Val Ser Leu His Leu
                195                 200                 205

Leu Ser Pro Gly Ser His Ser Leu Phe Thr Arg Ala Ile Leu Gln Ser
            210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
                260                 265                 270

Leu Leu Asn Glu Ala Phe Val Val Pro Tyr Gly Thr Pro Leu Gly Val
                275                 280                 285

Asn Phe Gly Pro Thr Val Asp Gly Asp Phe Leu Thr Asp Met Pro Asp
            290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Tyr Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
            370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
            450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
```

```
              515                 520                 525
    Val Leu Glu Met Thr Gly Asn Ile Asp Glu Ala Glu Trp Glu Trp Lys
        530                 535                 540

Ala Gly Phe His Arg Trp Asn Asn Tyr Met Met Asp Trp Lys Asn Gln
    545                 550                 555                 560

Phe Asn Asp Tyr Thr Ser Lys Lys Glu Ser Cys Val Gly Leu
                    565                 570

<210> SEQ ID NO 17
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 17
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg aagtcacat actgaagatg acatcataat tgcaacaaag      240
aatgaaaaag tcagagggat gaacttgaca gttttggtg gcacggtaac agcctttctt      300
ggaattccct atgcacagcc acctcttggt agacttcgat tcaaaaagcc acagtctctg     360
accaagtggt ctgatatttg gaatgccaca aaatatgcaa attcttgctg tcagaacata     420
gatcaaagtt ttccaggctt ccatggatca gagatgtgga cccaaacac tgacctcagt      480 gaagactgtt tatatctaaa tgtatggatt ccagcaccta accaaaaaaa tgccactgta     540
ttgatatgga tttatggtgg tggttttcaa actggaacat catctttaca tgtttatgat     600
ggcaagtttc tggctcgggt tgaaagagtt attgtagtgt caatgaacta tagggtgggt     660
gccctaggat tcttagcttt gccaggaaat cctgaggctc cagggaacat gggtttattt     720
gatcaacagt tggctcttca gtgggttcaa aaaatatag cagcctttgg tggaaatcct      780
aaaagtgtaa ctctctttgg agaaagtgca ggagcagctt cagttagcct gcatttgctt     840
tctcctggaa gccattcatt gttcaccaga gccattctgc aaagtggatc cgcgaatgct     900
ccttgggcgg taacatctct ttatgaagct aggaacagaa cgttgaactt agctaaattg     960
actggttgct ctagagagaa tgagactgaa ataatcaagt gtcttagaaa taaagatccc    1020
caagaaattc ttctgaatga agcatttgtt gtccctatg ggactccttt gtcagtaaac     1080
tttggtccga ccgtggatgg tgatttctc actgacatgc agacatatt acttgaactt      1140 ggacaattta aaaaaccca gatttggtg ggtgttaata agatgaagg acatggttt        1200 ttagtctatg gtgctcctgg cttcagcaaa gataacaata gtatcataac tagaaaagaa    1260
tttcaggaag gtttaaaaat atttttttcca ggagtgagtg agtttggaaa ggaatccatc    1320 cttttttcatt acacagactg ggtagatgat cagagacctg aaaactaccg tgaggccttg    1380
ggtgatgttg ttgggggatta taatttcata tgccctgcct tggagttcac caagaagttc    1440
tcagaatggg gaaataatgc ctttttctac tattttgaac accgatcctc caaacttccg    1500
tggccagaat ggatgggagt gatgcatggc tatgaaattg aatttgtctt tggtttacct    1560
ctggaaagaa gagataatta cacaaaagcc gaggaaattt tgagtagatc catagtgaaa    1620
cggtgggcaa attttgcaaa atatgggaat ccaaatgaga ctcagaacaa tagcacaagc    1680
tggcctgtct tcaaaagcac tgaacaaaaa tatctaacct tgaatacaga gtcaacaaga    1740
```

-continued

```
ataatgacga aactacgtgc tcaacaatgt cgattctgga catcattttt tccaaaagtc    1800
ttggaaatga caggaaatat tgatgaagca gaatgggagt ggaaagcagg attccatcgc    1860
tggaacaatt acatgatgga ctggaaaaat caatttaacg attacactag caagaaagaa    1920
agttgtgtgg gtctctaatt aatagattta ccctttatag aacatatttt cctttagatc    1980
aaggcaaaaa tatcaggagc ttttttacac acctactaaa aaagttatta tgtagctgaa    2040
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttcccccaa aattatcagt gctctgcttt tagtcacgtg tattttcatt     2280
accactcgta aaaggtatc ttttttaaat gaattaaata ttgaaacact gtacaccata     2340
gtttacaata ttatgtttcc taattaaaat aagaattgaa tgtcaatatg agatattaaa    2400
ataagcacag aaaatc                                                    2416

<210> SEQ ID NO 18
<211> LENGTH: 574
<212> TYPE: PRT
<213> ORGANISM: Artificial
<220> FEATURE:
<223> OTHER INFORMATION: Butyrylcholinesterase variant
<220> F

```
                195                 200                 205
Leu Ser Pro Gly Ser His Ser Leu Phe Thr Arg Ala Ile Leu Gln Ser
210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 19
<211> LENGTH: 2416
<212> TYPE: DNA
<213> ORGANISM: Artificial
<220> FEATURE:
<223> OTHER INFORMATION: Butyrylcholinesterase variant
```

```
<400> SEQUENCE: 19
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat actgaagatg acatcataat tgcaacaaag     240
aatggaaaag tcagagggat gaacttgaca gttttggtg gcacggtaac agcctttctt      300
ggaattccct atgcacagcc acctcttggt agacttcgat tcaaaaagcc acagtctctg     360
accaagtggt ctgatatttg gaatgccaca aaatatgcaa attcttgctg tcagaacata     420
gatcaaagtt ttccaggctt ccatggatca gagatgtgga acccaaacac tgacctcagt     480
gaagactgtt tatatctaaa tgtatggatt ccagcaccta aaccaaaaaa tgccactgta     540
ttgatatgga tttatggtgg tggttttcaa actggaacat catctttaca tgtttatgat     600
ggcaagtttc tggctcgggt tgaaagagtt attgtagtgt caatgaacta tagggtgggt     660
gccctaggat tcttagcttt gccaggaaat cctgaggctc agggaacat gggtttattt      720 gatcaacagt tggctcttca gtgggttcaa aaaatatag cagcctttgg tggaaatcct      780
aaaagtgtaa ctctctttgg agaaagtgca ggagcagctt cagttagcct gcatttgctt     840
tctcctggaa gccattcatt gttcaccaga gccattctgc aaagtggatc ctttaatgct     900
ccttgggcgg taacatctct ttatgaagct aggaacagaa cgttgaactt agctaaattg     960
actggttgct ctagagagaa tgagactgaa ataatcaagt gtcttagaaa taaagatccc    1020
caagaaattc ttctgaatga agcatttgtt gtcccctatg ggactccttt gtcagtaaac    1080
tttggtccga ccgtggatgg tgattttctc actgacatgc cagacatatt acttgaactt    1140
ggacaattta aaaaaaccca gattttggtg ggtgttaata agatgaagg acagcttttt    1200 ttagtctcgg gtgctcctgg cttcagcaaa gataacaata gtatcataac tagaaaagaa    1260
tttcaggaag gtttaaaaat attttttcca ggagtgagtg agtttggaaa ggaatccatc    1320 cttttttcatt acacagactg ggtagatgat cagagacctg aaaactaccg tgaggccttg    1380
ggtgatgttg ttggggatta aatttcata tgccctgcct tggagttcac caagaagttc      1440
tcagaatggg gaaataatgc cttttctac tattttgaac accgatcctc caaacttccg      1500
tggccagaat ggatgggagt gatgcatggc tatgaaattg aatttgtctt tggtttacct    1560
ctggaaagaa gagataatta cacaaaagcc gaggaaattt tgagtagatc catagtgaaa    1620
cggtgggcaa attttgcaaa atatgggaat ccaaatgaga ctcagaacaa tagcacaagc    1680
tggcctgtct tcaaaagcac tgaacaaaaa tatctaacct tgaatacaga gtcaacaaga    1740
ataatgacga aactacgtgc tcaacaatgt cgattctgga catcattttt tccaaaagtc    1800
ttggaaatga caggaaatat tgatgaagca gaatgggagt ggaaagcagg attccatcgc    1860
tggaacaatt acatgatgga ctggaaaaat caatttaacg attacactag caagaaagaa    1920
agttgtgtgg gtctctaatt aatagattta ccctttatag aacatatttt cctttagatc    1980
aaggcaaaaa tatcaggagc ttttttacac acctactaaa aaagttatta tgtagctgaa    2040
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttccccccaa aattatcagt gctctgcttt tagtcacgtg tattttcatt    2280
accactcgta aaaaggtatc ttttttaaat gaattaaata ttgaaacact gtacaccata    2340
```

-continued

```
gtttacaata ttatgtttcc taattaaaat aagaattgaa tgtcaatatg agatattaaa    2400
ataagcacag aaaatc                                                    2416
```

<210> SEQ ID NO 20
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (332)..(332)
<223> OTHER INFORMATION: Y332S

<400> SEQUENCE: 20

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320
```

-continued

```
Val Asn Lys Asp Glu Gly Thr Ala Phe Leu Val Ser Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

```

<210> SEQ ID NO 21
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 21
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat actgaagatg acatcataat tgcaacaaag     240
aatggaaaag tcagagggat gaacttgaca gtttttggtg gcacggtaac agcctttctt     300
ggaattccct atgcacagcc acctcttggt agacttcgat tcaaaaagcc acagtctctg     360
accaagtggt ctgatatttg gaatgccaca aaatatgcaa attcttgctg tcagaacata     420
gatcaaagtt ttccaggctt ccatggatca gagatgtgga acccaaacac tgacctcagt     480
gaagactgtt tatatctaaa tgtatggatt ccagcaccta aaccaaaaaa tgccactgta     540
ttgatatgga tttatggtgg tggttttcaa actggaacat catctttaca tgtttatgat     600
ggcaagtttc tggctcgggt tgaaagagtt attgtagtgt caatgaacta tagggtgggt     660
```

```
gccctaggat tcttagcttt gccaggaaat cctgaggctc agggaacat gggtttattt    720
gatcaacagt tggctcttca gtgggttcaa aaaatatag cagcctttgg tggaaatcct    780
aaaagtgtaa ctctctttgg agaaagtgca ggagcagctt cagttagcct gcatttgctt    840
tctcctggaa gccattcatt gttcaccaga gccattctgc aaagtggatc ctttaatgct    900
ccttgggcgg taacatctct ttatgaagct aggaacagaa cgttgaactt agctaaattg    960
actggttgct ctagagagaa tgagactgaa ataatcaagt gtcttagaaa taaagatccc   1020
caagaaattc ttctgaatga agcatttgtt gtccctatg ggactccttt gtcagtaaac   1080
tttggtccga ccgtggatgg tgattttctc actgacatgc agacatatt acttgaactt   1140
ggacaattta aaaaaccca gattttggtg ggtgttaata agatgaagg gacagctttt    1200
ttagtcatgg gtgctcctgg cttcagcaaa gataacaata gtatcataac tagaaaagaa   1260
tttcaggaag gttaaaaat attttttcca ggagtgagtg agtttggaaa ggaatccatc   1320
cttttttcatt acacagactg ggtagatgat cagagacctg aaaactaccg tgaggccttg   1380
ggtgatgttg ttgggggatta taatttcata tgccctgcct tggagttcac caagaagttc   1440
tcagaatggg gaaataatgc cttttttctac tatttttgaac accgatcctc caaacttccg   1500
tggccagaat ggatgggagt gatgcatggc tatgaaattg aatttgtctt tggtttacct   1560
ctggaaagaa gagataatta cacaaaagcc gaggaaattt tgagtagatc catagtgaaa   1620
cggtgggcaa attttgcaaa atatgggaat ccaaatgaga ctcagaacaa tagcacaagc   1680
tggcctgtct tcaaaagcac tgaacaaaaa tatctaacct tgaatacaga gtcaacaaga   1740
ataatgacga aactacgtgc tcaacaatgt cgattctgga catcattttt tccaaaagtc   1800
ttggaaatga caggaaatat tgatgaagca gaatgggagt ggaaagcagg attccatcgc   1860
tggaacaatt acatgatgga ctggaaaaat caatttaacg attacactag caagaaagaa   1920
agttgtgtgg gtctctaatt aatagattta ccctttatag aacatatttt cctttagatc   1980
aaggcaaaaa tatcaggagc ttttttacac acctactaaa aaagttatta tgtagctgaa   2040
acaaaaatgc cagaaggata atattgattc ctcacatctt taacttagta ttttacctag   2100
catttcaaaa cccaaatggc tagaacatgt ttaattaaat ttcacaatat aaagttctac   2160
agttaattat gtgcatatta aaacaatggc ctggttcaat ttctttcttt ccttaataaa   2220
tttaagtttt ttcccccaa aattatcagt gctctgcttt tagtcacgtg tattttcatt   2280
accactcgta aaaaggtatc ttttttaaat gaattaaata ttgaaacact gtacaccata   2340
gtttacaata ttatgtttcc taattaaaat aagaattgaa tgtcaatatg agatattaaa   2400
ataagcacag aaaatc                                                    2416
```

<210> SEQ ID NO 22
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (332)..(332)
<223

-continued

```
                20                  25                  30
Tyr Ala Gln Pro Pro Leu Gly Arg Leu Arg Phe Lys Lys Pro Gln Ser
            35                  40                  45
Leu Thr Lys Trp Ser Asp Ile Trp Asn Ala Thr Lys Tyr Ala Asn Ser
 50                  55                  60
Cys Cys Gln Asn Ile Asp Gln Ser Phe Pro Gly Phe His Gly Ser Glu
 65                  70                  75                  80
Met Trp Asn Pro Asn Thr Asp Leu Ser Glu Asp Cys Leu Tyr Leu Asn
                85                  90                  95
Val Trp Ile Pro Ala Pro Lys Pro Lys Asn Ala Thr Val Leu Ile Trp
            100                 105                 110
Ile Tyr Gly Gly Gly Phe Gln Thr Gly Thr Ser Ser Leu His Val Tyr
            115                 120                 125
Asp Gly Lys Phe Leu Ala Arg Val Glu Arg Val Ile Val Val Ser Met
            130                 135                 140
Asn Tyr Arg Val Gly Ala Leu Gly Phe Leu Leu Pro Gly Asn Pro
145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Gly Asn Pro Lys Ser Val
            180                 185                 190
Thr Leu Phe Gly Glu Ser Ala Gly Ala Ala Ser Val Ser Leu His Leu
            195                 200                 205
Leu Ser Pro Gly Ser His Ser Leu Phe Thr Arg Ala Ile Leu Gln Ser
210                 215                 220
Gly Ser Phe Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
            260                 265                 270
Leu Leu Asn Glu Ala Phe Val Val Pro Tyr Gly Thr Pro Leu Ser Val
            275                 280                 285
Asn Phe Gly Pro Thr Val Asp Gly Asp Phe Leu Thr Asp Met Pro Asp
290                 295                 300
Ile Leu Leu Glu Leu Gly Gln Phe Lys Lys Thr Gln Ile Leu Val Gly
305                 310                 315                 320
Val Asn Lys Asp Glu Gly Thr Ala Phe Leu Val Met Gly Ala Pro Gly
                325                 330                 335
Phe Ser Lys Asp Asn Asn Ser Ile Ile Thr Arg Lys Glu Phe Gln Glu
            340                 345                 350
Gly Leu Lys Ile Phe Phe Pro Gly Val Ser Glu Phe Gly Lys Glu Ser
            355                 360                 365
Ile Leu Phe His Tyr Thr Asp Trp Val Asp Asp Gln Arg Pro Glu Asn
            370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
            420                 425                 430
Trp Met Gly Val Met His Gly Tyr Glu Ile Glu Phe Val Phe Gly Leu
            435                 440                 445
```

-continued

```
Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 23
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 23

```
tactgaatgt cagtgcagtc caatttacag gctggagcag cagctgcatc ctgcatttcc     60
ccgaagtatt acatgatttt cactccttgc aaactttacc atctttgttg cagagaatcg    120
gaaatcaata tgcatagcaa agtcacaatc atatgcatca gatttctctt ttggtttctt    180
ttgctctgca tgcttattgg gaagtcacat actgaagatg acatcataat tgcaacaaag    240
aatggaaaag tcagagggat gaacttgaca gtttttggtg gcacggtaac agcctttctt    300
ggaattccct atgcacagcc acctcttggt agacttcgat tcaaaaagcc acagtctctg    360
accaagtggt ctgatatttg gaatgccaca aaatatgcaa attcttgctg tcagaacata    420
gatcaaagtt ttccaggctt ccatggatca gagatgtgga acccaaacac tgacctcagt    480
gaagactgtt tatatctaaa tgtatggatt ccagcaccta aaccaaaaaa tgccactgta    540
ttgatatgga tttatggtgg tggttttcaa actggaacat catctttaca tgtttatgat    600
ggcaagtttc tggctcgggt tgaaagagtt attgtagtgt caatgaacta tagggtgggt    660
gccctaggat tcttagcttt gccaggaaat cctgaggctc cagggaacat gggtttattt    720
gatcaacagt tggctcttca gtgggttcaa aaaaatatag cagcctttgg tggaaatcct    780
aaaagtgtaa ctctctttgg agaaagtgca ggagcagctt cagttagcct gcatttgctt    840
tctcctggaa gccattcatt gttcaccaga gccattctgc aaagtggatc ctttaatgct    900
ccttgggcgg taacatctct ttatgaagct aggaacagaa cgttgaactt agctaaattg    960
actggttgct ctagagagaa tgagactgaa ataatcaagt gtcttagaaa taaagatccc   1020
caagaaattc ttctgaatga agcatttgtt gtcccctatg ggactccttt gtcagtaaac   1080
tttggtccga ccgtggatgg tgattttctc actgacatgc cagacatatt acttgaactt   1140
ggacaattta aaaaaaccca gattttggtg ggtgttaata aagatgaagg gacagctttt   1200
ttagtcccag gtgctcctgg cttcagcaaa gataacaata gtatcataac tagaaaagaa   1260
tttcaggaag gtttaaaaat attttttcca ggagtgagtg agtttggaaa ggaatccatc   1320
```

-continued

```
cttttttcatt acacagactg ggtagatgat cagagacctg aaaactaccg tgaggccttg    1380
ggtgatgttg ttggggatta taatttcata tgccctgcct ggagttcac caagaagttc     1440
tcagaatggg gaaataatgc ctttttctac tattttgaac accgatcctc caaacttccg    1500
tggccagaat ggatgggagt gatgcatggc tatgaaattg aatttgtctt tggtttacct    1560
ctggaaagaa gagataatta cacaaaagcc gaggaaattt tgagtagatc catagtgaaa    1620
cggtgggcaa attttgcaaa atatgggaat ccaaatgaga ctcagaacaa tagcacaagc    1680
tggcctgtct tcaaaagcac tgaacaaaaa tatctaacct tgaatacaga gtcaacaaga    1740
ataatgacga aactacgtgc tcaacaatgt cgattctgga catcattttt tccaaaagtc    1800
ttggaaatga caggaaatat tgatgaagca gaatgggagt ggaaagcagg attccatcgc    1860
tggaacaatt acatgatgga ctggaaaaat caatttaacg attacactag caagaaagaa    1920
agttgtgtgg gtctctaatt aatagattta ccctttatag aacatatttt cctttagatc    1980
aaggcaaaaa tatcaggagc tttttacac acctactaaa aaagttatta tgtagctgaa     2040
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagttttt ttccccccaa aattatcagt gctctgcttt tagtcacgtg tattttcatt   2280
accactcgta aaaaggtatc ttttttaaat gaattaaata ttgaaacact gtacaccata    2340
gtttacaata ttatgtttcc taattaaaat aagaattgaa tgtcaatatg agatattaaa    2400
ataagcacag aaaatc                                                    2416
```

<210> SEQ ID NO 24
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (332)..(332)
<223> OTHER INFORMATION: Y332P

<400> SEQUENCE: 24

```
Glu Asp Asp Ile Ile Ile Ala Thr Lys Asn Gly Lys Val Ar

```
Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Asn Pro Lys Ser Val
        180                 185                 190

Thr Leu Phe Gly Glu Ser Ala Gly Ala Ala Ser Val Ser Leu His Leu
            195                 200                 205

Leu Ser Pro Gly Ser His Ser Leu Phe Thr Arg Ala Ile Leu Gln Ser
        210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Pro Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
```

-continued

<210> SEQ ID NO 25
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 25

| | | | | | |
|---|---|---|---|---|---|
| tactgaatgt | cagtgcagtc | caatttacag | gctggagcag | cagctgcatc | ctgcatttcc | 60 |
| ccgaagtatt | acatgatttt | cactccttgc | aaactttacc | atctttgttg | cagagaatcg | 120 |
| gaaatcaata | tgcatagcaa | agtcacaatc | atatgcatca | gatttctctt | ttggtttctt | 180 |
| ttgctctgca | tgcttattgg | gaagtcacat | actgaagatg | acatcataat | tgcaacaaag | 240 |
| aatggaaaag | tcagagggat | gaacttgaca | gttttggtg | gcacggtaac | agcctttctt | 300 |
| ggaattccct | atgcacagcc | acctcttggt | agacttcgat | tcaaaaagcc | acagtctctg | 360 |
| accaagtggt | ctgatatttg | gaatgccaca | aaatatgcaa | attcttgctg | tcagaacata | 420 |
| gatcaaagtt | ttccaggctt | ccatggatca | gagatgtgga | acccaaacac | tgacctcagt | 480 |
| gaagactgtt | tatatctaaa | tgtatggatt | ccagcaccta | accaaaaaaa | tgccactgta | 540 |
| ttgatatgga | tttatggtgg | tggttttcaa | actggaacat | catctttaca | tgtttatgat | 600 |
| ggcaagtttc | tggctcgggt | tgaaagagtt | attgtagtgt | caatgaacta | tagggtgggt | 660 |
| gccctaggat | tcttagcttt | gccaggaaat | cctgaggctc | cagggaacat | gggtttattt | 720 |
| gatcaacagt | tggctcttca | gtgggttcaa | aaaaatatag | cagcctttgg | tggaaatcct | 780 |
| aaaagtgtaa | ctctctttgg | agaaagtgca | ggagcagctt | cagttagcct | gcatttgctt | 840 |
| tctcctggaa | gccattcatt | gttcaccaga | gccattctgc | aaagtggatc | ctttaatgct | 900 |
| ccttgggcgg | taacatctct | ttatgaagct | aggaacagaa | cgttaactt | agctaaattg | 960 |
| actggttgct | ctagagagaa | tgagactgaa | ataatcaagt | gtcttagaaa | taaagatccc | 1020 |
| caagaaattc | ttctgaatga | agcatttgtt | gtcccctatg | ggactccttt | gtcagtaaac | 1080 |
| tttggtccga | ccgtggatgg | tgattttctc | actgacatgc | cagacatatt | acttgaactt | 1140 |
| ggacaattta | aaaaaaccca | gattttggtg | ggtgttaata | agatgaagg | gacagctttt | 1200 |
| ttattgtatg | gtgctcctgg | cttcagcaaa | gataacaata | gtatcataac | tagaaaagaa | 1260 |
| tttcaggaag | gtttaaaaat | atttttttcca | ggagtgagtg | agtttggaaa | ggaatccatc | 1320 |
| cttttttcatt | acacagactg | ggtagatgat | cagagacctg | aaaactaccg | tgaggccttg | 1380 |
| ggtgatgttg | ttgggattaa | tttcata | tgccctgcct | tggagttcac | caagaagttc | 1440 |
| tcagaatggg | gaaataatgc | ttttttctac | tattttgaac | accgatcctc | caaacttccg | 1500 |
| tggccagaat | ggatgggagt | gatgcatggc | tatgaaattg | aatttgtctt | tggtttacct | 1560 |
| ctggaaagaa | gagataatta | cacaaaagcc | gaggaaattt | tgagtagatc | catagtgaaa | 1620 |
| cggtgggcaa | attttgcaaa | atatgggaat | ccaaatgaga | ctcagaacaa | tagcacaagc | 1680 |
| tggcctgtct | tcaaaagcac | tgaacaaaaa | tatctaacct | tgaatacaga | gtcaacaaga | 1740 |
| ataatgacga | aactacgtgc | tcaacaatgt | cgattctgga | catcattttt | tccaaaagtc | 1800 |
| ttggaaatga | caggaaatat | tgatgaagca | gaatgggagt | ggaaagcagg | attccatcgc | 1860 |
| tggaacaatt | acatgatgga | ctggaaaaat | caatttaacg | attacactag | caagaaagaa | 1920 |
| agttgtgtgg | gtctctaatt | aatagattta | ccctttatag | aacatatttt | cctttagatc | 1980 |
| aaggcaaaaa | tatcaggagc | ttttttacac | acctactaaa | aaagttatta | tgtagctgaa | 2040 |

-continued

```
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttccccccaa aattatcagt gctctgcttt tagtcacgtg tatttcatt     2280 accactcgta aaaggtatc tttttaaat gaattaaata ttgaaacact gtacaccata      2340
gtttacaata ttatgtttcc taattaaaat aagaattgaa tgtcaatatg agatattaaa    2400
ataagcacag aaaatc                                                    2416
```

<210> SEQ ID NO 26
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (331)..(331)
<223> OTHER INFORMATION: V331L

<400> SEQUENCE: 26

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270
```

-continued

```
Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320
Val Asn Lys Asp Glu Gly Thr Ala Phe Leu Leu Tyr Gly Ala Pro Gly
                325                 330                 335
Phe Ser Lys Asp Asn Asn Ser Ile Ile Thr Arg Lys Glu Phe Gln Glu
            340                 345                 350
Gly Leu Lys Ile Phe Phe Pro Gly Val Ser Glu Phe Gly Lys Glu Ser
        355                 360                 365
Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445
Pro Leu Glu Arg Arg Asp Asn Tyr Thr Lys Ala Glu Glu Ile Leu Ser
    450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
            500                 505                 510
Lys Leu Arg Ala Gln Gln Cys Arg Phe Trp Thr Ser Phe Phe Pro Lys
        515                 520                 525
Val Leu Glu Met Thr Gly Asn Ile Asp Glu Ala Glu Trp Glu Trp Lys
    530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570
```

<210> SEQ ID NO 27
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 27

```
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat actgaagatg acatcataat tgcaacaaag     240
aatggaaaag tcagagggat gaacttgaca gtttttggtg gcacggtaac agcctttctt     300
ggaattccct atgcacagcc acctcttggt agacttcgat tcaaaaagcc acagtctctg     360
```

-continued

```
accaagtggt ctgatatttg gaatgccaca aaatatgcaa attcttgctg tcagaacata    420
gatcaaagtt ttccaggctt ccatggatca gagatgtgga acccaaacac tgacctcagt    480
gaagactgtt tatatctaaa tgtatggatt ccagcaccta aaccaaaaaa tgccactgta    540
ttgatatgga tttatggtgg tggttttcaa actggaacat catctttaca tgtttatgat    600
ggcaagtttc tggctcgggt tgaaagagtt attgtagtgt caatgaacta tagggtgggt    660
gccctaggat tcttagcttt gccaggaaat cctgaggctc agggaacatg ggtttatttt    720
gatcaacagt tggctcttca gtgggttcaa aaaatatag cagcctttgg tggaaatcct    780
aaaagtgtaa ctctctttgg agaaagtgca ggagcagctt cagttagcct gcatttgctt    840
tctcctggaa gccattcatt gttcaccaga gccattctgc aaagtggatc cgcgaatgct    900
ccttgggcgg taacatctct ttatgaagct aggaacagaa cgttgaactt agctaaattg    960
actggttgct ctagagagaa tgagactgaa ataatcaagt gtcttagaaa taaagatccc   1020
caagaaattc ttctgaatga agcatttgtt gtcccctatg ggactccttt gtcagtaaac   1080
tttggtccga ccgtggatgg tgattttctc actgacatgc cagacatatt acttgaactt   1140
ggacaattta aaaaaaccca gattttggtg ggtgttaata agatgaagg acagcttttt   1200
ttagtctatg gtgctcctgg cttcagcaaa gataacaata gtatcataac tagaaaagaa   1260
tttcaggaag gtttaaaaat attttttcca ggagtgagtg agtttggaaa ggaatccatc   1320
cttttttcatt acacagactg ggtagatgat cagagacctg aaaactaccg tgaggccttg   1380
ggtgatgttg ttggggatta aatttcata tgccctgcct tggagttcac caagaagttc   1440
tcagaatggg gaaataatgc cttttctac tattttgaac accgatcctc caaacttccg   1500
tggccagaat ggatgggagt gatgcatggc tatgaaattg aatttgtctt ggtttacct   1560
ctggaaagaa gagataatta cacaaaagcc gaggaaattt tgagtagatc catagtgaaa   1620
cggtgggcaa attttgcaaa atatgggaat ccaaatgaga ctcagaacaa tagcacaagc   1680
tggcctgtct tcaaaagcac tgaacaaaaa tatctaacct tgaatacaga gtcaacaaga   1740
ataatgacga aactacgtgc tcaacaatgt cgattctgga catcattttt tccaaaagtc   1800
ttggaaatga caggaaatat tgatgaagca gaatgggagt ggaaagcagg attccatcgc   1860
tggaacaatt acatgatgga ctggaaaaat caatttaacg attacactag caagaaagaa   1920
agttgtgtgg gtctctaatt aatagattta cccttatag aacatatttt cctttagatc   1980
aaggcaaaaa tatcaggagc ttttttacac acctactaaa aaagttatta tgtagctgaa   2040
acaaaaatgc cagaaggata atattgattc ctcacatctt taacttagta ttttacctag   2100
catttcaaaa cccaaatggc tagaacatgt ttaattaaat ttcacaatat aaagttctac   2160
agttaattat gtgcatatta aaacaatggc ctggttcaat ttctttcttt ccttaataaa   2220
tttaagtttt ttcccccccaa aattatcagt gctctgcttt tagtcacgtg tattttcatt   2280
accactcgta aaaaggtatc ttttttaaat gaattaaata ttgaaacact gtacaccata   2340
gtttacaata ttatgtttcc taattaaaat aagaattgaa tgtcaatatg agatattaaa   2400
ataagcacag aaaatc                                                    2416
```

<210> SEQ ID NO 28
<211> LENGTH: 574
<212> TYPE: PRT
<213> ORGANISM: Artificial
<220> FEATURE:
<223> OTHER INFORMATION: Butyrylcholinesterase variant
<220> FEATURE:

<221> NAME/KEY: MISC_FEATURE
<222> LOCATION: (227)..(227)
<223> OTHER INFORMATION: F227A

<400> SEQUENCE: 28

| | | | | | | | | | | | | | | |
|---|---|---|---|---|---|---|---|---|---|---|---|---|---|---|
| Glu | Asp | Asp | Ile | Ile | Ile | Ala | Thr | Lys | Asn | Gly | Lys | Val | Arg | Gly | Met |
| 1 | | | | 5 | | | | | 10 | | | | | 15 | |
| Asn | Leu | Thr | Val | Phe | Gly | Gly | Thr | Val | Thr | Ala | Phe | Leu | Gly | Ile | Pro |
| | | | 20 | | | | | 25 | | | | | 30 | | |
| Tyr | Ala | Gln | Pro | Pro | Leu | Gly | Arg | Leu | Arg | Phe | Lys | Lys | Pro | Gln | Ser |
| | | | 35 | | | | | 40 | | | | | 45 | | |
| Leu | Thr | Lys | Trp | Ser | Asp | Ile | Trp | Asn | Ala | Thr | Lys | Tyr | Ala | Asn | Ser |
| | 50 | | | | | 55 | | | | | 60 | | | | |
| Cys | Cys | Gln | Asn | Ile | Asp | Gln | Ser | Phe | Pro | Gly | Phe | His | Gly | Ser | Glu |
| 65 | | | | | 70 | | | | | 75 | | | | | 80 |
| Met | Trp | Asn | Pro | Asn | Thr | Asp | Leu | Ser | Glu | Asp | Cys | Leu | Tyr | Leu | Asn |
| | | | | 85 | | | | | 90 | | | | | 95 | |
| Val | Trp | Ile | Pro | Ala | Pro | Lys | Pro | Lys | Asn | Ala | Thr | Val | Leu | Ile | Trp |
| | | | | 100 | | | | | 105 | | | | | 110 | |
| Ile | Tyr | Gly | Gly | Gly | Phe | Gln | Thr | Gly | Thr | Ser | Ser | Leu | His | Val | Tyr |
| | | | 115 | | | | | 120 | | | | | 125 | | |
| Asp | Gly | Lys | Phe | Leu | Ala | Arg | Val | Glu | Arg | Val | Ile | Val | Ser | Met | |
| | 130 | | | | | 135 | | | | | 140 | | | | |
| Asn | Tyr | Arg | Val | Gly | Ala | Leu | Gly | Phe | Leu | Ala | Leu | Pro | Gly | Asn | Pro |
| 145 | | | | | 150 | | | | | 155 | | | | | 160 |
| Glu | Ala | Pro | Gly | Asn | Met | Gly | Leu | Phe | Asp | Gln | Gln | Leu | Ala | Leu | Gln |
| | | | | 165 | | | | | 170 | | | | | 175 | |
| Trp | Val | Gln | Lys | Asn | Ile | Ala | Ala | Phe | Gly | Gly | Asn | Pro | Lys | Ser | Val |
| | | | 180 | | | | | 185 | | | | | 190 | | |
| Thr | Leu | Phe | Gly | Glu | Ser | Ala | Gly | Ala | Ala | Ser | Val | Ser | Leu | His | Leu |
| | | | 195 | | | | | 200 | | | | | 205 | | |
| Leu | Ser | Pro | Gly | Ser | His | Ser | Leu | Phe | Thr | Arg | Ala | Ile | Leu | Gln | Ser |
| | 210 | | | | | 215 | | | | | 220 | | | | |
| Gly | Ser | Ala | Asn | Ala | Pro | Trp | Ala | Val | Thr | Ser | Leu | Tyr | Glu | Ala | Arg |
| 225 | | | | | 230 | | | | | 235 | | | | | 240 |
| Asn | Arg | Thr | Leu | Asn | Leu | Ala | Lys | Leu | Thr | Gly | Cys | Ser | Arg | Glu | Asn |
| | | | | 245 | | | | | 250 | | | | | 255 | |
| Glu | Thr | Glu | Ile | Ile | Lys | Cys | Leu | Arg | Asn | Lys | Asp | Pro | Gln | Glu | Ile |
| | | | 260 | | | | | 265 | | | | | 270 | | |
| Leu | Leu | Asn | Glu | Ala | Phe | Val | Val | Pro | Tyr | Gly | Thr | Pro | Leu | Ser | Val |
| | | 275 | | | | | 280 | | | | | 285 | | | |
| Asn | Phe | Gly | Pro | Thr | Val | Asp | Gly | Asp | Phe | Leu | Thr | Asp | Met | Pro | Asp |
| | 290 | | | | | 295 | | | | | 300 | | | | |
| Ile | Leu | Leu | Glu | Leu | Gly | Gln | Phe | Lys | Lys | Thr | Gln | Ile | Leu | Val | Gly |
| 305 | | | | | 310 | | | | | 315 | | | | | 320 |
| Val | Asn | Lys | Asp | Glu | Gly | Thr | Ala | Phe | Leu | Val | Tyr | Gly | Ala | Pro | Gly |
| | | | | 325 | | | | | 330 | | | | | 335 | |
| Phe | Ser | Lys | Asp | Asn | Asn | Ser | Ile | Ile | Thr | Arg | Lys | Glu | Phe | Gln | Glu |
| | | | 340 | | | | | 345 | | | | | 350 | | |
| Gly | Leu | Lys | Ile | Phe | Phe | Pro | Gly | Val | Ser | Glu | Phe | Gly | Lys | Glu | Ser |
| | | | 355 | | | | | 360 | | | | | 365 | | |
| Ile | Leu | Phe | His | Tyr | Thr | Asp | Trp | Val | Asp | Asp | Gln | Arg | Pro | Glu | Asn |
| | 370 | | | | | 375 | | | | | 380 | | | | |
| Tyr | Arg | Glu | Ala | Leu | Gly | Asp | Val | Val | Gly | Asp | Tyr | Asn | Phe | Ile | Cys |

-continued

```
           385                 390                 395                 400
Pro Ala Leu Glu Phe Thr Lys Lys Phe Ser Glu Trp Gly Asn Asn Ala
                    405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
        450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 29
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 29

```
tactgaatgt cagtgcagtc caatttacag gctggagcag cagctgcatc ctgcatttcc      60
ccgaagtatt acatgatttt cactccttgc aaacttacc atctttgttg cagagaatcg     120
gaaatcaata tgcatagcaa agtcacaatc atatgcatca gatttctctt ttggtttctt     180
ttgctctgca tgcttattgg gaagtcacat actgaagatg acatcataat tgcaacaaag     240
aatggaaaag tcagagggat gaacttgaca gttttggtg gcacggtaac agcctttctt     300
ggaattccct atgcacagcc acctcttggt agacttcgat tcaaaaagcc acagtctctg     360
accaagtggt ctgatatttg gaatgccaca aaatatgcaa attcttgctg tcagaacata     420
gatcaaagtt tccaggctt ccatggatca gagatgtgga cccaaacac tgacctcagt     480
gaagactgtt tatatctaaa tgtatggatt ccagcaccta accaaaaaaa tgccactgta     540
ttgatatgga tttatggtgg tggttttcaa actggaacat catctttaca tgtttatgat     600
ggcaagtttc tggctcgggt tgaaagagtt attgtagtgt caatgaacta tagggtgggt     660
gccctaggat tcttagcttt gccaggaaat cctgaggctc cagggaacat gggtttattt     720
gatcaacagt tggctcttca gtgggttcaa aaaatatag cagcctttgg tggaaatcct     780
aaaagtgtaa ctctctttgg agaaagtgca ggagcagctt cagttagcct gcatttgctt     840
tctcctggaa gccattcatt gttcaccaga gccattctgc aaagtggatc cgggaatgct     900
ccttgggcgg taacatctct ttatgaagct aggaacagaa cgttgaactt agctaaattg     960
actggttgct ctagagagaa tgagactgaa ataatcaagt gtcttagaaa taaagatccc    1020
```

```
caagaaattc ttctgaatga agcatttgtt gtccctatg ggactccttt gtcagtaaac    1080
tttggtccga ccgtggatgg tgattttctc actgacatgc cagacatatt acttgaactt    1140
ggacaattta aaaaaccca gattttggtg ggtgttaata aagatgaagg gacagctttt    1200
ttagtctatg gtgctcctgg cttcagcaaa gataacaata gtatcataac tagaaaagaa    1260
tttcaggaag gtttaaaaat attttttcca ggagtgagtg agtttggaaa ggaatccatc    1320 cttttcatt acacagactg ggtagatgat cagagacctg aaaactaccg tgaggccttg    1380
ggtgatgttg ttgggggatta taatttcata tgccctgcct tggagttcac caagaagttc    1440
tcagaatggg gaaataatgc cttttctac tattttgaac accgatcctc caaacttccg    1500
tggccagaat ggatgggagt gatgcatggc tatgaaattg aatttgtctt tggttacct    1560 ctggaaagaa gagataatta cacaaaagcc gaggaaattt tgagtagatc catagtgaaa    1620
cggtgggcaa attttgcaaa atatgggaat ccaaatgaga ctcagaacaa tagcacaagc    1680
tggcctgtct tcaaaagcac tgaacaaaaa tatctaacct tgaatacaga gtcaacaaga    1740
ataatgacga aactacgtgc tcaacaatgt cgattctgga catcattttt tccaaaagtc    1800
ttggaaatga caggaaatat tgatgaagca gaatgggagt ggaaagcagg attccatcgc    1860
tggaacaatt acatgatgga ctggaaaaat caatttaacg attacactag caagaaagaa    1920
agttgtgtgg gtctctaatt aatagattta ccctttatag aacatatttt cctttagatc    1980
aaggcaaaaa tatcaggagc ttttttacac acctactaaa aaagttatta tgtagctgaa    2040
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttccccccaa aattatcagt gctctgcttt tagtcacgtg tatttttcatt    2280 accactcgta aaaggtatc ttttttaaat gaattaaata ttgaaacact gtacaccata    2340
gtttacaata ttatgtttcc taattaaaat aagaattgaa tgtcaatatg agatattaaa    2400
ataagcacag aaaatc                                                   2416
```

<210> SEQ ID NO 30
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (227)..(227)
<223> OTHER INFORMATION:

```
Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
            115                 120                 125

Asp Gly Lys Phe Leu Ala Arg Val Glu Arg Val Ile Val Val Ser Met
            130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
            195                 200                 205

Leu Ser Pro Gly Ser His Ser Leu Phe Thr Arg Ala Ile Leu Gln Ser
            210                 215                 220

Gly Ser Gly Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
            275                 280                 285

Asn Phe Gly Pro Thr Val Asp Gly Asp Phe Leu Thr Asp Met Pro Asp
            290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
            370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510
```

-continued

```
Lys Leu Arg Ala Gln Gln Cys Arg Phe Trp Thr Ser Phe Phe Pro Lys
        515                 520                 525
Val Leu Glu Met Thr Gly Asn Ile Asp Glu Ala Glu Trp Glu Trp Lys
    530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570
```

<210> SEQ ID NO 31
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 31

```
tactgaatgt cagtgcagtc caatttacag gctggagcag cagctgcatc ctgcatttcc     60
ccgaagtatt acatgatttt cactccttgc aaactttacc atctttgttg cagagaatcg    120
gaaatcaata tgcatagcaa agtcacaatc atatgcatca gatttctctt ttggtttctt    180
ttgctctgca tgcttattgg gaagtcacat actgaagatg acatcataat tgcaacaaag    240
aatggaaaag tcagagggat gaacttgaca gtttttggtg gcacggtaac agcctttctt    300
ggaattccct atgcacagcc acctcttggt agacttcgat tcaaaaagcc acagtctctg    360
accaagtggt ctgatatttg gaatgccaca aaatatgcaa attcttgctg tcagaacata    420
gatcaaagtt ttccaggctt ccatggatca gagatgtgga acccaaacac tgacctcagt    480
gaagactgtt tatatctaaa tgtatggatt ccagcaccta aaccaaaaaa tgccactgta    540
ttgatatgga tttatggtgg tggttttcaa actggaacat catctttaca tgtttatgat    600
ggcaagtttc tggctcgggt tgaaagagtt attgtagtgt caatgaacta tagggtgggt    660
gccctaggat tcttagcttt gccaggaaat cctgaggctc cagggaacat gggtttattt    720
gatcaacagt tggctcttca gtgggttcaa aaaaatatag cagcctttgg tggaaatcct    780
aaaagtgtaa ctctctttgg agaaagtgca ggagcagctt cagttagcct gcatttgctt    840
tctcctggaa gccattcatt gttcaccaga gccattctgc aaagtggatc cagtaatgct    900
ccttgggcgg taacatctct ttatgaagct aggaacagaa cgttgaactt agctaaattg    960
actggttgct ctagagagaa tgagactgaa ataatcaagt gtcttagaaa taaagatccc   1020
caagaaattc ttctgaatga agcatttgtt gtcccctatg ggactccttt gtcagtaaac   1080
tttggtccga ccgtggatgg tgattttctc actgacatgc cagacatatt acttgaactt   1140
ggacaattta aaaaaaccca gattttggtg ggtgttaata aagatgaagg gacagctttt   1200
ttagtctatg gtgctcctgg cttcagcaaa gataacaata gtatcataac tagaaaagaa   1260
tttcaggaag gtttaaaaat atttttttcca ggagtgagtg agtttggaaa ggaatccatc   1320
ctttttcatt acacagactg ggtagatgat cagagacctg aaaactaccg tgaggccttg   1380
ggtgatgttg ttggggatta taatttcata tgccctgcct tggagttcac caagaagttc   1440
tcagaatggg gaaataatgc ctttttctac tattttgaac accgatcctc caaacttccg   1500
tggccagaat ggatgggagt gatgcatggc tatgaaattg aatttgtctt tggtttacct   1560
ctggaaagaa gagataatta cacaaaagcc gaggaaattt tgagtagatc catagtgaaa   1620
cggtgggcaa attttgcaaa atatgggaat ccaaatgaga ctcagaacaa tagcacaagc   1680
tggcctgtct tcaaaagcac tgaacaaaaa tatctaacct tgaatacaga gtcaacaaga   1740
```

-continued

```
ataatgacga aactacgtgc tcaacaatgt cgattctgga catcattttt tccaaaagtc    1800
ttggaaatga caggaaatat tgatgaagca gaatgggagt ggaaagcagg attccatcgc    1860
tggaacaatt acatgatgga ctggaaaaat caatttaacg attacactag caagaaagaa    1920
agttgtgtgg gtctctaatt aatagattta ccctttatag aacatatttt cctttagatc    1980
aaggcaaaaa tatcaggagc ttttttacac acctactaaa aaagttatta tgtagctgaa    2040
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttcccccccaa aattatcagt gctctgcttt tagtcacgtg tatttttcatt   2280 accactcgta aaaggtatc ttttttaaat gaattaaata ttgaaacact gtacaccata    2340
gtttacaata ttatgtttcc taattaaaat aagaattgaa tgtcaatatg agatattaaa    2400
ataagcacag aaaatc                                                     2416
```

<210> SEQ ID NO 32
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (227)..(227)
<223> OTHER INFORMATION: F227S

<400> SEQUENCE:

```
                    210                 215                 220
Gly Ser Ser Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
                260                 265                 270

Leu Leu Asn Glu Ala Phe Val Val Pro Tyr Gly Thr Pro Leu Ser Val
            275                 280                 285

Asn Phe Gly Pro Thr Val Asp Gly Asp Phe Leu Thr Asp Met Pro Asp
290                 295                 300

Ile Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
                500                 505                 510

Lys Leu Arg Ala Gln Gln Cys Arg Phe Trp Thr Ser Phe Phe Pro Lys
            515                 520                 525

Val Leu Glu Met Thr Gly Asn Ile Asp Glu Ala Glu Trp Glu Trp Lys
530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 33
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 33
tactgaatgt cagtgcagtc caatttacag gctggagcag cagctgcatc ctgcatttcc    60

-continued

```
ccgaagtatt acatgatttt cactccttgc aaactttacc atctttgttg cagagaatcg    120
gaaatcaata tgcatagcaa agtcacaatc atatgcatca gatttctctt ttggtttctt    180
ttgctctgca tgcttattgg gaagtcacat actgaagatg acatcataat tgcaacaaag    240
aatggaaaag tcagagggat gaacttgaca gttttggtg gcacggtaac agcctttctt    300
ggaattccct atgcacagcc acctcttggt agacttcgat tcaaaaagcc acagtctctg    360
accaagtggt ctgatatttg aatgccaca aaatatgcaa attcttgctg tcagaacata    420
gatcaaagtt ttccaggctt ccatggatca gagatgtgga acccaaacac tgacctcagt    480
gaagactgtt tatatctaaa tgtatggatt ccagcaccta aaccaaaaaa tgccactgta    540
ttgatatgga tttatggtgg tggttttcaa actggaacat catctttaca tgtttatgat    600
ggcaagtttc tggctcgggt tgaaagagtt attgtagtgt caatgaacta tagggtgggt    660
gccctaggat tcttagcttt gccaggaaat cctgaggctc cagggaacat gggtttattt    720
gatcaacagt tggctcttca gtgggttcaa aaaatatag cagcctttgg tggaaatcct    780
aaaagtgtaa ctctctttgg agaaagtgca ggagcagctt cagttagcct gcatttgctt    840
tctcctggaa gccattcatt gttcaccaga gccattctgc aaagtggatc cccgaatgct    900
ccttgggcgg taacatctct ttatgaagct aggaacagaa cgttgaactt agctaaattg    960
actggttgct ctagagagaa tgagactgaa ataatcaagt gtcttagaaa taaagatccc   1020
caagaaattc ttctgaatga agcatttgtt gtcccctatg ggactccttt gtcagtaaac   1080
tttggtccga ccgtggatgg tgattttctc actgacatgc cagacatatt acttgaactt   1140
ggacaattta aaaaaaccca gattttggtg ggtgttaata agatgaagg acagcttttt   1200
ttagtctatg gtgctcctgg cttcagcaaa gataacaata gtatcataac tagaaaagaa   1260
tttcaggaag gttaaaaat atttttttcca ggagtgagtg agtttggaaa ggaatccatc   1320
cttttcatt acacagactg ggtagatgat cagagacctg aaaactaccg tgaggccttg   1380
ggtgatgttg ttgggggatta taatttcata tgccctgcct tggagttcac caagaagttc   1440
tcagaatggg gaaataatgc ctttttctac tattttgaac accgatcctc caaacttccg   1500
tggccagaat ggatgggagt gatgcatggc tatgaaattg aatttgtctt tggtttacct   1560
ctggaaagaa gagataatta cacaaaagcc gaggaaattt tgagtagatc catagtgaaa   1620
cggtgggcaa attttgcaaa atatgggaat ccaaatgaga ctcagaacaa tagcacaagc   1680
tggcctgtct tcaaaagcac tgaacaaaaa tatctaacct tgaatacaga gtcaacaaga   1740
ataatgacga aactacgtgc tcaacaatgt cgattctgga catcattttt tccaaaagtc   1800
ttggaaatga caggaaatat tgatgaagca gaatgggagt ggaaagcagg attccatcgc   1860
tggaacaatt acatgatgga ctggaaaaat caatttaacg attacactag caagaaagaa   1920
agttgtgtgg gtctctaatt aatagattta ccctttatag aacatatttt cctttagatc   1980
aaggcaaaaa tatcaggagc ttttttacac acctactaaa aaagttatta tgtagctgaa   2040
acaaaaatgc cagaaggata atattgattc ctcacatctt taacttagta ttttacctag   2100
catttcaaaa cccaaatggc tagaacatgt ttaattaaat ttcacaatat aaagttctac   2160
agttaattat gtgcatatta aaacaatggc ctggttcaat ttctttcttt ccttaataaa   2220
tttaagtttt ttccccccaa aattatcagt gctctgcttt tagtcacgtg tattttcatt   2280
accactcgta aaaggtatc ttttttaaat gaattaaata ttgaaacact gtacaccata   2340
gtttacaata ttatgtttcc taattaaaat aagaattgaa tgtcaatatg agatattaaa   2400
```

-continued ataagcacag aaaatc 2416

<210> SEQ ID NO 34
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (227)..(227)
<223> OTHER INFORMATION: F227P

<400> SEQUENCE: 34

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Pro Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335
```

-continued

```
Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
            420                 425                 430
Trp Met Gly Val Met His Gly Tyr Glu Ile Glu Phe Val Phe Gly Leu
        435                 440                 445
Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
            500                 505                 510
Lys Leu Arg Ala Gln Gln Cys Arg Phe Trp Thr Ser Phe Phe Pro Lys
        515                 520                 525
Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570

<210> SEQ ID NO 35
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 35
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat actgaagatg acatcataat tgcaacaaag     240
aatggaaaag tcagagggat gaacttgaca gtttttggtg gcacggtaac agcctttctt     300
ggaattccct atgcacagcc acctcttggt agacttcgat tcaaaaagcc acagtctctg     360
accaagtggt ctgatatttg gaatgccaca aaatatgcaa attcttgctg tcagaacata     420
gatcaaagtt ttccaggctt ccatggatca gagatgtgga acccaaacac tgacctcagt     480
gaagactgtt tatatctaaa tgtatggatt ccagcaccta aaccaaaaaa tgccactgta     540
ttgatatgga tttatggtgg tggttttcaa actggaacat catctttaca tgtttatgat     600
ggcaagtttc tggctcgggt tgaaagagtt attgtagtgt caatgaacta tagggtgggt     660
gccctaggat tcttagcttt gccaggaaat cctgaggctc cagggaacat gggtttattt     720
```

-continued

```
gatcaacagt tggctcttca gtgggttcaa aaaaatatag cagcctttgg tggaaatcct      780
aaaagtgtaa ctctctttgg agaaagtgca ggagcagctt cagttagcct gcatttgctt      840
tctcctggaa gccattcatt gttcaccaga gccattctgc aaagtggatc cactaatgct      900
ccttgggcgg taacatctct ttatgaagct aggaacagaa cgttgaactt agctaaattg      960
actggttgct ctagagagaa tgagactgaa ataatcaagt gtcttagaaa taaagatccc     1020
caagaaattc ttctgaatga agcatttgtt gtcccctatg ggactccttt gtcagtaaac     1080
tttggtccga ccgtggatgg tgattttctc actgacatgc agacatatt acttgaactt      1140
ggacaattta aaaaaccca gattttggtg ggtgttaata agatgaagg gacagctttt       1200
ttagtctatg gtgctcctgg cttcagcaaa gataacaata gtatcataac tagaaaagaa     1260
tttcaggaag gtttaaaaat atttttcca ggagtgagtg agtttggaaa ggaatccatc      1320
ctttttcatt acacagactg ggtagatgat cagagacctg aaaactaccg tgaggccttg     1380
ggtgatgttg ttggggatta aatttcata tgccctgcct tggagttcac caagaagttc      1440
tcagaatggg gaaataatgc cttttctac tattttgaac accgatcctc caaacttccg      1500
tggccagaat ggatgggagt gatgcatggc tatgaaattg aatttgtctt tggtttacct     1560
ctggaaagaa gagataatta cacaaaagcc gaggaaattt tgagtagatc catagtgaaa     1620
cggtgggcaa attttgcaaa atatgggaat ccaaatgaga ctcagaacaa tagcacaagc     1680
tggcctgtct tcaaaagcac tgaacaaaaa tatctaacct gaatacaga gtcaacaaga     1740
ataatgacga aactacgtgc tcaacaatgt cgattctgga catcatttt tccaaaagtc     1800
ttggaaatga caggaaatat tgatgaagca gaatgggagt ggaaagcagg attccatcgc     1860
tggaacaatt acatgatgga ctggaaaaat caatttaacg attacactag caagaaagaa     1920
agttgtgtgg gtctctaatt aatagattta ccctttatag aacatatttt cctttagatc     1980
aaggcaaaaa tatcaggagc ttttttacac acctactaaa aaagttatta tgtagctgaa     2040
acaaaaatgc cagaaggata atattgattc ctcacatctt aacttagta ttttacctag      2100
catttcaaaa cccaaatggc tagaacatgt ttaattaaat ttcacaatat aaagttctac     2160
agttaattat gtgcatatta aaacaatggc ctggttcaat ttctttcttt ccttaataaa     2220
tttaagtttt ttccccccaa aattatcagt gctctgcttt tagtcacgtg tattttcatt     2280
accactcgta aaaggtatc tttttaaat gaattaaata ttgaaacact gtacaccata      2340
gtttacaata ttatgtttcc taattaaaat aagaattgaa tgtcaatatg agatattaaa     2400
ataagcacag aaaatc                                                    2416
```

<210> SEQ ID NO 36
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (227)..(227)
<223> OTHER INFORMATION: F227T

<400> SEQUENCE: 36

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
```

-continued

```
            35                  40                  45
Leu Thr Lys Trp Ser Asp Ile Trp Asn Ala Thr Lys Tyr Ala Asn Ser
 50                  55                  60

Cys Cys Gln Asn Ile Asp Gln Ser Phe Pro Gly Phe His Gly Ser Glu
 65                  70                  75                  80

Met Trp Asn Pro Asn Thr Asp Leu Ser Glu Asp Cys Leu Tyr Leu Asn
                 85                  90                  95

Val Trp Ile Pro Ala Pro Lys Pro Lys Asn Ala Thr Val Leu Ile Trp
                100                 105                 110

Ile Tyr Gly Gly Gly Phe Gln Thr Gly Thr Ser Ser Leu His Val Tyr
            115                 120                 125

Asp Gly Lys Phe Leu Ala Arg Val Glu Arg Val Ile Val Val Ser Met
130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
                180                 185                 190

Thr Leu Phe Gly Glu Ser Ala Gly Ala Ala Ser Val Ser Leu His Leu
            195                 200                 205

Leu Ser Pro Gly Ser His Ser Leu Phe Thr Arg Ala Ile Leu Gln Ser
210                 215                 220

Gly Ser Thr Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
                260                 265                 270

Leu Leu Asn Glu Ala Phe Val Val Pro Tyr Gly Thr Pro Leu Ser Val
            275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
450                 455                 460
```

```
Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 37
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 37
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat actgaagatg acatcataat tgcaacaaag     240
aatggaaaag tcagagggat gaacttgaca gttttggtg gcacggtaac agcctttctt      300
ggaattccct atgcacagcc acctcttggt agacttcgat tcaaaaagcc acagtctctg     360
accaagtggt ctgatatttg aatgccaca aaatatgcaa attcttgctg tcagaacata      420
gatcaaagtt ttccaggctt ccatggatca gagatgtgga acccaaacac tgacctcagt     480
gaagactgtt tatatctaaa tgtatggatt ccagcaccta accaaaaaa tgccactgta      540 ttgatatgga tttatggtgg tggttttcaa actggaacat catctttaca tgtttatgat     600
ggcaagtttc tggctcgggt tgaaagagtt attgtagtgt caatgaacta tagggtgggt     660
gccctaggat tcttagcttt gccaggaaat cctgaggctc agggaacat gggttattt      720 gatcaacagt tggctcttca gtgggttcaa aaaaatatag cagcctttgg tggaaatcct     780
aaaagtgtaa ctctctttgg agaaagtgca ggagcagctt cagttagcct gcatttgctt     840
tctcctggaa gccattcatt gttcaccaga gccattctgc aaagtggatc ctgtaatgct     900
ccttgggcgg taacatctct ttatgaagct aggaacagaa cgttgaactt agctaaattg     960
actggttgct ctagagagaa tgagactgaa ataatcaagt gtcttagaaa taagatccc     1020 caagaaattc ttctgaatga agcatttgtt gtcccctatg gactcctttt gtcagtaaac    1080
tttggtccga ccgtggatgg tgattttctc actgacatgc agacatatt acttgaactt     1140 ggacaattta aaaaaccca gattttggtg ggtgttaata agatgaagg gacagctttt     1200 ttagtctatg gtgctcctgg cttcagcaaa gataacaata tgtcataac tagaaaagaa      1260 tttcaggaag gtttaaaat atttttccca ggagtgagtg agtttggaaa ggaatccatc     1320 cttttttcatt acacagactg ggtagatgat cagagacctg aaaactaccg tgaggccttg    1380
ggtgatgttg ttgggggatta taatttcata tgccctgcct tggagttcac caagaagttc    1440
```

```
tcagaatggg gaaataatgc cttttctac tattttgaac accgatcctc caaacttccg    1500
tggccagaat ggatgggagt gatgcatggc tatgaaattg aatttgtctt tggtttacct    1560
ctggaaagaa gagataatta cacaaaagcc gaggaaattt tgagtagatc catagtgaaa    1620
cggtgggcaa attttgcaaa atatgggaat ccaaatgaga ctcagaacaa tagcacaagc    1680
tggcctgtct tcaaaagcac tgaacaaaaa tatctaacct tgaatacaga gtcaacaaga    1740
ataatgacga aactacgtgc tcaacaatgt cgattctgga catcattttt tccaaaagtc    1800
ttggaaatga caggaaatat tgatgaagca gaatgggagt ggaaagcagg attccatcgc    1860
tggaacaatt acatgatgga ctggaaaaat caatttaacg attacactag caagaaagaa    1920
agttgtgtgg gtctctaatt aatagattta ccctttatag aacatatttt cctttagatc    1980
aaggcaaaaa tatcaggagc ttttttacac acctactaaa aaagttatta tgtagctgaa    2040
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttccccccaa aattatcagt gctctgcttt tagtcacgtg tatttcatt    2280 accactcgta aaaggtatc ttttttaaat gaattaaata ttgaaacact gtacaccata    2340
gtttacaata ttatgtttcc taattaaaat aagaattgaa tgtcaatatg agatattaaa    2400
ataagcacag aaaatc                                                    2416
```

<210> SEQ ID NO 38
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (227)..(227)
<223> OTHER INFORMATION: F227C

<400> SEQUENCE: 38

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160
```

-continued

```
Glu Ala Pro Gly Asn Met Gly Leu Phe Asp Gln Gln Leu Ala Leu Gln
            165                 170                 175

Trp Val Gln Lys Asn Ile Ala Ala Phe Gly Gly Asn Pro Lys Ser Val
        180                 185                 190

Thr Leu Phe Gly Glu Ser Ala Gly Ala Ala Ser Val Ser Leu His Leu
    195                 200                 205

Leu Ser Pro Gly Ser His Ser Leu Phe Thr Arg Ala Ile Leu Gln Ser
210                 215                 220

Gly Ser Cys Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

-continued

```
<210> SEQ ID NO 39
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 39
```
tactgaatgt cagtgcagtc caatttacag gctggagcag cagctgcatc ctgcatttcc 60
ccgaagtatt acatgatttt cactccttgc aaactttacc atctttgttg cagagaatcg 120
gaaatcaata tgcatagcaa agtcacaatc atatgcatca gatttctctt ttggtttctt 180
ttgctctgca tgcttattgg gaagtcacat actgaagatg acatcataat tgcaacaaag 240
aatggaaaag tcagagggat gaacttgaca gtttttggtg gcacggtaac agcctttctt 300
ggaattccct atgcacagcc acctcttggt agacttcgat tcaaaaagcc acagtctctg 360
accaagtggt ctgatatttg gaatgccaca aaatatgcaa attcttgctg tcagaacata 420
gatcaaagtt ttccaggctt ccatggatca gagatgtgga acccaaacac tgacctcagt 480
gaagactgtt tatatctaaa tgtatggatt ccagcaccta aaccaaaaaa tgccactgta 540
ttgatatgga tttatggtgg tggttttcaa actggaacat catctttaca tgtttatgat 600
ggcaagtttc tggctcgggt tgaaagagtt attgtagtgt caatgaacta tagggtgggt 660
gccctaggat tcttagcttt gccaggaaat cctgaggctc cagggaacat gggtttattt 720
gatcaacagt tggctcttca gtgggttcaa aaaaatatag cagcctttgg tggaaatcct 780
aaaagtgtaa ctctctttgg agaaagtgca ggagcagctt cagttagcct gcatttgctt 840
tctcctggaa gccattcatt gttcaccaga gccattctgc aaagtggatc catgaatgct 900
ccttgggcgg taacatctct ttatgaagct aggaacagaa cgttgaactt agctaaattg 960
actggttgct ctagagagaa tgagactgaa ataatcaagt gtcttagaaa taaagatccc 1020
caagaaattc ttctgaatga agcatttgtt gtcccctatg ggactccttt gtcagtaaac 1080
tttggtccga ccgtggatgg tgattttctc actgacatgc cagacatatt acttgaactt 1140
ggacaattta aaaaaaccca gattttggtg ggtgttaata aagatgaagg gacagctttt 1200
ttagtctatg gtgctcctgg cttcagcaaa gataacaata gtatcataac tagaaaagaa 1260
tttcaggaag gtttaaaaat attttttcca ggagtgagtg agtttggaaa ggaatccatc 1320
ctttttcatt acacagactg ggtagatgat cagagacctg aaaactaccg tgaggccttg 1380
ggtgatgttg ttggggatta taatttcata tgccctgcct tggagttcac caagaagttc 1440
tcagaatggg gaaataatgc ctttttctac tattttgaac accgatcctc caaacttccg 1500
tggccagaat ggatgggagt gatgcatggc tatgaaattg aatttgtctt tggtttacct 1560
ctggaaagaa gagataatta cacaaaagcc gaggaaattt tgagtagatc catagtgaaa 1620
cggtgggcaa attttgcaaa atatgggaat ccaaatgaga ctcagaacaa tagcacaagc 1680
tggcctgtct tcaaaagcac tgaacaaaaa tatctaacct tgaatacaga gtcaacaaga 1740
ataatgacga aactacgtgc tcaacaatgt cgattctgga catcattttt tccaaaagtc 1800
ttggaaatga caggaaatat tgatgaagca gaatgggagt ggaaagcagg attccatcgc 1860
tggaacaatt acatgatgga ctggaaaaat caatttaacg attacactag caagaaagaa 1920
agttgtgtgg gtctctaatt aatagattta ccctttatag aacatatttt cctttagatc 1980
aaggcaaaaa tatcaggagc ttttttacac acctactaaa aagttatta tgtagctgaa 2040
acaaaaatgc cagaaggata atattgattc ctcacatctt taacttagta ttttacctag 2100

```
catttcaaaa cccaaatggc tagaacatgt ttaattaaat ttcacaatat aaagttctac      2160
agttaattat gtgcatatta aaacaatggc ctggttcaat ttctttcttt ccttaataaa      2220
tttaagtttt ttccccccaa aattatcagt gctctgcttt tagtcacgtg tattttcatt      2280
accactcgta aaaggtatc ttttttaaat gaattaaata ttgaaacact gtacaccata      2340
gtttacaata ttatgtttcc taattaaaat aagaattgaa tgtcaatatg agatattaaa      2400
ataagcacag aaaatc                                                    2416

<210> SEQ ID NO 40
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (227)..(227)
<223> OTHER INFORMATION: F227M

<400> SEQUENCE: 40
```

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Met Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

-continued

```
Asn Phe Gly Pro Thr Val Asp Gly Asp Phe Leu Thr Asp Met Pro Asp
    290                 295                 300
Ile Leu Leu Glu Leu Gly Gln Phe Lys Lys Thr Gln Ile Leu Val Gly
305                 310                 315                 320
Val Asn Lys Asp Glu Gly Thr Ala Phe Leu Val Tyr Gly Ala Pro Gly
                325                 330                 335
Phe Ser Lys Asp Asn Asn Ser Ile Ile Thr Arg Lys Glu Phe Gln Glu
            340                 345                 350
Gly Leu Lys Ile Phe Phe Pro Gly Val Ser Glu Phe Gly Lys Glu Ser
        355                 360                 365
Ile Leu Phe His Tyr Thr Asp Trp Val Asp Asp Gln Arg Pro Glu Asn
    370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
            420                 425                 430
Trp Met Gly Val Met His Gly Tyr Glu Ile Glu Phe Val Phe Gly Leu
        435                 440                 445
Pro Leu Glu Arg Arg Asp Asn Tyr Thr Lys Ala Glu Glu Ile Leu Ser
    450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
            500                 505                 510
Lys Leu Arg Ala Gln Gln Cys Arg Phe Trp Thr Ser Phe Phe Pro Lys
        515                 520                 525
Val Leu Glu Met Thr Gly Asn Ile Asp Glu Ala Glu Trp Glu Trp Lys
    530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570

<210> SEQ ID NO 41
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 41
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat actgaagatg acatcataat tgcaacaaag     240
aatggaaaag tcagagggat gaacttgaca gtttttggtg gcacggtaac agcctttctt     300
ggaattccct atgcacagcc acctcttggt agacttcgat tcaaaaagcc acagtctctg     360
accaagtggt ctgatatttg gaatgccaca aaatatgcaa attcttgctg tcagaacata     420
```

```
gatcaaagtt ttccaggctt ccatggatca gagatgtgga acccaaacac tgacctcagt      480
gaagactgtt tatatctaaa tgtatggatt ccagcaccta aaccaaaaaa tgccactgta      540
ttgatatgga tttatggtgg tggttttcaa actggaacat catctttaca tgtttatgat      600
ggcaagtttc tggctcgggt tgaaagagtt attgtagtgt caatgaacta tagggtgggt      660
gccctaggat tcttagcttt gccaggaaat cctgaggctc cagggaacat gggtttattt      720
gatcaacagt tggctcttca gtgggttcaa aaaatatag cagcctttgg tggaaatcct      780
aaaagtgtaa ctctctttgg agaaagttca ggagcagctt cagttagcct gcatttgctt      840
tctcctggaa gccattcatt gttcaccaga gccattctgc aaagtggatc ctttaatgct      900
ccttgggcgg taacatctct ttatgaagct aggaacagaa cgttgaactt agctaaattg      960
actggttgct ctagagagaa tgagactgaa ataatcaagt gtcttagaaa taaagatccc      1020
caagaaattc ttctgaatga agcatttgtt gtcccctatg ggactccttt gtcagtaaac      1080
tttggtccga ccgtggatgg tgattttctc actgacatgc agacatatt acttgaactt      1140 ggacaattta aaaaaccca gattttggtg gtgttaata aagatgaagg gacagctttt      1200
ttagtctatg tgctcctgg cttcagcaaa gataacaata gtatcataac tagaaaagaa      1260
tttcaggaag gttttaaaaaat attttttcca ggagtgagtg agtttggaaa ggaatccatc      1320 cttttttcatt acacagactg ggtagatgat cagagacctg aaaactaccg tgaggccttg      1380
ggtgatgttg ttgggggatta aatttcata tgccctgcct tggagttcac caagaagttc      1440
tcagaatggg gaaataatgc ctttttctac tattttgaac accgatcctc caaacttccg      1500
tggccagaat ggatgggagt gatgcatggc tatgaaattg aatttgtctt tggtttacct      1560
ctggaaagaa gagataatta cacaaaagcc gaggaaattt tgagtagatc catagtgaaa      1620
cggtgggcaa attttgcaaa atatgggaat ccaaatgaga ctcagaacaa tagcacaagc      1680
tggcctgtct tcaaaagcac tgaacaaaaa tatctaacct tgaatacaga gtcaacaaga      1740
ataatgacga aactacgtgc tcaacaatgt cgattctgga catcattttt tccaaaagtc      1800
ttggaaatga caggaaatat tgatgaagca gaatgggagt ggaaagcagg attccatcgc      1860
tggaacaatt acatgatgga ctggaaaaat caatttaacg attacactag caagaaagaa      1920
agttgtgtgg gtctctaatt aatagattta ccctttatag aacatatttt cctttagatc      1980
aaggcaaaaa tatcaggagc ttttttacac acctactaaa aaagttatta tgtagctgaa      2040
acaaaaatgc cagaaggata atattgattc ctcacatctt taacttagta ttttacctag      2100
catttcaaaa cccaaatggc tagaacatgt ttaattaaat ttcacaatat aaagttctac      2160
agttaattat gtgcatatta aaacaatggc ctggttcaat ttctttcttt ccttaataaa      2220
tttaagtttt ttccccccaa aattatcagt gctctgcttt tagtcacgtg tatttttcatt      2280 accactcgta aaaaggtatc tttttttaaat gaattaaata ttgaaacact gtacaccata      2340
gtttacaata ttatgtttcc taattaaaat aagaattgaa tgtcaatatg agatattaaa      2400
ataagcacag aaaatc                                                    2416
```

<210> SEQ ID NO 42
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (199)..(199)
<223> OTHER INFORMATION: A199S

```
<400> SEQUENCE: 42

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
```

```
            405                 410                 415
Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
            450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Pro Lys
            515                 520                 525

Val Leu Glu Met Thr Gly Asn Ile Asp Glu Ala Glu Trp Glu Trp Lys
            530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 43
<211> LENGTH: 2416
<212> TYPE: DNA
<213> ORGANISM: Homo sapiens

<400> SEQUENCE: 43
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat actgaagatg acatcataat tgcaacaaag     240
aatggaaaag tcagagggat gaacttgaca gttttggtg gcacggtaac agcctttctt     300
ggaattccct atgcacagcc acctcttggt agacttcgat tcaaaaagcc acagtctctg     360
accaagtggt ctgatatttg aatgccaca aaatatgcaa attcttgctg tcagaacata     420
gatcaaagtt ttccaggctt ccatggatca gagatgtgga acccaaacac tgacctcagt     480
gaagactgtt tatatctaaa tgtatggatt ccagcaccta accaaaaaa tgccactgta     540
ttgatatgga tttatggtgg tggttttcaa actggaacat catctttaca tgtttatgat     600
ggcaagtttc tggctcgggt tgaaagagtt attgtagtgt caatgaacta tagggtgggt     660
gccctaggat tcttagcttt gccaggaaat cctgaggctc cagggaacat gggtttattt     720
gatcaacagt tggctcttca gtgggttcaa aaaatatag cagcctttgg tggaaatcct     780
aaaagtgtaa ctctctttgg agaaagtgca ggagcagctt cagttagcct gcatttgctt     840
tctcctggaa gccattcatt gttcaccaga gccattctgc aaagtggatc ctttaatgct     900
ccttgggcgg taacatctct ttatgaagct aggaacagaa cgttgaactt agctaaattg     960
actggttgct ctagagagaa tgagactgaa ataatcaagt gtcttagaaa taaagatccc    1020
caagaaattc ttctgaatga agcatttgtt gtcccctatg ggactccttt gtcagtaaac    1080
tttggtccga ccgtggatgg tgattttctc actgacatgc agacatatt acttgaactt    1140
ggacaattta aaaaaaccca gattttggtg ggtgttaata agatgaagg acagcttttt    1200
```

-continued

```
ttagtctatg gtgctcctgg cttcagcaaa gataacaata gtatcataac tagaaaagaa    1260
tttcaggaag gtttaaaaat attttttcca ggagtgagtg agtttggaaa ggaatccatc    1320 cttttcatt acacagactg ggtagatgat cagagacctg aaaactaccg tgaggccttg     1380
ggtgatgttg ttgggggatta taatttcata tgccctgcct tggagttcac caagaagttc   1440
tcagaatggg gaaataatgc cttttttctac tattttgaac accgatcctc caaacttccg   1500
tggccagaat ggatgggagt gatgcatggc tatgaaattg aatttgtctt tggtttacct   1560
ctggaaagaa gagataatta cacaaaagcc gaggaaattt tgagtagatc catagtgaaa   1620
cggtgggcaa attttgcaaa atatgggaat ccaaatgaga ctcagaacaa tagcacaagc   1680
tggcctgtct tcaaaagcac tgaacaaaaa tatctaacct tgaatacaga gtcaacaaga   1740
ataatgacga aactacgtgc tcaacaatgt cgattctgga catcattttt tccaaaagtc   1800
ttggaaatga caggaaatat tgatgaagca gaatgggagt ggaaagcagg attccatcgc   1860
tggaacaatt acatgatgga ctggaaaaat caatttaacg attacactag caagaaagaa   1920
agttgtgtgg gtctctaatt aatagattta ccctttatag aacatatttt cctttagatc   1980
aaggcaaaaa tatcaggagc tttttttacac acctactaaa aaagttatta tgtagctgaa   2040
acaaaaatgc cagaaggata atattgattc ctcacatctt taacttagta ttttacctag   2100
catttcaaaa cccaaatggc tagaacatgt ttaattaaat ttcacaatat aaagttctac   2160
agttaattat gtgcatatta aaacaatggc ctggttcaat ttctttcttt ccttaataaa   2220
tttaagtttt ttccccccaa aattatcagt gctctgcttt tagtcacgtg tatttttcatt 2280 accactcgta aaaggtatc ttttttaaat gaattaaata ttgaaacact gtacaccata    2340
gtttacaata ttatgttttcc taattaaaat aagaattgaa tgtcaatatg agatattaaa  2400
ataagcacag aaaatc                                                   2416
```

<210> SEQ ID NO 44
<211> LENGTH: 574
<212> TYPE: PRT
<213> ORGANISM: Homo sapiens
<220> FEATURE:
<221> NAME/KEY: MISC_FEATURE
<222> LOCATION: (1)..(567)
<223> OTHER INFORMATION: Human butyrylcholinesterase

<400> SEQUENCE: 44

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125
```

-continued

```
Asp Gly Lys Phe Leu Ala Arg Val Glu Arg Val Ile Val Val Ser Met
            130                 135                 140
Asn Tyr Arg Val Gly Ala Leu Gly Phe Leu Ala Leu Pro Gly Asn Pro
145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Asn Pro Lys Ser Val
                180                 185                 190
Thr Leu Phe Gly Glu Ser Ala Gly Ala Ala Ser Val Ser Leu His Leu
            195                 200                 205
Leu Ser Pro Gly Ser His Ser Leu Phe Thr Arg Ala Ile Leu Gln Ser
210                 215                 220
Gly Ser Phe Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
            260                 265                 270
Leu Leu Asn Glu Ala Phe Val Val Pro Tyr Gly Thr Pro Leu Ser Val
            275                 280                 285
Asn Phe Gly Pro Thr Val Asp Gly Asp Phe Leu Thr Asp Met Pro Asp
290                 295                 300
Ile Leu Leu Glu Leu Gly Gln Phe Lys Lys Thr Gln Ile Leu Val Gly
305                 310                 315                 320
Val Asn Lys Asp Glu Gly Thr Ala Phe Leu Val Tyr Gly Ala Pro Gly
                325                 330                 335
Phe Ser Lys Asp Asn Asn Ser Ile Ile Thr Arg Lys Glu Phe Gln Glu
            340                 345                 350
Gly Leu Lys Ile Phe Phe Pro Gly Val Ser Glu Phe Gly Lys Glu Ser
            355                 360                 365
Ile Leu Phe His Tyr Thr Asp Trp Val Asp Asp Gln Arg Pro Glu Asn
            370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
                420                 425                 430
Trp Met Gly Val Met His Gly Tyr Glu Ile Glu Phe Val Phe Gly Leu
            435                 440                 445
Pro Leu Glu Arg Arg Asp Asn Tyr Thr Lys Ala Glu Glu Ile Leu Ser
            450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
                500                 505                 510
Lys Leu Arg Ala Gln Gln Cys Arg Phe Trp Thr Ser Phe Phe Pro Lys
            515                 520                 525
Val Leu Glu Met Thr Gly Asn Ile Asp Glu Ala Glu Trp Glu Trp Lys
            530                 535                 540
Ala Gly Phe His Arg Trp Asn Asn Tyr Met Met Asp Trp Lys Asn Gln
```

```
                      545                 550                 555                 560

Phe Asn Asp Tyr Thr Ser Lys Lys Glu Ser Cys Val Gly Leu
                565                 570

<210> SEQ ID NO 45
<211> LENGTH: 574
<212> TYPE: PRT
<213> ORGANISM: Homo sapiens

<400> SEQUENCE: 45

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Gly Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350
```

```
Gly Leu Lys Ile Phe Pro Gly Val Ser Glu Phe Gly Lys Glu Ser
            355                 360                 365

Ile Leu Phe His Tyr Thr Asp Trp Val Asp Asp Gln Arg Pro Glu Asn
        370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
    515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 46
<211> LENGTH: 574
<212> TYPE: PRT
<213> ORGANISM: Homo sapiens

<400> SEQUENCE: 46

Glu Asp Asp Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
                20                  25                  30

Tyr Ala Gln Pro Pro Leu Gly Arg Leu Arg Phe Lys Lys Pro Gln Ser
            35                  40                  45

Leu Thr Lys Trp Ser Asp Ile Trp Asn Ala Thr Lys Tyr Ala Asn Ser
        50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160
```

```
Glu Ala Pro Gly Asn Met Gly Leu Phe Asp Gln Gln Leu Ala Leu Gln
                165                 170                 175

Trp Val Gln Lys Asn Ile Ala Ala Phe Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
                260                 265                 270

Leu Leu Asn Glu Ala Phe Val Val Pro Tyr Gly Thr Pro Leu Ser Val
            275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
        370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Val Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

```
<210> SEQ ID NO 47
<211> LENGTH: 574
<212> TYPE: PRT
<213> ORGANISM: Homo sapiens

<400> SEQUENCE: 47

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380
```

```
Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
            405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
                500                 505                 510

Lys Leu Arg Ala Gln Gln Cys Arg Phe Trp Thr Ser Phe Phe Pro Lys
            515                 520                 525

Val Leu Glu Met Thr Gly Asn Ile Asp Glu Thr Glu Trp Glu Trp Lys
530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 48
<211> LENGTH: 574
<212> TYPE: PRT
<213> ORGANISM: Equus caballus

<400> SEQUENCE: 48

Glu Glu Asp Ile Ile Ile Thr Thr Lys Asn Gly Lys Val Arg Gly Met
1               5                   10                  15

Asn Leu Pro Val Leu Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asn Ile Trp Asn Ala Thr Lys Tyr Ala Asn Ser
    50                  55                  60

Cys Tyr Gln Asn Thr Asp Gln Ser Phe Pro Gly Phe Leu Gly Ser Glu
65                  70                  75                  80

Met Trp Asn Pro Asn Thr Glu Leu Ser Glu Asp Cys Leu Tyr Leu Asn
                85                  90                  95

Val Trp Ile Pro Ala Pro Lys Pro Lys Asn Ala Thr Val Met Ile Trp
            100                 105                 110

Ile Tyr Gly Gly Gly Phe Gln Thr Gly Thr Ser Ser Leu Pro Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Ser Glu Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Arg Ser Val
```

```
                180                 185                 190
Thr Leu Phe Gly Glu Ser Ala Gly Ala Ala Ser Val Ser Leu His Leu
            195                 200                 205
Leu Ser Pro Arg Ser Gln Pro Leu Phe Thr Arg Ala Ile Leu Gln Ser
        210                 215                 220
Gly Ser Ser Asn Ala Pro Trp Ala Val Thr Ser Leu Tyr Glu Ala Arg
225                 230                 235                 240
Asn Arg Thr Leu Thr Leu Ala Lys Arg Met Gly Cys Ser Arg Asp Asn
                245                 250                 255
Glu Thr Glu Met Ile Lys Cys Leu Arg Asp Lys Asp Pro Gln Glu Ile
            260                 265                 270
Leu Leu Asn Glu Val Phe Val Val Pro Tyr Asp Thr Leu Leu Ser Val
        275                 280                 285
Asn Phe Gly Pro Thr Val Asp Gly Asp Phe Leu Thr Asp Met Pro Asp
290                 295                 300
Thr Leu Leu Gln Leu Gly Gln Phe Lys Arg Thr Gln Ile Leu Val Gly
305                 310                 315                 320
Val Asn Lys Asp Glu Gly Thr Ala Phe Leu Val Tyr Gly Ala Pro Gly
                325                 330                 335
Phe Ser Lys Asp Asn Asn Ser Ile Ile Thr Arg Lys Glu Phe Gln Glu
            340                 345                 350
Gly Leu Lys Ile Phe Phe Pro Arg Val Ser Glu Phe Gly Arg Glu Ser
        355                 360                 365
Ile Leu Phe His Tyr Met Asp Trp Leu Asp Asp Gln Arg Ala Glu Asn
    370                 375                 380
Tyr Arg Glu Ala Leu Asp Asp Val Val Gly Asp Tyr Asn Ile Ile Cys
385                 390                 395                 400
Pro Ala Leu Glu Phe Thr Arg Lys Phe Ser Glu Leu Gly Asn Asp Ala
                405                 410                 415
Phe Phe Tyr Tyr Phe Glu His Arg Ser Thr Lys Leu Pro Trp Pro Glu
            420                 425                 430
Trp Met Gly Val Met His Gly Tyr Glu Ile Glu Phe Val Phe Gly Leu
        435                 440                 445
Pro Leu Glu Arg Arg Val Asn Tyr Thr Arg Ala Glu Glu Ile Leu Ser
    450                 455                 460
Arg Ser Ile Met Lys Arg Trp Ala Asn Phe Ala Lys Tyr Gly Asn Pro
465                 470                 475                 480
Asn Gly Thr Gln Asn Asn Ser Thr Arg Trp Pro Val Phe Lys Ser Thr
                485                 490                 495
Glu Gln Lys Tyr Leu Thr Leu Asn Thr Glu Ser Pro Lys Val Tyr Thr
            500                 505                 510
Lys Leu Arg Ala Gln Gln Cys Arg Phe Trp Thr Leu Phe Phe Pro Lys
        515                 520                 525
Val Leu Glu Leu Thr Gly Asn Ile Asp Glu Ala Glu Arg Glu Trp Lys
    530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Ser Asp Phe
                565                 570

<210> SEQ ID NO 49
<211> LENGTH: 574
<212> TYPE: PRT
<213> ORGANISM: Felis catus
```

<400> SEQUENCE: 49

```
Glu Glu Asp Ile Ile Thr Thr Lys Asn Gly Lys Val Arg Gly Met
1               5                   10                  15
Asn Leu Pro Val Leu Asp Gly Thr Val Thr Ala Phe Leu Gly Ile Pro
            20                  25                  30
Tyr Ala Gln Pro Pro Leu Gly Arg Leu Arg Phe Lys Lys Pro Gln Phe
            35                  40                  45
Leu Thr Lys Trp Ser Asp Ile Trp Asn Ala Thr Lys Tyr Ala Asn Ser
    50                  55                  60
Cys Tyr Gln Asn Ala Asp Gln Ser Phe Pro Gly Phe Pro Gly Ser Glu
65                  70                  75                  80
Met Trp Asn Pro Asn Thr Asp Leu Ser Glu Asp Cys Leu Tyr Leu Asn
                85                  90                  95
Val Trp Ile Pro Thr Pro Lys Pro Lys Asn Ala Thr Val Met Ile Trp
            100                 105                 110
Ile Tyr Gly Gly Gly Phe Gln Thr Gly Thr Ser Ser Leu Pro Val Tyr
            115                 120                 125
Asp Gly Lys Phe Leu Ala Arg Val Glu Arg Val Ile Val Val Ser Met
            130                 135                 140
Asn Tyr Arg Val Gly Ala Leu Gly Phe Leu Ala Leu Pro Gly Asn Pro
145                 150                 155                 160
Glu Val Pro Gly Asn Met Gly Leu Phe Asp Gln Gln Leu Ala Leu Gln
                165                 170                 175
Trp Val Gln Lys Asn Ile Ala Ala Phe Gly Gly Asn Pro Lys Ser Val
            180                 185                 190
Thr Leu Phe Gly Glu Ser Ala Gly Ala Gly Ser Val Ser Leu His Leu
            195                 200                 205
Leu Ser Pro Arg Ser Gln Pro Leu Phe Thr Arg Ala Ile Leu Gln Ser
    210                 215                 220
Gly Ser Ser Asn Ala Pro Trp Ala Val Met Ser Leu Asp Glu Ala Lys
225                 230                 235                 240
Asn Arg Thr Leu Thr Leu Ala Lys Phe Ile Gly Cys Ser Lys Glu Asn
                245                 250                 255
Asp Thr Glu Ile Ile Lys Cys Leu Arg Asn Lys Asp Pro Gln Glu Ile
            260                 265                 270
Leu Leu Asn Glu Leu Leu Val Val Pro Ser Asp Thr Leu Leu Ser Val
            275                 280                 285
Asn Phe Gly Pro Val Val Asp Gly Asp Phe Leu Thr Asp Met Pro Asp
            290                 295                 300
Thr Leu Leu Gln Leu Gly Gln Phe Lys Lys Thr Gln Ile Leu Val Gly
305                 310                 315                 320
Val Asn Lys Asp Glu Gly Thr Ala Phe Leu Val Tyr Gly Ala Pro Gly
                325                 330                 335
Phe Ser Lys Asp Asn Asp Ser Ile Ile Thr Arg Lys Glu Phe Gln Glu
            340                 345                 350
Gly Leu Lys Ile Tyr Phe Pro Gly Val Ser Glu Phe Gly Arg Glu Ala
            355                 360                 365
Ile Leu Phe Tyr Tyr Val Asp Leu Leu Asp Gln Arg Ala Glu Lys
            370                 375                 380
Tyr Arg Glu Ala Leu Asp Asp Val Leu Gly Asp Tyr Asn Ile Ile Cys
385                 390                 395                 400
Pro Ala Leu Glu Phe Thr Thr Lys Phe Ser Glu Leu Gly Asn Asn Ala
```

```
                405                 410                 415
Phe Phe Tyr Tyr Phe Glu His Arg Ser Ser Gln Leu Pro Trp Pro Glu
            420                 425                 430
Trp Met Gly Val Met His Gly Tyr Glu Ile Glu Phe Val Phe Gly Leu
        435                 440                 445
Pro Leu Glu Arg Arg Val Asn Tyr Thr Arg Ala Glu Glu Ile Leu Ser
    450                 455                 460
Arg Ser Ile Met Asn Tyr Trp Ala Asn Phe Ala Lys Tyr Gly Asn Pro
465                 470                 475                 480
Asn Gly Thr Gln Asn Asn Ser Thr Arg Trp Pro Ala Phe Arg Ser Thr
                485                 490                 495
Asp Gln Lys Tyr Leu Thr Leu Asn Ala Glu Ser Pro Lys Val Tyr Thr
            500                 505                 510
Lys Leu Arg Ala Gln Gln Cys Arg Phe Trp Thr Leu Phe Phe Pro Lys
        515                 520                 525
Val Leu Glu Met Thr Gly Asn Ile Asp Glu Ala Glu Arg Glu Trp Arg
    530                 535                 540
Ala Gly Phe Tyr Arg Trp Asn Asn Tyr Met Met Asp Trp Lys Asn Gln
545                 550                 555                 560
Phe Asn Asp Tyr Thr Ser Lys Lys Glu Ser Cys Ala Gly Leu
                565                 570

<210> SEQ ID NO 50
<211> LENGTH: 574
<212> TYPE: PRT
<213> ORGANISM: Rattus sp.

<400> SEQUENCE: 50

Glu Glu Asp Val Ile Ile Thr Thr Lys Thr Gly Arg Val Arg Gly Leu
1               5                   10                  15
Ser Met Pro Ile Leu Gly Gly Thr Val Thr Ala Phe Leu Gly Ile Pro
            20                  25                  30
Tyr Ala Gln Pro Pro Leu Gly Ser Leu Arg Phe Lys Lys Pro Gln Pro
        35                  40                  45
Leu Asn Lys Trp Pro Asp Val Tyr Asn Ala Thr Lys Tyr Ala Asn Ser
    50                  55                  60
Cys Tyr Gln Asn Ile Asp Gln Ala Phe Pro Gly Phe Gln Gly Ser Glu
65                  70                  75                  80
Met Trp Asn Pro Asn Thr Asn Leu Ser Glu Asp Cys Leu Tyr Leu Asn
                85                  90                  95
Val Trp Ile Pro Val Pro Lys Pro Lys Asn Ala Thr Val Met Val Trp
            100                 105                 110
Val Tyr Gly Gly Gly Phe Gln Thr Gly Thr Ser Ser Leu Pro Val Tyr
        115                 120                 125
Asp Gly Lys Phe Leu Thr Arg Val Glu Arg Val Ile Val Val Ser Met
    130                 135                 140
Asn Tyr Arg Val Gly Ala Leu Gly Phe Leu Ala Phe Pro Gly Asn Ser
145                 150                 155                 160
Glu Ala Pro Gly Asn Met Gly Leu Phe Asp Gln Gln Leu Ala Leu Gln
                165                 170                 175
Trp Ile Gln Arg Asn Ile Ala Ala Phe Gly Gly Asn Pro Lys Ser Val
            180                 185                 190
Thr Leu Phe Gly Glu Ser Ala Gly Ala Ala Ser Val Ser Leu His Leu
        195                 200                 205
```

```
Leu Cys Pro Gln Ser Tyr Pro Leu Phe Thr Arg Ala Ile Leu Glu Ser
    210                 215                 220

Gly Ser Ser Asn Ala Pro Trp Ala Val Lys His Pro Glu Glu Ala Arg
225                 230                 235                 240

Asn Arg Thr Leu Thr Leu Ala Lys Phe Ile Gly Cys Ser Lys Glu Asn
                245                 250                 255

Glu Lys Glu Ile Ile Thr Cys Leu Arg Ser Lys Asp Pro Gln Glu Ile
                260                 265                 270

Leu Leu Asn Glu Lys Leu Val Leu Pro Ser Asp Ser Ile Arg Ser Ile
                275                 280                 285

Asn Phe Gly Pro Thr Val Asp Gly Asp Phe Leu Thr Asp Met Pro His
290                 295                 300

Thr Leu Leu Gln Leu Gly Lys Val Lys Thr Ala Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asp Ser Leu Ile Thr Arg Arg Glu Phe Gln Glu
                340                 345                 350

Gly Leu Asn Met Tyr Phe Pro Gly Val Ser Ser Leu Gly Lys Glu Ala
                355                 360                 365

Ile Leu Phe Tyr Tyr Val Asp Trp Leu Gly Asp Gln Thr Pro Glu Val
370                 375                 380

Tyr Arg Glu Ala Phe Asp Asp Ile Ile Gly Asp Tyr Asn Ile Ile Cys
385                 390                 395                 400

Pro Ala Leu Glu Phe Thr Lys Lys Phe Ala Glu Leu Glu Ile Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
                435                 440                 445

Pro Leu Glu Arg Arg Val Asn Tyr Thr Arg Ala Glu Glu Ile Phe Ser
450                 455                 460

Arg Ser Ile Met Lys Thr Trp Ala Asn Phe Ala Lys Tyr Gly His Pro
465                 470                 475                 480

Asn Gly Thr Gln Gly Asn Ser Thr Val Trp Pro Val Phe Thr Ser Thr
                485                 490                 495

Glu Gln Lys Tyr Leu Thr Leu Asn Thr Glu Lys Ser Lys Ile Asn Ser
                500                 505                 510

Lys Leu Arg Ala Pro Gln Cys Gln Phe Trp Arg Leu Phe Phe Pro Lys
                515                 520                 525

Val Leu Glu Ile Thr Gly Asp Ile Asp Glu Arg Glu Gln Glu Trp Lys
530                 535                 540

Ala Gly Phe His Arg Trp Ser Asn Tyr Met Met Asp Trp Lys Asn Gln
545                 550                 555                 560

Phe Asn Asp Tyr Thr Ser Lys Lys Glu Thr Cys Thr Asp Leu
                565                 570

<210> SEQ ID NO 51
<211> LENGTH: 2416
<212> TYPE: DNA
<213> ORGANISM: Artificial
<220> FEATURE:
<223> OTHER INFORMATION: Butyrylcholinesterase variant

<400> SEQUENCE: 51
```

```
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat actgaagatg acatcataat tgcaacaaag     240 aatgaaaag tcagagggat gaacttgaca gttttggtg gcacggtaac agcctttctt      300
ggaattccct atgcacagcc acctcttggt agacttcgat tcaaaagcc acagtctctg      360 accaagtggt ctgatatttg gaatgccaca aaatatgcaa attcttgctg tcagaacata     420
gatcaaagtt ttccaggctt ccatggatca gagatgtgga acccaaacac tgacctcagt     480
gaagactgtt tatatctaaa tgtatggatt ccagcaccta accaaaaaa tgccactgta      540 ttgatatgga tttatggtgg tggttttcaa actggaacat catctttaca tgtttatgat     600
ggcaagtttc tggctcgggt tgaaagagtt attgtagtgt caatgaacta tagggtgggt     660
gccctaggat tcttagcttt gccaggaaat cctgaggctc cagggaacat gggtttattt     720
gatcaacagt tggctcttca gtgggttcaa aaaaatatag cagcctttgg tggaaatcct     780
aaaagtgtaa ctctcttggg agaaagtgca ggagcagctt cagttagcct gcatttgctt     840
tctcctggaa gccattcatt gttcaccaga gccattctgc aaagtggatc cgcgaatgct     900
ccttgggcgg taacatctct ttatgaagct aggaacagaa cgttgaactt agctaaattg     960
actggttgct ctagagagaa tgagactgaa ataatcaagt gtcttagaaa taaagatccc    1020
caagaaattc ttctgaatga agcatttgtt gtcccctatg ggactccttt gggtgtaaac    1080
tttggtccga ccgtggatgg tgattttctc actgacatgc agacatatt acttgaactt    1140 ggacaattta aaaaaaccca gattttggtg ggtgttaata agatgaagg acatggtttt    1200 ttagtcatgg gtgctcctgg cttcagcaaa gataacaata gtatcataac tagaaaagaa    1260
tttcaggaag gtttaaaaat attttttcca ggagtgagtg agtttggaaa ggaatccatc    1320 cttttttcatt acacagactg ggtagatgat cagagacctg aaaactaccg tgaggccttg    1380
ggtgatgttg ttgggggatta taatttcata tgccctgcct tggagttcac caagaagttc    1440
tcagaatggg gaaataatgc cttttttctac tattttgaac accgatcctc caaacttccg    1500
tggccagaat ggatgggagt gatgcatggc tatgaaattg aatttgtctt tggttttacct    1560 ctggaaagaa gagataatta cacaaaagcc gaggaaattt tgagtagatc catagtgaaa    1620
cggtgggcaa attttgcaaa atatgggaat ccaaatgaga ctcagaacaa tagcacaagc    1680
tggcctgtct tcaaaagcac tgaacaaaaaa tatctaacct tgaatacaga gtcaacaaga    1740
ataatgacga aactacgtgc tcaacaatgt cgattctgga catcattttt tccaaaagtc    1800
ttggaaatga caggaaatat tgatgaagca gaatgggagt ggaaagcagg attccatcgc    1860
tggaacaatt acatgatgga ctggaaaaat caatttaacg attacactag caagaaagaa    1920
agttgtgtgg gtctctaatt aatagattta ccctttatag aacatatttt cctttagatc    1980
aaggcaaaaa tatcaggagc ttttttacac acctactaaa aaagttatta tgtagctgaa    2040
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttccccccaa aattatcagt gctctgcttt tagtcacgtg tatttcatt    2280 accactcgta aaaggtatc ttttttaaat gaattaaata ttgaaacact gtacaccata    2340
gtttacaata ttatgtttcc taattaaaat aagaattgaa tgtcaatatg agatattaaa    2400
```

-continued

```
ataagcacag aaaatc                                              2416
```

<210> SEQ ID NO 52
<211> LENGTH: 574
<212> TYPE: PRT
<213> ORGANISM: Artificial
<220> FEATURE:
<223> OTHER INFORMATION: Butyrylcholinesterase variant
<220> FEATURE:
<221> NAME/KEY: MISC_FEATURE
<222> LOCATION: (227)..(227)
<223> OTHER INFORMATION: F227A
<220> FEATURE:
<221> NAME/KEY: MISC_FEATURE
<222> LOCATION: (287)..(287)
<223> OTHER INFORMATION: S287G
<220> FEATURE:
<221> NAME/KEY: MISC_FEATURE
<222> LOCATION: (328)..(328)
<223> OTHER INFORMATION: A328W
<220> FEATURE:
<221> NAME/KEY: MISC_FEATURE
<222> LOCATION: (332)..(332)
<223> OTHER INFORMATION: Y332M

<400> SEQUENCE: 52

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270
```

```
Leu Leu Asn Glu Ala Phe Val Val Pro Tyr Gly Thr Pro Leu Gly Val
        275                 280                 285

Asn Phe Gly Pro Thr Val Asp Gly Asp Phe Leu Thr Asp Met Pro Asp
        290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Met Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
        370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
        450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
                500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
        530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 53
<211> LENGTH: 34
<212> TYPE: DNA
<213> ORGANISM: Artificial
<220> FEATURE:
<223> OTHER INFORMATION: Target site for Flp recombinase

<400> SEQUENCE: 53
gaagttccta ttctctagaa agtataggaa cttc                              34
```